(12) United States Patent
Tan et al.

(10) Patent No.: US 8,846,311 B2
(45) Date of Patent: Sep. 30, 2014

(54) MAP KINASE KINASE KINASE KINASE 3 (MAP4K3) AS A BIOMARKER AND THERAPEUTIC TARGET FOR AUTOIMMUNE DISEASE, CANCER, INFLAMMATION AND IL-17-ASSOCIATED DISEASE

(75) Inventors: Tse-Hua Tan, Miaoli County (TW); Huai-Chia Chuang, Miaoli County (TW)

(73) Assignee: National Health Research Institutes, Miaoli County (TW)

( * ) Notice: Subject to any disclaimer, the term of this patent is extended or adjusted under 35 U.S.C. 154(b) by 5 days.

(21) Appl. No.: 13/548,212

(22) Filed: Jul. 13, 2012

(65) Prior Publication Data

US 2013/0017550 A1 Jan. 17, 2013

Related U.S. Application Data

(60) Provisional application No. 61/508,057, filed on Jul. 14, 2011.

(51) Int. Cl.
*C12Q 1/00* (2006.01)
*C12Q 1/68* (2006.01)
*G01N 33/567* (2006.01)
*G01N 33/574* (2006.01)
*G01N 33/50* (2006.01)

(52) U.S. Cl.
CPC ...... *G01N 33/5041* (2013.01); *G01N 33/57484* (2013.01); *C12Q 1/6886* (2013.01); *G01N 2333/91205* (2013.01); *C12Q 1/6883* (2013.01); *C12Q 2600/136* (2013.01)
USPC ............ 435/4; 435/6.13; 435/6.18; 435/7.21; 435/7.23

(58) Field of Classification Search
CPC ........... C12Q 1/6886; C12Q 2600/136; C12Q 2600/112; C12Q 2600/118; C12N 5/0693; C12N 2502/30; G01N 33/57407; G01N 2500/00; G01N 33/574; G01N 2800/52; C07K 14/47; C07K 16/30
See application file for complete search history.

(56) References Cited

U.S. PATENT DOCUMENTS

| | | | |
|---|---|---|---|
| 7,666,607 B1 | 2/2010 | Zapata et al. | |
| 8,236,820 B2 * | 8/2012 | Rigas | 514/320 |
| 2009/0099029 A1 | 4/2009 | Samuels | |
| 2009/0196912 A1 | 8/2009 | Eickhoff | |
| 2009/0317392 A1 | 12/2009 | Nakamura et al. | |

OTHER PUBLICATIONS

Hoesel et al. Mol. Cancer. 2013. 12:86-101.*
O'Sullivan et al. 2007. Expert Opin. Ther. Targets 11:111-122.*
Shostak et al. 2011. Breast Cancer Res. 13:214-221.*
Wright et al. 2003. Mol. Cell. Biol. 23:2068.*
Jiang et al 2004. Nutrition and Cancer 49:209-216.*
Ling et al. 2010. Br. J. Pharmacology 161:1763-1777.*
Yoshida et al.—2007. Neurotoxicology 28:381-386.*
Chuang et al. (2011) "The kinase GLK controls autoimmunity and NF-kB signaling by activating the kinase PKC-θ in T cells". Nat Immunol. 12(11):1113-1118.

* cited by examiner

*Primary Examiner* — Shulamith H Shafer
(74) *Attorney, Agent, or Firm* — Hsiu-Ming Saunders; Intellectual Property Connections, Inc.

(57) ABSTRACT

Methods for identifying a therapeutic agent for treating a Germinal Center Kinase (GCK)-Like Kinase (GLK)-mediated disease are disclosed. Methods for detecting a modulation of GLK signaling by a test compound are disclosed. Also disclosed are methods for detecting the presence and/or severity of an autoimmune disease and/or cancer.

12 Claims, 39 Drawing Sheets

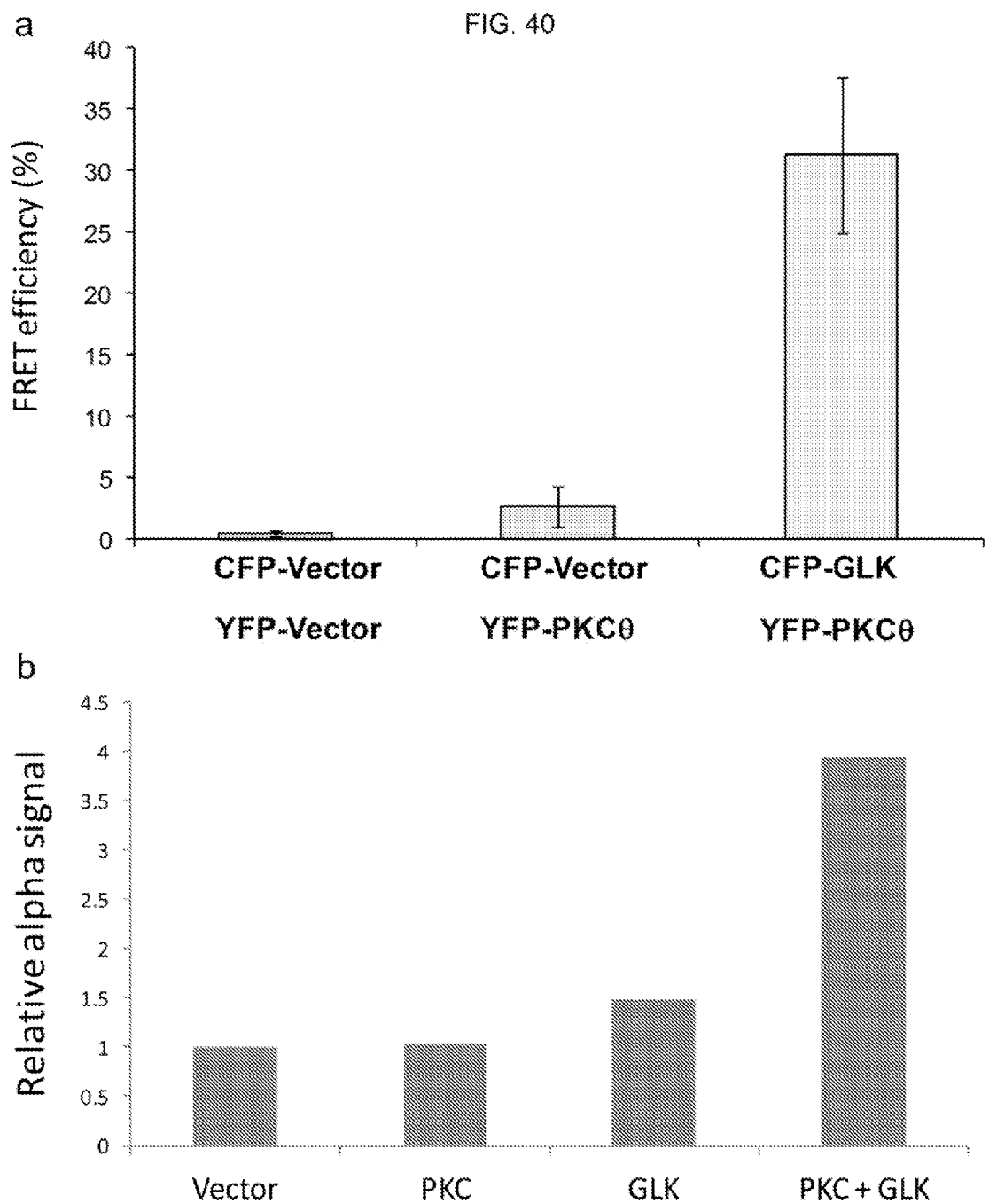

SEQUENCE LISTING

<160> NUMBER OF SEQ ID NOS: 8

<210> SEQ ID NO 1
<211> LENGTH: 884
<212> TYPE: PRT
<213> ORGANISM: Homo sapiens

<400> SEQUENCE: 1

```
Met Ala Gln Glu Asp Phe Glu Leu Ile Gln Arg Ile Gly Ser Gly Thr
1               5                   10                  15

Tyr Gly Asp Val Tyr Lys Ala Arg Asn Val Asn Thr Gly Glu Leu Ala
                20                  25                  30

Ala Ile Lys Val Ile Lys Leu Glu Pro Gly Glu Asp Phe Ala Val Val
            35                  40                  45

Gln Gln Glu Ile Ile Met Met Lys Asp Cys Lys His Pro Asn Ile Val
        50                  55                  60

Ala Tyr Phe Gly Ser Tyr Leu Arg Arg Asp Lys Leu Trp Ile Cys Met
65                  70                  75                  80

Glu Phe Cys Gly Gly Gly Ser Leu Gln Asp Ile Tyr His Val Thr Gly
                85                  90                  95

Pro Leu Ser Glu Leu Gln Ile Ala Tyr Val Ser Arg Glu Thr Leu Gln
                100                 105                 110

Gly Leu Tyr Tyr Leu His Ser Lys Gly Lys Met His Arg Asp Ile Lys
            115                 120                 125

Gly Ala Asn Ile Leu Leu Thr Asp Asn Gly His Val Lys Leu Ala Asp
        130                 135                 140

Phe Gly Val Ser Ala Gln Ile Thr Ala Thr Ile Ala Lys Arg Lys Ser
145                 150                 155                 160

Phe Ile Gly Thr Pro Tyr Trp Met Ala Pro Glu Val Ala Ala Val Glu
                165                 170                 175

Arg Lys Gly Gly Tyr Asn Gln Leu Cys Asp Leu Trp Ala Val Gly Ile
                180                 185                 190

Thr Ala Ile Glu Leu Ala Glu Leu Gln Pro Pro Met Phe Asp Leu His
            195                 200                 205

Pro Met Arg Ala Leu Phe Leu Met Thr Lys Ser Asn Phe Gln Pro Pro
        210                 215                 220

Lys Leu Lys Asp Lys Met Lys Trp Ser Asn Ser Phe His His Phe Val
225                 230                 235                 240

Lys Met Ala Leu Thr Lys Asn Pro Lys Lys Arg Pro Thr Ala Glu Lys
                245                 250                 255

Leu Leu Gln His Pro Phe Val Thr Gln His Leu Thr Arg Ser Leu Ala
                260                 265                 270

Ile Glu Leu Leu Asp Lys Val Asn Asn Pro Asp His Ser Thr Tyr His
            275                 280                 285

Asp Phe Asp Asp Asp Asp Pro Glu Pro Leu Val Ala Val Pro His Arg
        290                 295                 300

Ile His Ser Thr Ser Arg Asn Val Arg Glu Glu Lys Thr Arg Ser Glu
305                 310                 315                 320

Ile Thr Phe Gly Gln Val Lys Phe Asp Pro Pro Leu Arg Lys Glu Thr
                325                 330                 335

Glu Pro His His Glu Leu Pro Asp Ser Asp Gly Phe Leu Asp Ser Ser
                340                 345                 350

Glu Glu Ile Tyr Tyr Thr Ala Arg Ser Asn Leu Asp Leu Gln Leu Glu
            355                 360                 365
```

```
Tyr Gly Gln Gly His Gln Gly Gly Tyr Phe Leu Gly Ala Asp Lys Ser
    370             375                 380

Leu Leu Lys Ser Val Glu Glu Leu His Gln Arg Gly His Val Ala
385             390                 395                 400

His Leu Glu Asp Asp Glu Gly Asp Asp Glu Ser Lys His Ser Thr
                405                 410                 415

Leu Lys Ala Lys Ile Pro Pro Leu Pro Pro Lys Pro Lys Ser Ile
                420             425             430

Phe Ile Pro Gln Glu Met His Ser Thr Glu Asp Glu Asn Gln Gly Thr
        435                 440                 445

Ile Lys Arg Cys Pro Met Ser Gly Ser Pro Ala Lys Pro Ser Gln Val
    450                 455                 460

Pro Pro Arg Pro Pro Pro Arg Leu Pro Pro His Lys Pro Val Ala
465             470                 475                 480

Leu Gly Asn Gly Met Ser Ser Phe Gln Leu Asn Gly Glu Arg Asp Gly
                485                 490                 495

Ser Leu Cys Gln Gln Gln Asn Glu His Arg Gly Thr Asn Leu Ser Arg
            500                 505                 510

Lys Glu Lys Lys Asp Val Pro Lys Pro Ile Ser Asn Gly Leu Pro Pro
            515                 520                 525

Thr Pro Lys Val His Met Gly Ala Cys Phe Ser Lys Val Phe Asn Gly
            530                 535                 540

Cys Pro Leu Lys Ile His Cys Ala Ser Ser Trp Ile Asn Pro Asp Thr
545                 550                 555                 560

Arg Asp Gln Tyr Leu Ile Phe Gly Ala Glu Glu Gly Ile Tyr Thr Leu
                565                 570                 575

Asn Leu Asn Glu Leu His Glu Thr Ser Met Glu Gln Leu Phe Pro Arg
            580                 585                 590

Arg Cys Thr Trp Leu Tyr Val Met Asn Asn Cys Leu Leu Ser Ile Ser
            595                 600                 605

Gly Lys Ala Ser Gln Leu Tyr Ser His Asn Leu Pro Gly Leu Phe Asp
            610                 615                 620

Tyr Ala Arg Gln Met Gln Lys Leu Pro Val Ala Ile Pro Ala His Lys
625                 630                 635                 640

Leu Pro Asp Arg Ile Leu Pro Arg Lys Phe Ser Val Ser Ala Lys Ile
                645                 650                 655

Pro Glu Thr Lys Trp Cys Gln Lys Cys Cys Val Val Arg Asn Pro Tyr
                660                 665                 670

Thr Gly His Lys Tyr Leu Cys Gly Ala Leu Gln Thr Ser Ile Val Leu
            675                 680                 685

Leu Glu Trp Val Glu Pro Met Gln Lys Phe Met Leu Ile Lys His Ile
            690                 695                 700

Asp Phe Pro Ile Pro Cys Pro Leu Arg Met Phe Glu Met Leu Val Val
705                 710                 715                 720

Pro Glu Gln Glu Tyr Pro Leu Val Cys Val Gly Val Ser Arg Gly Arg
                725                 730                 735

Asp Phe Asn Gln Val Val Arg Phe Glu Thr Val Asn Pro Asn Ser Thr
            740                 745                 750

Ser Ser Trp Phe Thr Glu Ser Asp Thr Pro Gln Thr Asn Val Thr His
            755                 760                 765

Val Thr Gln Leu Glu Arg Asp Thr Ile Leu Val Cys Leu Asp Cys Cys
770                 775                 780

Ile Lys Ile Val Asn Leu Gln Gly Arg Leu Lys Ser Ser Arg Lys Leu
```

Ser Ser Glu Leu Thr Phe Asp Phe Gln Ile Glu Ser Ile Val Cys Leu
785                 790                 795                 800
            805                 810                 815

Gln Asp Ser Val Leu Ala Phe Trp Lys His Gly Met Gln Gly Arg Ser
            820                 825                 830

Phe Arg Ser Asn Glu Val Thr Gln Glu Ile Ser Asp Ser Thr Arg Ile
            835                 840                 845

Phe Arg Leu Leu Gly Ser Asp Arg Val Val Val Leu Glu Ser Arg Pro
850                 855                 860

Thr Asp Asn Pro Thr Ala Asn Ser Asn Leu Tyr Ile Leu Ala Gly His
865                 870                 875                 880

Glu Asn Ser Tyr

<210> SEQ ID NO 2
<211> LENGTH: 4380
<212> TYPE: DNA
<213> ORGANISM: Homo sapiens

<400> SEQUENCE: 2

```
gaagaagaga tttttaaacaa aaaacgatct aaaaaaattc agaagaaata tgatgaaagg      60
aaaaagaatg ccaaaatcag cagtctcctg gaggagcagt tccagcaggg caagcttctt     120
gcgtgcatcg cttcaaggcc gggacagtgt ggccgagcag atggctatgt tgctagaggg     180
caaagagttg gagttctatc ttaggaaaat caaggccgca aaggcaaata atccttgtt      240 ttgtcttcac ccatgtaata aggtgtttta ttgttttgtt cccaccaaaa aaaaaaaaa      300 aaaaaaaaaa aaaaaaaaaa aaaaaaaaaa aaaaaaaaaa aaaaaaaaaa aaaaaaaacc     360
atggcgcagg aggacttcga gctgattcag cgcatcggca gcggcacccta cggcgacgtc     420 tacaaggcac ggaatgttaa cactggtgaa ttagcagcaa ttaaagtaat aaaattggaa     480
ccaggagaag actttgcagt tgtgcagcaa gaaattatta tgatgaaaga ctgtaaacac     540
ccaaatattg ttgcttattt tggaagctat ctcaggcgag ataagctttg gatttgcatg     600
gagttttgtg gaggtggttc tttacaggat atttatcacg taactggacc tctgtcagaa     660
ctgcaaattg catatgttag cagagaaaca ctgcagggat tatattatct tcacagtaaa     720
ggaaaaatgc acagagatat aaagggagct aacattctat taacggataa tggtcatgtg     780
aaattggctg atttttggagt atctgcacag ataacagcta caattgccaa acggaagtct     840
ttcattggca caccatattg gatggctcca gaagttgcag ctgttgagag aaggggggt      900 tacaatcaac tctgtgatct ctgggcagtg ggaatcactg ccatagaact tgcagagctt     960
cagcctccta tgtttgactt acacccaatg agagcattat ttctaatgac aaaaagcaat    1020
tttcagcctc ctaaactaaa ggataaaatg aaatggtcaa atagttttca tcactttgtg    1080
aaaatggcac ttaccaaaaa tccgaaaaaa agacctactg ctgaaaaatt attacagcat    1140
ccttttgtaa cacaacattt gacacggtct ttggcaatcg agctgttgga taagtaaat    1200 aatccagatc attccactta ccatgatttc gatgatgatg atcctgagcc tcttgttgct    1260
gtaccacata gaattcactc aacaagtaga aacgtgagag aagaaaaaac acgctcagag    1320
ataacctttg gccaagtgaa atttgatcca cccttaagaa aggagacaga accacatcat    1380
gaacttcccg acagtgatgg ttttttggac agttcagaag aaatatacta cactgcaaga    1440
tctaatctgg atctgcaact ggaatatgga caaggacacc aagtggatta cttttttaggt    1500 gcagacaaga gtcttctcaa gtctgttgaa gaagaattgc atcagcgagg acacgtcgca    1560
```

```
catttagaag atgatgaagg agatgatgat gaatctaaac actcaactct gaaagcaaaa    1620
attccacctc ctttgccacc aaagcctaag tctatcttca taccacagga aatgcattct    1680
actgaggatg aaaatcaagg aacaatcaag agatgtccca tgtcagggag cccagcaaag    1740
ccatcccaag ttccacctag accaccacct cccagattac ccccacacaa acctgttgcc    1800
ttaggaaatg gaatgagctc cttccagtta aatggtgaac gagatggctc attatgtcaa    1860
caacagaatg aacatagagg cacaaacctt tcaagaaaag aaaagaaaga tgtaccaaag    1920
cctattagta atggtcttcc tccaacacct aaagtgcata tgggtgcatg ttttttcaaaa   1980 gttttttaatg ggtgtcccctt gaaaattcac tgtgcatcat catggataaa cccagataca   2040
agagatcagt acttgatatt tggtgccgaa gaagggattt ataccctcaa tcttaatgaa    2100
cttcatgaaa catcaatgga acagctattc cctcgaaggt gtacatggtt gtatgtaatg    2160
aacaattgct tgctatcaat atctggtaaa gcttctcagc tttattccca taatttacca    2220 gggcttttttg attatgcaag acaaatgcaa aagttacctg ttgctattcc agcacacaaa    2280
ctccctgaca gaatactgcc aaggaaattt tctgtatcag caaaaatccc tgaaaccaaa    2340
tggtgccaga agtgttgtgt tgtaagaaat ccttacacgg gccataaata cctatgtgga    2400
gcacttcaga ctagcattgt tctattagaa tgggttgaac caatgcagaa atttatgtta    2460
attaagcaca tagattttcc tataccatgt ccacttagaa tgtttgaaat gctggtagtt    2520
cctgaacagg agtacccttt agtttgtgtt ggtgtcagta gaggtagaga cttcaaccaa    2580
gtggttcgat ttgagacggt caatccaaat tctacctctt catggtttac agaatcagat    2640
accccacaga caaatgttac tcatgtaacc caactgggaga gagataccat ccttgtatgc    2700
ttggactgtt gtataaaaat agtaaatctc caaggaagat taaaatctag caggaaattg    2760
tcatcagaac tcacctttga tttccagatt gaatcaatag tgtgcctaca agacagtgtg    2820
ctagctttct ggaaacatgg aatgcaaggt agaagtttta gatctaatga ggtaacacaa    2880
gaaatttcag atagcacaag aattttcagg ctgcttggat ctgacagggt cgtggttttg    2940
gaaagtaggc caactgataa ccccacagca aatagcaatt tgtacatcct ggcgggtcat    3000
gaaaacagtt actgagaatt gttgtgcttt gacagttaac tctagaaaga aagaacacta    3060
ccactgcaac attaatggat gcttgaagct gtacaaaagc tgcagtaacc tgtcttcagt    3120
tactttgtaa tttattgtgg catgagataa gatggggaaa attttgtttt atgtggtatg    3180
gatatattta gcatattgaa ccacacaagt gcttaattca ttgttatgta atctttgtac    3240
atataggcag tattttttct gtgaaacttc atattgctga agacatacac taagaattta    3300
tgtagataat gtacttttat gagatgtaca agtaagtgtc ttatctgtac agatgtaaat    3360
gttgatgaaa atgcaattgg ggttaatatt ttaagaattc tttagtatat tcttgggtgt    3420
ggctatatta caaaatggga tgctggcaat gaaacaatac atttaacact attgtatttt    3480
tattatatgt aatttagtaa tatgaatata atcttgtaa cttttaaaat tgtaatggag    3540
gctgtaatca ttttataatc ttttaatt taatgcaagt acactggtgt ttatatttgc    3600
acaaagtatt gatatgtgat gtattaagtc acaaagtaa gctgtgacat tgtctataag    3660
catttggctc cacaaatgta tttggattgt tttctatgtg aagcaaacca attataatta    3720
accacatgtt gtagtaactg gtcttttttat atttaagcag aatcctgtaa gattgcttgt    3780
ctttgcttaa aaacaatacc tttgaacatt tttgaatcac agaatagcgg taccatgata    3840
gaatactgca attgtggtca gaattacagt atgcacaaag aattaattag cattattaaa    3900
gagtcctcac taaacatttc atatgatcac actgaagaac tgtaacattc catagagtga    3960
```

```
agtggttcaa atttctcttg gaattttac ttttgttggc cttattttat gatccttttc   4020
atatttcttt tgactagag tattaataca tggccaaaat aatttagtta ctacctcata   4080
caaacaatat aatggttact acacatcaca ggaacttagt tttggtttaa gtcatttttg   4140 attgctttt tccaatggaa tatgtatata ccaggtttta gcaaaatgca cacttttggc    4200 tcttttggt atatgttctt tatatttaa tgtgagtata tacactaaga acaaactaaa    4260
ttgtgattta tgatcttcat ttattttaat gataatggtt ttaaaatatg ttcctgattg   4320
tacatattgt aaaataaaca tgttttttaa caaaaaaaaa aagaaaaaa aaaaaaaaaa   4380
```

<210> SEQ ID NO 3
<211> LENGTH: 896
<212> TYPE: PRT
<213> ORGANISM: Rattus norvegicus

<400> SEQUENCE: 3

```
Met Asn Pro Gly Phe Asp Leu Ser Arg Arg Asn Pro Gln Glu Asp Phe
  1               5                  10                  15

Glu Leu Ile Gln Arg Ile Gly Ser Gly Thr Tyr Gly Asp Val Tyr Lys
             20                  25                  30

Ala Arg Asn Val Asn Thr Gly Glu Leu Ala Ala Ile Lys Val Ile Lys
         35                  40                  45

Leu Glu Pro Gly Glu Asp Phe Ala Val Val Gln Gln Glu Ile Ile Met
     50                  55                  60

Met Lys Asp Cys Lys His Pro Asn Ile Val Ala Tyr Phe Gly Ser Tyr
 65                  70                  75                  80

Leu Arg Arg Asp Lys Leu Trp Ile Cys Met Glu Phe Cys Gly Gly Gly
                 85                  90                  95

Ser Leu Gln Asp Ile Tyr His Val Thr Gly Pro Leu Ser Glu Leu Gln
            100                 105                 110

Ile Ala Tyr Val Ser Arg Glu Thr Leu Gln Gly Leu Tyr Tyr Leu His
        115                 120                 125

Ser Lys Gly Lys Met His Arg Asp Ile Lys Gly Ala Asn Ile Leu Leu
    130                 135                 140

Thr Asp Asn Gly His Val Lys Leu Ala Asp Phe Gly Val Ser Ala Gln
145                 150                 155                 160

Ile Thr Ala Thr Ile Ala Lys Arg Lys Ser Phe Ile Gly Thr Pro Tyr
                165                 170                 175

Trp Met Ala Pro Glu Val Ala Ala Val Glu Arg Lys Gly Gly Tyr Asn
            180                 185                 190

Gln Leu Cys Asp Leu Trp Ala Val Gly Ile Thr Ala Ile Glu Leu Ala
        195                 200                 205

Glu Leu Gln Pro Pro Met Phe Asp Leu His Pro Met Arg Ala Leu Phe
    210                 215                 220

Leu Met Thr Lys Ser Asn Phe Gln Pro Pro Lys Leu Lys Asp Lys Leu
225                 230                 235                 240

Lys Trp Ser Asn Ser Phe His His Phe Val Lys Met Ala Leu Thr Lys
                245                 250                 255

Asn Pro Lys Lys Arg Pro Asn Ala Glu Lys Leu Leu Gln His Pro Phe
            260                 265                 270

Val Thr Gln Pro Leu Thr Arg Ser Leu Ala Ile Glu Leu Leu Asp Lys
        275                 280                 285

Val Asn Asn Pro Asp His Ser Thr Tyr His Asp Phe Asp Asp Asp Asp
    290                 295                 300
```

-continued

```
Pro Glu Pro Leu Val Ala Val Pro His Arg Ile Pro Ser Thr Ser Arg
305                 310                 315                 320

Asn Val Arg Glu Glu Lys Thr Arg Ser Glu Ile Asn Phe Gly Gln Val
                325                 330                 335

Lys Phe Asp Pro Pro Leu Arg Lys Glu Thr Glu Pro His His Glu Leu
            340                 345                 350

Pro Asp Ser Asp Gly Phe Phe Asp Ser Ser Glu Glu Ile Tyr Tyr Thr
        355                 360                 365

Ala Arg Ser Asn Leu Asp Leu Gln Leu Glu Tyr Gly Gln Gly His Gln
    370                 375                 380

Ser His Cys Phe Leu Gly Gly Asn Lys Ser Leu Lys Ser Val Glu
385                 390                 395                 400

Glu Glu Leu His Gln Arg Gly His Val Ala His Leu Glu Asp Asp Glu
                405                 410                 415

Gly Asp Asp Asp Ser Lys His Ser Thr Met Lys Ala Lys Val Pro
            420                 425                 430

Pro Pro Leu Pro Pro Lys Pro Lys Ser Ile Phe Ile Pro Gln Asp Thr
        435                 440                 445

His Ser Ala Glu Asp Gly Asn Gln Gly Thr Ile Lys Arg Cys Pro Ser
    450                 455                 460

Ser Gly Ser Pro Ala Lys Pro Ser His Val Pro Pro Arg Pro Pro Pro
465                 470                 475                 480

Pro Arg Leu Pro Pro Gln Lys Pro Ala Val Leu Gly Asn Gly Val Asn
                485                 490                 495

Ser Phe Gln Leu Asn Gly Glu Arg Asp Gly Ser Leu Tyr Gln Gln Gln
            500                 505                 510

Ser Glu Gln Arg Gly Thr Asn Leu Ser Arg Lys Glu Lys Lys Asp Val
        515                 520                 525

Pro Lys Pro Ile Ser Asn Gly Leu Pro Pro Thr Pro Lys Val His Met
    530                 535                 540

Gly Ala Cys Phe Ser Lys Val Phe Asn Gly Cys Pro Leu Lys Ile His
545                 550                 555                 560

Cys Ala Thr Ser Trp Ile Asn Pro Asp Thr Arg Asp Gln Tyr Leu Ile
                565                 570                 575

Phe Gly Ala Glu Glu Gly Ile Tyr Thr Leu Asn Leu Asn Glu Leu His
            580                 585                 590

Glu Thr Ser Met Glu Gln Leu Phe Pro Arg Arg Cys Thr Trp Leu Tyr
        595                 600                 605

Val Met Asn Asn Cys Leu Leu Ser Val Ser Gly Lys Ala Ser Gln Leu
    610                 615                 620

Tyr Ser His Asn Leu Pro Gly Leu Phe Asp Tyr Ala Arg Gln Met Gln
625                 630                 635                 640

Lys Leu Pro Val Ala Ile Pro Ala His Lys Leu Pro Asp Arg Ile Leu
                645                 650                 655

Pro Arg Lys Phe Ala Val Ser Ala Lys Ile Pro Glu Thr Lys Trp Cys
            660                 665                 670

Gln Lys Cys Cys Val Val Arg Asn Pro Tyr Thr Gly His Lys Tyr Leu
        675                 680                 685

Cys Gly Ala Leu Gln Thr Ser Ile Val Leu Leu Glu Trp Val Glu Pro
    690                 695                 700

Met Gln Lys Phe Met Leu Ile Lys His Ile Glu Phe Pro Met Pro Cys
705                 710                 715                 720
```

-continued

```
Pro Leu Arg Met Phe Glu Met Leu Val Val Pro Glu Gln Glu Tyr Pro
                725                 730                 735

Leu Val Cys Val Gly Val Ser Arg Gly Arg Asp Phe Asn Gln Val Val
            740                 745                 750

Arg Phe Glu Thr Val Asn Pro Asn Ser Thr Ser Ser Trp Phe Thr Glu
        755                 760                 765

Ser Gly Ala Asn Ala Pro Gln Thr Ser Val Thr His Val Thr Gln Leu
    770                 775                 780

Glu Arg Asp Thr Ile Leu Val Cys Leu Asp Cys Cys Ile Lys Ile Val
785                 790                 795                 800

Asn Leu Gln Gly Arg Leu Lys Ser Ser Arg Lys Leu Ser Ser Glu Leu
                805                 810                 815

Thr Phe Asp Phe Gln Ile Glu Ser Ile Val Cys Leu Gln Asp Ser Val
            820                 825                 830

Leu Ala Phe Trp Lys His Gly Met Gln Gly Arg Ser Phe Arg Ser Asn
        835                 840                 845

Glu Val Thr Gln Glu Ile Ser Asp Asn Thr Arg Ile Phe Arg Leu Leu
    850                 855                 860

Gly Ser Asp Arg Val Val Val Leu Glu Ser Arg Pro Thr Asp Asn Pro
865                 870                 875                 880

Thr Ala Asn Ser Asn Leu Tyr Ile Leu Ala Gly His Glu Asn Ser Tyr
                885                 890                 895
```

<210> SEQ ID NO 4
<211> LENGTH: 4109
<212> TYPE: DNA
<213> ORGANISM: Rattus norvegicus

<400> SEQUENCE: 4

| | | |
|---|---|---|
| cggccgcggc gtgcagccgg gcgattgtga ccggcggcgg agccgggccg gccgcgggcg | 60 |
| ctccctccgt gcggcccccc tgagcgcccc ccctccccgg gccggagggg aggcgggggg | 120 |
| cacccggggc ccgccatgaa cccgggcttc gacctgtccc gccggaaccc gcaggaggac | 180 |
| ttcgagctga tccaacgcat aggcagcggc acctacggcg acgtctacaa ggcacggaat | 240 |
| gtcaacactg gagaattagc cgcaattaaa gtgataaaat tggaaccagg agaagacttc | 300 |
| gcggttgtac agcaagaaat cattatgatg aaagactgca acatgcaaa catcgttgct | 360 |
| tattttggaa gttatctcag gcgagataaa ctttggattt gcatggaatt ttgtggaggt | 420 |
| ggctctttac aggacatcta tcatgtaact ggccccttt cagagctgca gattgcatac | 480 |
| gttagcaggg aaacactcca gggattgtat ccttcaca gtaaaggaaa aatgcacaga | 540 |
| gatataaagg gcgctaacat cctactaacg ataacggtc atgtgaaatt agctgatttt | 600 |
| ggagtttccg cacagataac agctacaatt gccaaacgga gtccttcat tggtacccca | 660 |
| tattggatgg ccccagaagt cgcggctgtt gagcggaaag gagggtacaa tcagctgtgt | 720 |
| gacctctggg ctgtgggcat cactgccatc gagctggcgg agctccagcc acccatgttt | 780 |
| gaccttcacc caatgagggc attgtttcta atgacaaaaa gcaatttcca gcctcctaaa | 840 |
| ttaaaagata gagttgaagtg gtcaaatagt ttccatcatt ttgtgaagat ggctcttacc | 900 |
| aaaaatccaa aaaaagacc cactgcagaa aagctgctac agcatccctt tgtcacacag | 960 |
| cctctgacga ggtctttggc aatcgagttg ctggacaagg tgaataatcc agatcattcc | 1020 |
| acataccacg actttgacga tgatgaccca gagcctcttg ttgctgtacc acatagaatt | 1080 |
| ccttcaacta gtaggaatgt gagagaagaa aagcacgct cagagataaa ctttggtcag | 1140 |

-continued

```
gtaaaatttg acccgcccttt aaggaaggag acagagccgc atcatgaact tgatctacaa    1200
ttagagtacg ggcaaggaca ccaaagtaat tactttttag gtggaaacaa gagtcttctg    1260
aagtctgttg aagaggagct gcaccagcga ggacacgtgg cacacttaga agatgacgaa    1320
ggggacgatg acgactctaa acattcaacc ttgaaagcaa aagtcccacc tcctctgcca    1380
ccaaagccta atccatctc ataccacag gatacacatt cttctgagga cagtaatcaa    1440
ggcacaatca agagatgtcc ctcatcaggg agcccagcaa agccatccca cgttcctcct    1500
agaccaccac cccccaggct accccgcag aagcctgctg tttttaggcaa tggggtgagc    1560
tccttccagc tcaatggtga acgggacggg tcggtgcatc agcagcagag tgagcagaga    1620
ggcacgaacc tctccagaaa agagaagaag gacgtgccaa agccaattag taatggcctt    1680
cccccaacac ctaaagtgca tatgggagca tgttttttcaa aggttttttaa tggatgtccc    1740
ttgaaaatcc actgtgccac atcttggata aatccggaca cgagagacca gtacttgata    1800
tttggcgctg aagagggcat ttatacccctt aatctcaatg aacttcatga acatcaatg    1860
gaacagctgt tcccccgcag gtgtacgtgg ttgtatgtaa tgaacaactg cttactgtcc    1920
gtatccggca aagcctctca gctttattcc cacaatttac cagggctttt cgattatgca    1980
agacagatgc agaagttacc tgtagccatc ccagcacaca agctcccgga tcgaatactg    2040
cccaggaaat ttgctgtatc agcaaagatt cctgaaacca agtggtgtca gaagtgctgc    2100
gtggtgagaa atccttacac gggccataag tacctgtgcg gagcacttca gactagcatt    2160
gttctattag aatgggttga gccaatgcag aagtttatgt taattaagca catagagttt    2220
ccaatgccgt gtccgctccg gatgttcgag atgctggtgg tgccagagca ggagtaccct    2280
ctggtctgtg ttggcgtcag tagagggcga gacttcaacc aagtggtgcg atttgagacc    2340
gtcaatccaa attctacctc gtcatggttc acagagtcag ataccccgca gacaaacgtc    2400
acccatgtga cccagctgga gagagacacc atcctcgtgt gcttggattg ttgtataaaa    2460
atagtgaatc tccaaggaag attgaaatcc agcagaaaat tatcttcaga gctcaccttc    2520
gatttccaga tagaatccat agtttgtcta caagacagtg tgctagcttt ctggaaacac    2580
gggatgcaag gtagaagttt tagatctaac gaggtaacac aagaaatttc agataacaca    2640
agaatcttca gacttcttgg atctgacagg gttgtggttt tggaaagtag accaactgac    2700
aacccaacag caaatagcaa tttatacatc ctggcgggcc acgaaaacag ctactgacac    2760
tggtgtcgtg acagtgacct gtggagacag ggggccacag ccgctgcaac cttagtggat    2820
ccgcgaagct atgcgggcgc tgcaggaacc tggctctgtt ccttatagtt tactgtggcg    2880
aggcagatgg gagaaggctt tgttttaagt ggtatggatc tgtttagcat attgaacaca    2940
caagtgcttc agccattgtt atgtaatctt tgtacataga agcagtattt ttctgtgaga    3000
cttcatattg ctgaaggcat acactaagga ttgatgtaga taatgtactt tcatgagatg    3060
taaaagtgtc ttatctgtac agatgtaaat gtggattaaa atgcagctgg gttaatattt    3120
taagaattct tagtaaattc ttgggtgtgg tcatattaca gaatgggatg ctggtaatga    3180
aacaagacat ttaacactat cgtattttta ttatatgtaa tttagtaata tggacataaa    3240
tcttgtaact tttaaaatgg taacgagctg taatcatttt ataatcctgt ttttaatttg    3300
aatgcacgtg cactggtgtt tctcctgcac agagtattgc cacgtgatgt gctgtcacag    3360
agaggctgtg acgccagccg tgactacgca tttggtccta caacatcttt tctacgtgta    3420
tttggattgt tttctacgtg aaacaaagcc gttaaccacc tactgtagta actgatcttt    3480
tcctatcaag cagaatcgtg tgcgatagct tgtctgtgct taggacacac ctttgcaaaa    3540
```

-continued

```
cgtaaatcac agaatggcgg taccgtggta gaacactgca gctgtcgcca gggcgacagt    3600
gtgcacagga gagactggca ctgctgagga ctccacacta gacatttcag tcacactgaa    3660
gagccgtcac attccacagt gacatggtcg cgttttttcat ggacttttac ttctgttggc   3720
cttattttat tatgacttcc atatttcttt ttatttagag tattaataca tggccaaaat    3780
aatttagtta ctacctcata cagacatcat aatggttact acagatcaca ggaagttagt    3840
ttggttaaaa tcattattga tgggttttc caatggagtg tatctgtctt accaagatcg     3900
atggcaaggt gtagcgaagc gcacgcctct gactctggta tacgttcatg tgttctttat    3960
attttgatgt gagtatgtat acactaagaa caagctaaat tgtggtttat gcttcattta    4020
ttttaactga taatggtttt aaatacgttc ctgattgtac atactgtaaa ataaacatgt    4080
tttttaacat gcaaaaaaaa aaaaaaaaa                                      4109
```

<210> SEQ ID NO 5
<211> LENGTH: 706
<212> TYPE: PRT
<213> ORGANISM: Homo sapiens

<400> SEQUENCE: 5

```
Met Ser Pro Phe Leu Arg Ile Gly Leu Ser Asn Phe Asp Cys Gly Ser
1               5                   10                  15

Cys Gln Ser Cys Gln Gly Glu Ala Val Asn Pro Tyr Cys Ala Val Leu
            20                  25                  30

Val Lys Glu Tyr Val Glu Ser Glu Asn Gly Gln Met Tyr Ile Gln Lys
        35                  40                  45

Lys Pro Thr Met Tyr Pro Pro Trp Asp Ser Thr Phe Asp Ala His Ile
    50                  55                  60

Asn Lys Gly Arg Val Met Gln Ile Ile Val Lys Gly Lys Asn Val Asp
65                  70                  75                  80

Leu Ile Ser Glu Thr Thr Val Glu Leu Tyr Ser Leu Ala Glu Arg Cys
                85                  90                  95

Arg Lys Asn Asn Gly Lys Thr Glu Ile Trp Leu Glu Leu Lys Pro Gln
            100                 105                 110

Gly Arg Met Leu Met Asn Ala Arg Tyr Phe Leu Glu Met Ser Asp Thr
        115                 120                 125

Lys Asp Met Asn Glu Phe Glu Thr Glu Gly Phe Phe Ala Leu His Gln
    130                 135                 140

Arg Arg Gly Ala Ile Lys Gln Ala Lys Val His His Val Lys Cys His
145                 150                 155                 160

Glu Phe Thr Ala Thr Phe Phe Pro Gln Pro Thr Phe Cys Ser Val Cys
                165                 170                 175

His Glu Phe Val Trp Gly Leu Asn Lys Gln Gly Tyr Gln Cys Arg Gln
            180                 185                 190

Cys Asn Ala Ala Ile His Lys Lys Cys Ile Asp Lys Val Ile Ala Lys
        195                 200                 205

Cys Thr Gly Ser Ala Ile Asn Ser Arg Glu Thr Met Phe His Lys Glu
    210                 215                 220

Arg Phe Lys Ile Asp Met Pro His Arg Phe Lys Val Tyr Asn Tyr Lys
225                 230                 235                 240

Ser Pro Thr Phe Cys Glu His Cys Gly Thr Leu Leu Trp Gly Leu Ala
                245                 250                 255

Arg Gln Gly Leu Lys Cys Asp Ala Cys Gly Met Asn Val His His Arg
            260                 265                 270
```

-continued

```
Cys Gln Thr Lys Val Ala Asn Leu Cys Gly Ile Asn Gln Lys Leu Met
        275                 280                 285
Ala Glu Ala Leu Ala Met Ile Glu Ser Thr Gln Gln Ala Arg Cys Leu
    290                 295                 300
Arg Asp Thr Glu Gln Ile Phe Arg Glu Gly Pro Val Glu Ile Gly Leu
305                 310                 315                 320
Pro Cys Ser Ile Lys Asn Glu Ala Arg Pro Pro Cys Leu Pro Thr Pro
                325                 330                 335
Gly Lys Arg Glu Pro Gln Gly Ile Ser Trp Glu Ser Pro Leu Asp Glu
            340                 345                 350
Val Asp Lys Met Cys His Leu Pro Glu Pro Glu Leu Asn Lys Glu Arg
        355                 360                 365
Pro Ser Leu Gln Ile Lys Leu Lys Ile Glu Asp Phe Ile Leu His Lys
    370                 375                 380
Met Leu Gly Lys Gly Ser Phe Gly Lys Val Phe Leu Ala Glu Phe Lys
385                 390                 395                 400
Lys Thr Asn Gln Phe Phe Ala Ile Lys Ala Leu Lys Lys Asp Val Val
                405                 410                 415
Leu Met Asp Asp Asp Val Glu Cys Thr Met Val Glu Lys Arg Val Leu
            420                 425                 430
Ser Leu Ala Trp Glu His Pro Phe Leu Thr His Met Phe Cys Thr Phe
        435                 440                 445
Gln Thr Lys Glu Asn Leu Phe Phe Val Met Glu Tyr Leu Asn Gly Gly
    450                 455                 460
Asp Leu Met Tyr His Ile Gln Ser Cys His Lys Phe Asp Leu Ser Arg
465                 470                 475                 480
Ala Thr Phe Tyr Ala Ala Glu Ile Ile Leu Gly Leu Gln Phe Leu His
                485                 490                 495
Ser Lys Gly Ile Val Tyr Arg Asp Leu Lys Leu Asp Asn Ile Leu Leu
            500                 505                 510
Asp Lys Asp Gly His Ile Lys Ile Ala Asp Phe Gly Met Cys Lys Glu
        515                 520                 525
Asn Met Leu Gly Asp Ala Lys Thr Asn Thr Phe Cys Gly Thr Pro Asp
    530                 535                 540
Tyr Ile Ala Pro Glu Ile Leu Leu Gly Gln Lys Tyr Asn His Ser Val
545                 550                 555                 560
Asp Trp Trp Ser Phe Gly Val Leu Leu Tyr Glu Met Leu Ile Gly Gln
                565                 570                 575
Ser Pro Phe His Gly Gln Asp Glu Glu Glu Leu Phe His Ser Ile Arg
            580                 585                 590
Met Asp Asn Pro Phe Tyr Pro Arg Trp Leu Glu Lys Glu Ala Lys Asp
        595                 600                 605
Leu Leu Val Lys Leu Phe Val Arg Glu Pro Glu Lys Arg Leu Gly Val
    610                 615                 620
Arg Gly Asp Ile Arg Gln His Pro Leu Phe Arg Glu Ile Asn Trp Glu
625                 630                 635                 640
Glu Leu Glu Arg Lys Glu Ile Asp Pro Pro Phe Arg Pro Lys Val Lys
                645                 650                 655
Ser Pro Phe Asp Cys Ser Asn Phe Asp Lys Glu Phe Leu Asn Glu Lys
            660                 665                 670
Pro Arg Leu Ser Phe Ala Asp Arg Ala Leu Ile Asn Ser Met Asp Gln
        675                 680                 685
```

```
Asn Met Phe Arg Asn Phe Ser Phe Met Asn Pro Gly Met Glu Arg Leu
    690                 695                 700

Ile Ser
705
```

<210> SEQ ID NO 6
<211> LENGTH: 3273
<212> TYPE: DNA
<213> ORGANISM: Homo sapiens

<400> SEQUENCE: 6

```
agtccccgcg cagtccccgc gcagtcccag cgccaccggg cagcagcggc gccgtgctcg     60
ctccagggcg caaccatgtc gccatttctt cggattggct tgtccaactt tgactgcggg    120
tcctgccagt cttgtcaggg cgaggctgtt aacccttact gtgctgtgct cgtcaaagag    180
tatgtcgaat cagagaacgg gcagatgtat atccagaaaa agcctaccat gtacccaccc    240
tgggacagca cttttgatgc ccatatcaac aagggaagag tcatgcagat cattgtgaaa    300
ggcaaaaacg tggacctcat ctctgaaacc accgtggagc tctactcgct ggctgagagg    360
tgcaggaaga caacgggaa gacagaaata tggttagagc tgaaacctca aggccgaatg    420
ctaatgaatg caagatactt tctggaaatg agtgacacaa aggacatgaa tgaatttgag    480
acggaaggct tctttgcttt gcatcagcgc cggggtgcca tcaagcaggc aaaggtccac    540
cacgtcaagt gccacgagtt cactgccacc ttcttcccac agcccacatt ttgctctgtc    600
tgccacgagt ttgtctgggg cctgaacaaa cagggctacc agtgccgaca atgcaatgca    660
gcaattcaca gaagtgtat tgataaagtt atagcaaagt gcacaggatc agctatcaat    720
agccgagaaa ccatgttcca caggagaga ttcaaaattg acatgccaca cagatttaaa    780
gtctacaatt acaagagccc gaccttctgt gaacactgtg ggaccctgct gtggggactg    840
gcacggcaag gactcaagtg tgatgcatgt ggcatgaatg tgcatcatag atgccagaca    900
aaggtggcca acctttgtgg cataaaccag aagctaatgg ctgaagcgct ggccatgatt    960
gagagcactc aacaggctcg ctgcttaaga gatactgaac agatcttcag agaaggtccg   1020
gttgaaattg gtctcccatg ctccatcaaa aatgaagcaa ggccgccatg tttaccgaca   1080
ccgggaaaaa gagagcctca gggcattttcc tgggagtctc cgttggatga ggtggataaa   1140
atgtgccatc ttccagaacc tgaactgaac aaagaaagac catctctgca gattaaacta   1200
aaaattgagg attttatctt gcacaaaatg ttggggaaag aagttttgg caaggtcttc   1260
ctggcagaat tcaagaaaac caatcaattt tcgcaataa aggccttaaa gaaagatgtg   1320
gtcttgatgg acgatgatgt tgagtgcacg atggtagaga agagagttct ttccttggcc   1380
tgggagcatc cgtttctgac gcacatgttt tgtacattcc agaccaagga aaacctcttt   1440
tttgtgatgg agtacctcaa cggaggggac ttaatgtacc acatccaaag ctgccacaag   1500
ttcgaccttt ccagagcgac gttttatgct gctgaaatca ttcttggtct gcagttcctt   1560
cattccaaag gaatagtcta cagggacctg aagctagata acatcctgtt agacaaagat   1620
ggacatatca gatcgcgga ttttggaatg tgcaaggaga acatgttagg agatgccaag   1680
acgaatacct tctgtgggac acctgactac atcgccccag atcttgct gggtcagaaa   1740
tacaaccact ctgtggactg gtggtccttc ggggttctcc tttatgaaat gctgattggt   1800
cagtcgcctt tccacgggca ggatgaggag gagctcttcc actccatccg catggacaat   1860
ccctttacc acggtggct ggagaaggaa gcaaggacc ttctggtgaa gctcttcgtg   1920
cgagaacctg agaagaggct gggcgtgagg ggagacatcc gccagcaccc tttgtttcgg   1980
```

```
gagatcaact gggaggaact tgaacggaag gagattgacc caccgttccg gccgaaagtg   2040
aaatcaccat ttgactgcag caatttcgac aaagaattct taaacgagaa gccccggctg   2100
tcatttgccg acagagcact gatcaacagc atggaccaga atatgttcag gaacttttcc   2160
ttcatgaacc ccgggatgga gcggctgata tcctgaatct tgcccctcca gagacaggaa   2220
agaatttgcc ttctccctgg gaactggttc aagagacact gcttgggttc cttttttcaac  2280 ttggaaaaag aaagaaacac tcaacaataa agactgagac ccgttcgccc ccatgtgact   2340
tttatctgta gcagaaacca agtctacttc actaatgacg atgccgtgtg tctcgtctcc   2400
tgacatgtct cacagacgct cctgaagtta ggtcattact aaccatagtt atttacttga   2460
aagatgggtc tccgcacttg aaaggtttc aagacttgat actgcaataa attatggctc    2520
ttcacctggg cgccaactgc tgatcaatga aatgcttgtt gaatcagggg caaacggagt   2580
acagacgtct caagactgaa acggccccat tgcctggtct agtagcggat ctcactcagc   2640
cgcagacaag taatcactaa cccgttttat tctattccta tctgtggatg tgtaaatggc   2700 tgggggggcca gccctggata ggttttttatg ggaattcttt acaataaaca tagcttgtaa  2760
cttgagatct acaaatccat tcatcctgat tgggcatgaa atccatggtc aagaggacaa   2820
gtggaaagtg agagggaagg tttgctagac accttcgctt gttatcttgt caagatagaa   2880
aagatagtat catttcaccc ttgccagtaa aaacctttcc atccacccat tctcagcaga   2940
ctccagtatt ggcacagtca ctcactgcca ttctcacact ataacaagaa agaaatgaa    3000 gtgcataagt ctcctgggaa aagaaccta accccttctc gtgccatgac tggtgatttc    3060
atgactcata agcccctccg taggcatcat tcaagatcaa tggcccatgc atgctgtttg   3120
cagcagtcaa ttgagttgaa ttagaattcc aaccatacat tttaaaggta tttgtgctgt   3180
gtgtatattt tgataaaatg ttgtgacttc atggcaaaca ggtggatgtg taaaaatgga   3240
ataaaaaaaa aaaagagtc aaaaaaaaaa aaa                                 3273

<210> SEQ ID NO 7
<211> LENGTH: 707
<212> TYPE: PRT
<213> ORGANISM: Mus musculus

<400> SEQUENCE: 7

Met Ser Pro Phe Leu Arg Ile Gly Leu Ser Asn Phe Asp Cys Gly Thr
1               5                   10                  15

Cys Gln Ala Cys Gln Gly Glu Ala Val Asn Pro Tyr Cys Ala Val Leu
            20                  25                  30

Val Lys Glu Tyr Val Glu Ser Glu Asn Gly Gln Met Tyr Ile Gln Lys
        35                  40                  45

Lys Pro Thr Met Tyr Pro Pro Trp Asp Ser Thr Phe Asp Ala His Ile
    50                  55                  60

Asn Lys Gly Arg Val Met Gln Ile Ile Val Lys Gly Lys Asn Val Asp
65                  70                  75                  80

Leu Ile Ser Glu Thr Thr Val Glu Leu Tyr Ser Leu Ala Glu Arg Cys
                85                  90                  95

Arg Lys Asn Asn Gly Arg Thr Glu Ile Trp Leu Glu Leu Lys Pro Gln
            100                 105                 110

Gly Arg Met Leu Met Asn Ala Arg Tyr Phe Leu Glu Met Ser Asp Thr
        115                 120                 125

Lys Asp Met Ser Glu Phe Glu Asn Glu Gly Phe Phe Ala Leu His Gln
    130                 135                 140
```

```
Arg Arg Gly Ala Ile Lys Gln Ala Lys Val His His Val Lys Cys His
145                 150                 155                 160

Glu Phe Thr Ala Thr Phe Phe Pro Gln Pro Thr Phe Cys Ser Val Cys
                165                 170                 175

His Glu Phe Val Trp Gly Leu Asn Lys Gln Gly Tyr Gln Cys Arg Gln
            180                 185                 190

Cys Asn Ala Ala Ile His Lys Lys Cys Ile Asp Lys Val Ile Ala Lys
        195                 200                 205

Cys Thr Gly Ser Ala Ile Asn Ser Arg Glu Thr Met Phe His Lys Glu
210                 215                 220

Arg Phe Lys Ile Asp Met Pro His Arg Phe Lys Val Tyr Asn Tyr Lys
225                 230                 235                 240

Ser Pro Thr Phe Cys Glu His Cys Gly Thr Leu Leu Trp Gly Leu Ala
                245                 250                 255

Arg Gln Gly Leu Lys Cys Asp Ala Cys Gly Met Asn Val His His Arg
            260                 265                 270

Cys Gln Thr Lys Val Ala Asn Leu Cys Gly Ile Asn Gln Lys Leu Met
        275                 280                 285

Ala Glu Ala Leu Ala Met Ile Glu Ser Thr Gln Gln Ala Arg Ser Leu
290                 295                 300

Arg Asp Ser Glu His Ile Phe Arg Glu Gly Pro Val Glu Ile Gly Leu
305                 310                 315                 320

Pro Cys Ser Thr Lys Asn Glu Thr Arg Pro Pro Cys Val Pro Thr Pro
                325                 330                 335

Gly Lys Arg Glu Pro Gln Gly Ile Ser Trp Asp Ser Pro Leu Asp Gly
            340                 345                 350

Ser Asn Lys Ser Ala Gly Pro Pro Glu Pro Glu Val Ser Met Arg Arg
        355                 360                 365

Thr Ser Leu Gln Leu Lys Leu Lys Ile Asp Asp Phe Ile Leu His Lys
370                 375                 380

Met Leu Gly Lys Gly Ser Phe Gly Lys Val Phe Leu Ala Glu Phe Lys
385                 390                 395                 400

Arg Thr Asn Gln Phe Phe Ala Ile Lys Ala Leu Lys Lys Asp Val Val
                405                 410                 415

Leu Met Asp Asp Asp Val Glu Cys Thr Met Val Glu Lys Arg Val Leu
            420                 425                 430

Ser Leu Ala Trp Glu His Pro Phe Leu Thr His Met Phe Cys Thr Phe
        435                 440                 445

Gln Thr Lys Glu Asn Leu Phe Phe Val Met Glu Tyr Leu Asn Gly Gly
450                 455                 460

Asp Leu Met Tyr His Ile Gln Ser Cys His Lys Phe Asp Leu Ser Arg
465                 470                 475                 480

Ala Thr Phe Tyr Ala Ala Glu Val Ile Leu Gly Leu Gln Phe Leu His
                485                 490                 495

Ser Lys Gly Ile Val Tyr Arg Asp Leu Lys Leu Asp Asn Ile Leu Leu
            500                 505                 510

Asp Arg Asp Gly His Ile Lys Ile Ala Asp Phe Gly Met Cys Lys Glu
        515                 520                 525

Asn Met Leu Gly Asp Ala Lys Thr Asn Thr Phe Cys Gly Thr Pro Asp
530                 535                 540

Tyr Ile Ala Pro Glu Ile Leu Leu Gly Gln Lys Tyr Asn His Ser Val
545                 550                 555                 560
```

```
Asp Trp Trp Ser Phe Gly Val Leu Val Tyr Glu Met Leu Ile Gly Gln
                565                 570                 575

Ser Pro Phe His Gly Gln Asp Glu Glu Glu Leu Phe His Ser Ile Arg
            580                 585                 590

Met Asp Asn Pro Phe Tyr Pro Arg Trp Leu Glu Arg Glu Ala Lys Asp
        595                 600                 605

Leu Leu Val Lys Leu Phe Val Arg Glu Pro Glu Lys Arg Leu Gly Val
    610                 615                 620

Arg Gly Asp Ile Arg Gln His Pro Leu Phe Arg Glu Ile Asn Trp Glu
625                 630                 635                 640

Glu Leu Glu Arg Lys Glu Ile Asp Pro Pro Phe Arg Pro Lys Val Lys
                645                 650                 655

Ser Pro Tyr Asp Cys Ser Asn Phe Asp Lys Glu Phe Leu Ser Glu Lys
            660                 665                 670

Pro Arg Leu Ser Phe Ala Asp Arg Ala Leu Ile Asn Ser Met Asp Gln
        675                 680                 685

Asn Met Phe Ser Asn Phe Ser Phe Ile Asn Pro Gly Met Glu Thr Leu
    690                 695                 700

Ile Cys Ser
705

<210> SEQ ID NO 8
<211> LENGTH: 2150
<212> TYPE: DNA
<213> ORGANISM: Mus musculus

<400> SEQUENCE: 8
gcgacaccag gaacaacca tgtcaccgtt tcttcgaatc ggtttatcca actttgactg      60
tgggacctgc caagcttgtc agggagaggc agtgaacccc tactgcgctg tgcttgtcaa     120
agagtatgtg gaatcagaaa atgggcagat gtacatccag aaaaagccaa ccatgtaccc     180
accttgggac agcacctttg acgcccacat taacaaggga agggtgatgc agatcatcgt     240
gaagggcaag aatgtagacc tcatctcaga acaaccgtg gaactctact ccctggcgga      300
gagatgccgc aagaacaatg gcggacagaa atatggttta gagctgaaac tcaaggccg      360 aatgctaatg aatgcaagat actttctgga aatgagtgac acaaaggaca tgagtgagtt     420
tgagaatgaa ggattctttg cactgcatca gcgccgagga gccatcaaac aggccaaagt     480
ccaccatgtc aagtgtcacg agttcacggc cacctttttc cctcaaccca cattttgctc     540
tgtctgccat gaatttgtct ggggcctgaa caagcagggt taccagtgcc gacagtgtaa     600
tgcagcgatt cacaagaagt gcattgataa agtgatagcc aagtgcacag atccgcaat      660 caatagccga gaaccatgt tccataagga gagattcaag atcgacatgc cacagagatt      720
caaagtctac aactacaaga gtccaacctt ctgtgagcac tgtggtaccc tgctctgggg     780
gctggcgagg caaggactca atgtgatgc atgtggcatg aacgtccacc accgatgcca     840
gacaaaggtt gccaatcttt gtggtataaa ccagaagcta atggctgaag cactagcgat     900
gattgaaagc acccaacagg ctcgctcctt acgagattca gaacacatct tccgagaagg     960
cccagttgaa attggtctcc catgctccac caaaacgaa accaggccac catgcgtacc     1020
aacacctggg aaaagagaac cccagggcat ttcctgggat tccccctttgg atgggtcaaa    1080 taaatcggcc ggtcctcctg aacccgaagt gagcatgcgc aggacttcac tgcagctgaa    1140
actgaagatc gatgacttca tcctgcacaa gatgttggga aaggaagtt ttggcaaggt     1200 cttcctggca gagttcaaga gaaccaatca gttttttcgca ataaaagcct aaagaaaga    1260
```

-continued

```
tgtggtgttg atggatgatg acgtcgagtg tacaatggtg gaaaagaggg ttctgtcctt    1320
ggcatgggag catccatttc taacacacat gttctgcaca ttccagacca aggaaaatct    1380 cttttcgtg atggagtatc tcaatggagg cgacttaatg taccacatcc aaagttgcca     1440
caaatttgat ctttccagag ccacgtttta tgctgctgag gtcatccttg gtctgcagtt    1500
ccttcattcc aaaggaattg tctacaggga cctgaagctt gataatatcc tgttagacag    1560
agatggacat atcaaaatag cagactttgg gatgtgcaaa gagaacatgc taggagatgc    1620
gaagacaaat actttctgtg gaactcctga ctacattgct ccggagatct tgctgggtca    1680
gaagtacaac cattccgtcg actggtggtc cttcggggtg ctcgtttatg agatgctgat    1740
tggccagtcc cccttccacg ggcaggacga ggaggagctg ttccactcca tccgcatgga    1800 caacccttc tacccgaggt ggctcgaaag ggaggccaag gaccttctag tgaagctttt    1860
tgtgagagaa cctgagaaga ggctgggagt gagaggagac atccgccagc atcctttgtt    1920
tcgagagatc aactgggaag agcttgaaag gaaagagatt gacccaccct tcagaccaaa    1980
agtgaaatca ccatatgact gtagcaattt cgacaaggaa ttcctaagtg agaaacccg     2040 gctatcattc gccgacagag cactcatcaa cagcatggac cagaacatgt tcagcaactt    2100
ttccttcatt aacccaggga tggagactct catttgctcc tgaacctcat                2150
```

MAP KINASE KINASE KINASE KINASE 3 (MAP4K3) AS A BIOMARKER AND THERAPEUTIC TARGET FOR AUTOIMMUNE DISEASE, CANCER, INFLAMMATION AND IL-17-ASSOCIATED DISEASE

REFERENCE TO RELATED APPLICATION

The present application claims the priority to U.S. Provisional Application Ser. No. 61/508,057, filed Jul. 14, 2011, which is herein incorporated by reference in its entirety.

FIELD OF THE INVENTION

The present invention relates generally to an to immunity and cancer, and more specifically to modulations of autoimmunity and PKC/NF-κB signaling, as well as tumor metastasis.

BACKGROUND OF THE INVENTION

NF-κB is a major transcription factor that regulates genes responsible for cell survival, growth and proliferation. T cell receptor (TCR) engagement induces NF-κB activation, which is involved in the host defence against infection and the development of inflammation, cancer and autoimmunity. PKC-θ plays a critical role in IKK-NF-κB activation and T cell function. The adaptor SLP-76 is required for PKC-θ activation upon TCR stimulation. However, the signal transduction from SLP-76 to PKC-θ and the direct kinase activating PKC-θ remain unclear. Thus, the most critical question in TCR-induced NF-κB activation is to identify the pivotal link between SLP-76 and PKC-0.

PKC-θ activation requires its phosphorylation at T538. The kinase PDK1 interacts with PKC-θ and phosphorylation of PKC-θ at T538 is defective in PDK1-deficient T cells. Thus, PDK1 has been proposed to directly phosphorylate PKC-θ at T538, although no clear evidence exists that PDK1 directly phosphorylates PKC-θ in vitro. Furthermore, the observation that PDK1 can be activated only by CD28, but not TCR signaling, further rules out the possibility that PDK1 is the direct kinase for PKC-θ activation induced by TCR signaling. Thus, the kinase that directly activates PKC-θ during T cell activation remains elusive.

GCK-like kinase (GLK; also named MAP4K3) is a member of MAP kinase kinase kinase kinase (MAP4K), which is a subfamily of Ste20-like serine/threonine kinases. GLK contains a conserved N-terminal kinase domain, a conserved C-terminal citron homology domain and several proline-rich motifs in the middle. Jnk phosphorylation is induced by GLK through MEKKI and MKK4/SEK1 in response to stress stimulation. GLK also regulates cell growth via activating the mTOR downstream effectors S6K1 and 4E-BP1 in epithelial cell lines after amino acid treatment. However, the regulatory mechanism and physiological roles of GLK are largely unknown.

Therefore, a heretofore unaddressed need exists in the art to address the aforementioned deficiencies and inadequacies related to regulation of GLK, especially in connection with the physiological role of GLK in the TCR signaling process.

SUMMARY OF THE INVENTION

In one aspect, the invention relates to a method for identifying a therapeutic agent for treating a Germinal Center Kinase (GCK)-Like Kinase (GLK)-mediated disease. The method comprises detecting a modulation of GLK-mediated signal transduction by a test compound, in which the detecting step comprises: a) culturing GLK-expressing cells in the presence of the test compound, wherein said modulation is detected by measuring the expression level of GLK transcripts or protein, the amount of IL-17A produced or the activity of NF-κb; or b) allowing a GLK protein to react at the presence of ATP with a substrate thereof in the presence of the test compound, wherein said modulation is detected by measuring the amount of ADP produced, the amount of ATP consumed and/or the amount of the substrate being phosphorylated; or c) culturing GLK-expressing cancer cells in the presence of the test compound, wherein the modulation is detected by measuring migration/invasion/wound healing of said cancer cells; or d) allowing a GLK protein to interact with a substrate protein thereof in the presence of the test compound, wherein said modulation is detected by measuring the interaction between the GLK and the substrate protein; and e) comparing said modulation in the presence of the test compound with a control identifies a therapeutic agent for treating a GLK-mediated disease.

In another aspect, the invention relates to a method for detecting the presence and/or severity of a Germinal Center Kinase (GCK)-Like Kinase (GLK)-mediated disease. Detecting the presence and/or severity of GLK-mediated disease may comprise determining the prognosis of a cancer. The method comprises: a) obtaining a sample comprising T cells or cancer cells from a subject suspected of having a GLK-mediated disease or cancer; b) measuring the expression level of GCK-like kinase (GLK) in the T cells or cancer cells; and c) determining the presence and/or severity of the GLK-mediated disease; wherein an increase in the expression level of GLK in the T cells or cancer cells as compared with the expression level of GLK in a control is an indication that the subject is at risk of developing or having the GLK-mediated disease, or at risk of recurrence and/or metastasis of the cancer. The determining step may comprise determining the prognosis of the cancer.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

Immunoblot analyses of GLK expression and GLK-induced PKC-θ phosphorylation in in vitro kinase assays using purified Flag-GLK and GST-PKC-θ proteins. Data are representative of three independent experiments.

Figure 2:
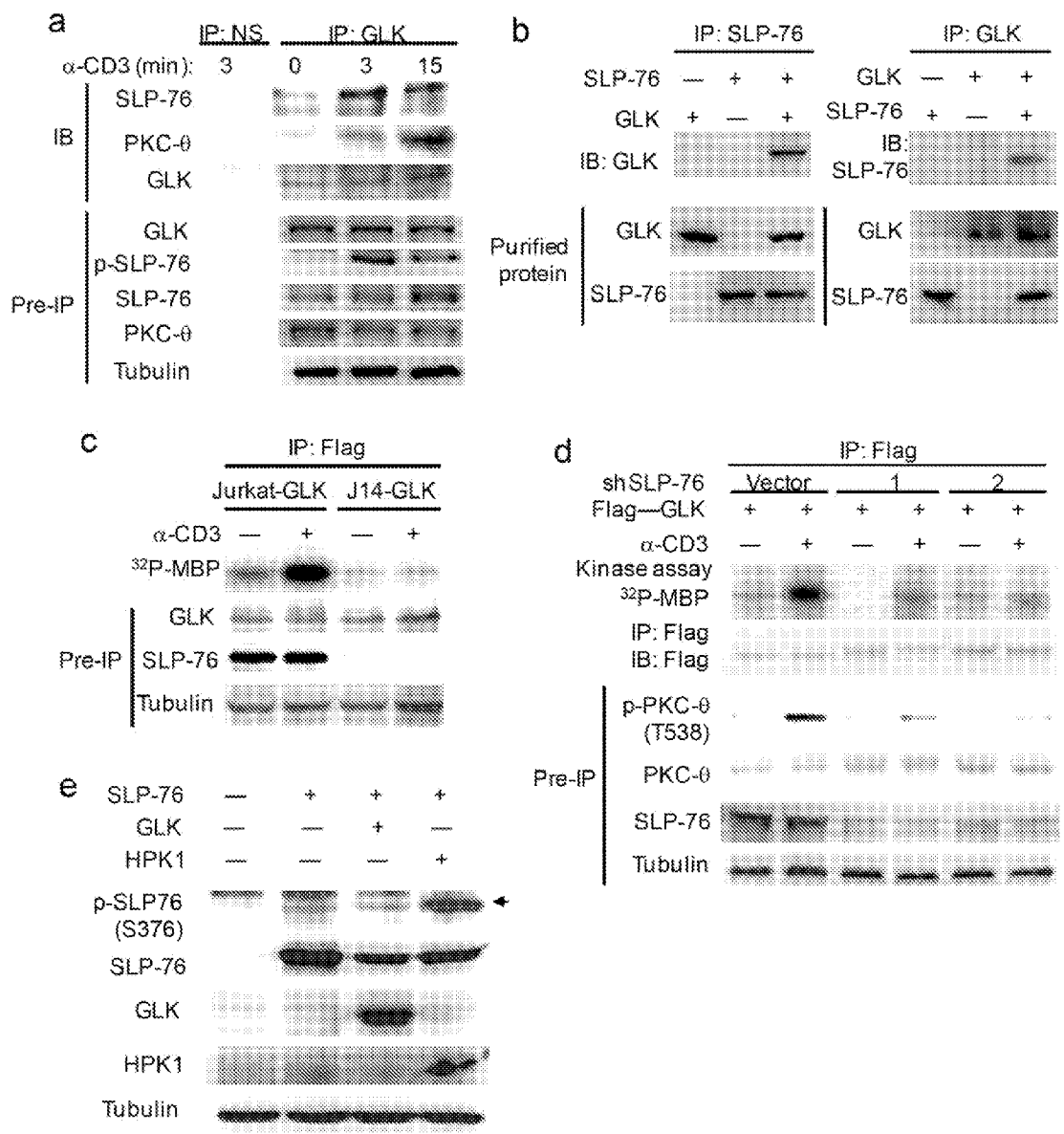

FIG. 2 shows that SLP-76 is a direct upstream regulator of GLK. (a) Co-immunoprecipitations of endogenous GLK with SLP-76 or PKC-θ in lysates of mouse primary T cells following CD3 stimulation, (b) In vitro binding assays of purified Flag-GLK and Flag-SLP-76 proteins, (c.d) In vitro kinase assays of Flag-GLK in lysates of J14 cells (c) or Jurkat T cells (d) transfected with empty vector or plasmid encoding of GLK, with or without SLP-76 shRNAs (d), then left untreated or treated with anti-CD3 antibody (e) Immunoblot analyses of the phosphorylation of SLP-76 S376 in lysates of HEK293T cells transfected with empty vector or plasmid encoding SLP-76 plus plasmid encoding GLK or HPK1. Arrow, phosphorylation of SLP-76 S376. Data are representative of three independent experiments.

Figure 3:
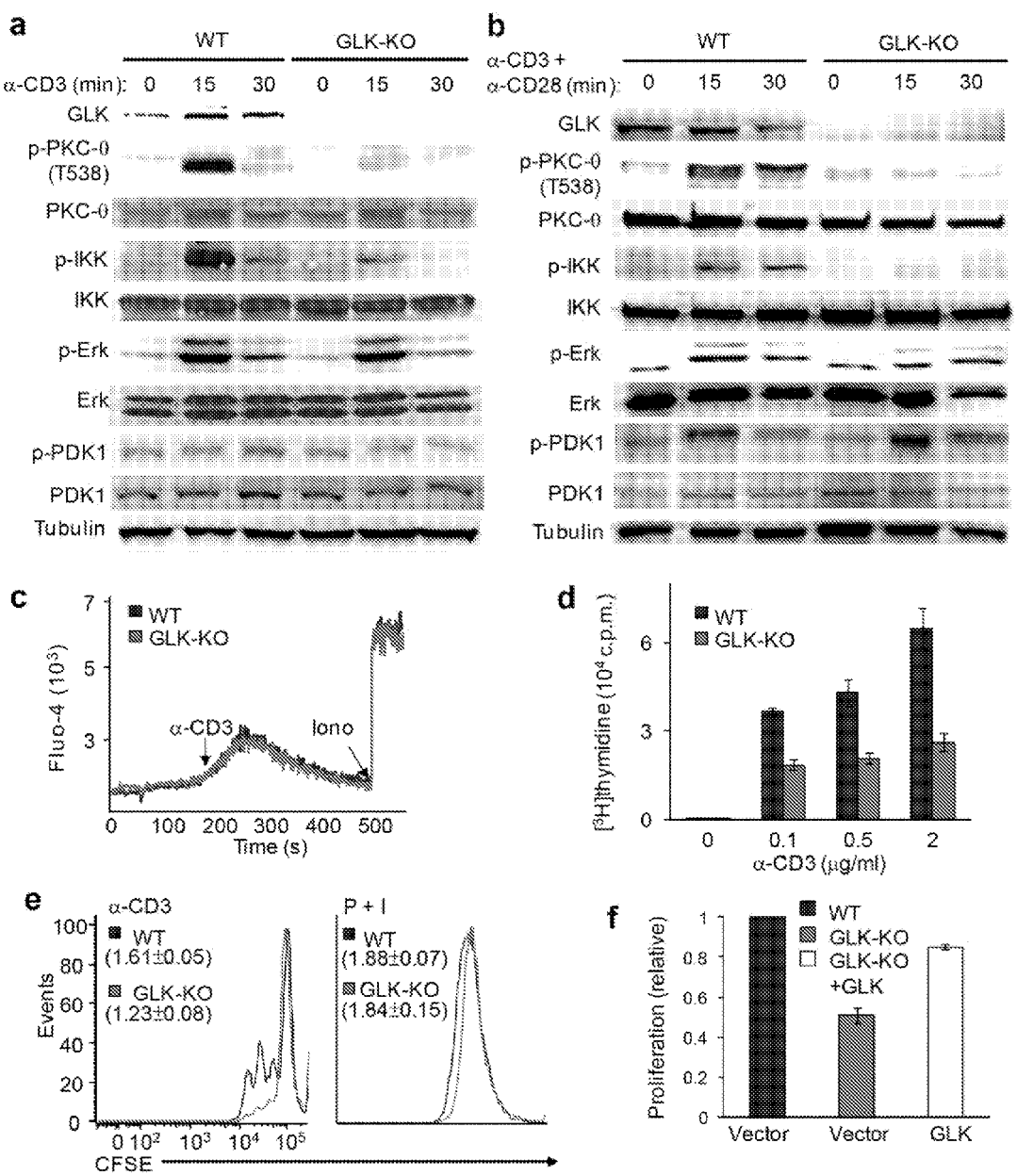

FIG. 3 shows that GLK-deficient primary T cells are defective in PKC-θ-IKK activation and T cell proliferation. (a,b) Immunoblot analyses of GLK, p-PKC-θ, PKC-θ, IKK, p-Erk, Erk, p-PDK1, PDK1 and tubulin in lysates of purified T cells following CD3 (a) or CD3 plus CD28 (b) stimulation, (c) Flow cytometry of calcium indicators Fluo-4 in purified mouse T cells stimulated with anti-CD3 antibody and then ionomycin (Iono). (d,e) [$^3$H]thymidine incorporation assays (d) and CFSE profiles (e) of CD3$^+$ T cells isolated from wild-type or GLK-deficient mice treated with anti-CD3 antibody or PMA plus ionomycin for 72 h. Proliferation indexes (mean±s.e.m) analyzed by FlowJo software are shown, (f) [$^3$H]thymidine incorporation assays in wild-type and GLK-deficient T cells transfected with empty vector (pCMV-GFP) or GFP-GLK. WT, wild-type; GLK-KO, GLK-deficient mice. Data are representative of three independent experiments (error bars (d,f), s.e.m.).

Figure 4:
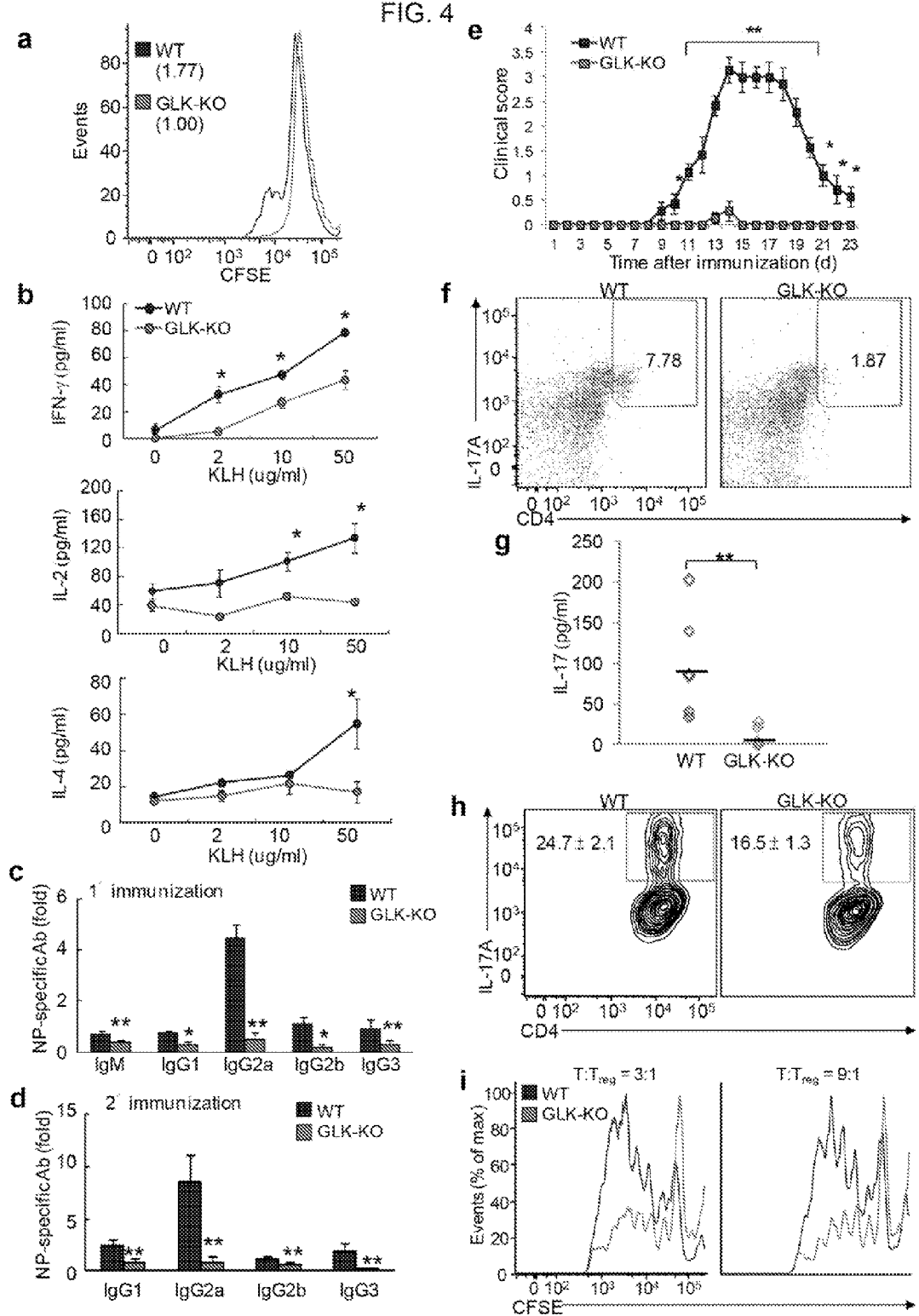

FIG. 4 shows that in vivo T cell-dependent immune responses are impaired in GLK-deficient mice. (a,b) CFSE dilution assays (a) and ELISA assays of IFN-γ, IL-2 and IL-4 (b) in culture supernatants of KLH-restimulated lymph node cells isolated from KLH-immunized mice and in vitro re-stimulated with KLH for 3 days. Proliferation indexes (mean) analyzed by FlowJo software are shown. (c,d) ELISA assays of nitrophenol-specific antibody (NP-specific Ab) production in the sera of mice at 14 days after primary immunization (c) or 7 days after secondary immunization (d), n=6. (e) The EAE induction in GLK-deficient mice and their wild-type littermates of F5 in B6 background (about 97%). Clinical scores (1-5) of mice are shown. n=7. (f) Flow cytometry of infiltrating $T_H17$ cells (CD45-gated) from the brains and spinal cords of MOG-immunized mice on day 14. (g) ELISA assays of IL-17 level in sera of MOG-immunized mice. n=6. (h) Flow cytometry of IL-17-producing CD4 T cells in in vitro differentiated $T_H17$ cells, (i) Suppression of CD3$^+$ T cells (labeled with the cytosolic dye CFSE) by wild-type or GLK-deficient $T_{reg}$ cells, presented as CFSE dilution in responding T cells cultured at a ratio of 3:1 (left) or 9:1 (right) with $T_{reg}$ cells plus anti-CD3-coated beads. Data are presented as mean±s.e.m. from three (panels b, e, f and h) or two (panels a, c, d, g and i) independent experiments. *, P value<0.05; **, P value<0.001.

Figure 5:
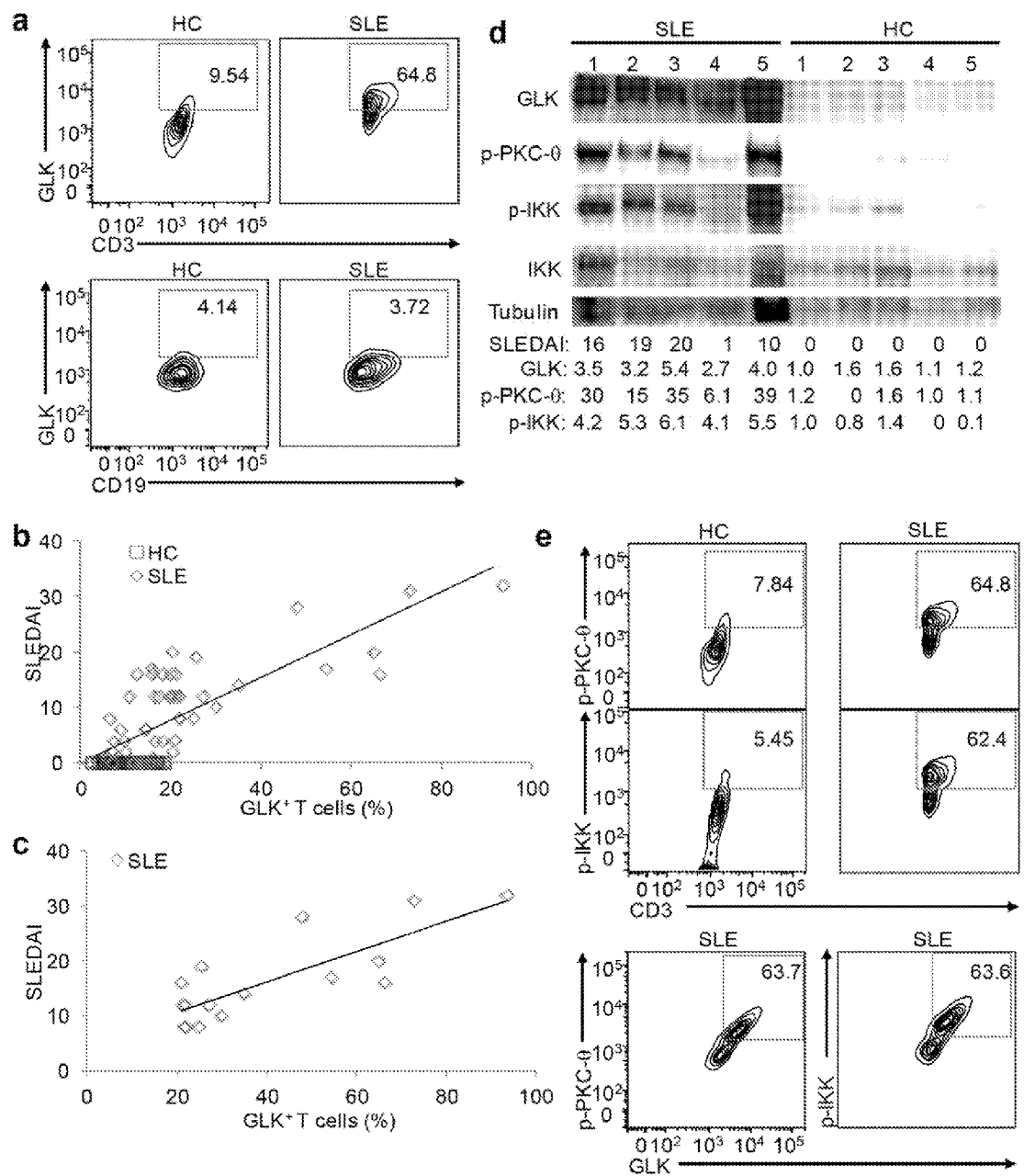

FIG. 5 shows that GLK expression and PKC-θ-T538 phosphorylation are induced in T cells from SLE patients, (a) Flow cytometry analyses of GLK-expressing (GLK') lymphocytes from PBLs of 49 SLE patients and 35 healthy controls (HC); the result from a SLE patient (SLEDAI=20) is shown as a representative, (b) Positive correlation and significant regression between SLEDAI and the percentages of GLK-expressing T cells from all SLE patients (Pearson correlation coefficient: r=0.773; simple linear regression: Y=−0.886+0.3901X, regression correlation coefficient: adjusted $R^2$=0.597, P value=1.08×10$^{-17}$). (c) High correlation and significant regression between SLEDAI and the percentages of GLK' T cells from SLE patients with high GLK' percentage (≥21%). (n=16; Pearson correlation coefficient: r=0.807; simple linear regression: Y=5.2085+0.2757X, regression correlation coefficient: adjusted $R^2$0.626, P value=0.000159). (d) Immunoblot analyses of GLK. p-PKC-θ, p-IKK and tubulin in the lysates of PBLs from 5 randomly sampled SLE patients and 5 healthy controls. SLEDAI for each patient was shown at lower panel. Relative fold changes are normalized to tubulin and shown at the bottom of the panel, (e) Flow cytometry of phospho-PKC-θ or phospho-IKK positive (CD3-gated) cells from PBLs of a representative SLE patient and healthy control (see panel a). Data are representative of at least three independent experiments (d,e).

Figure 6:
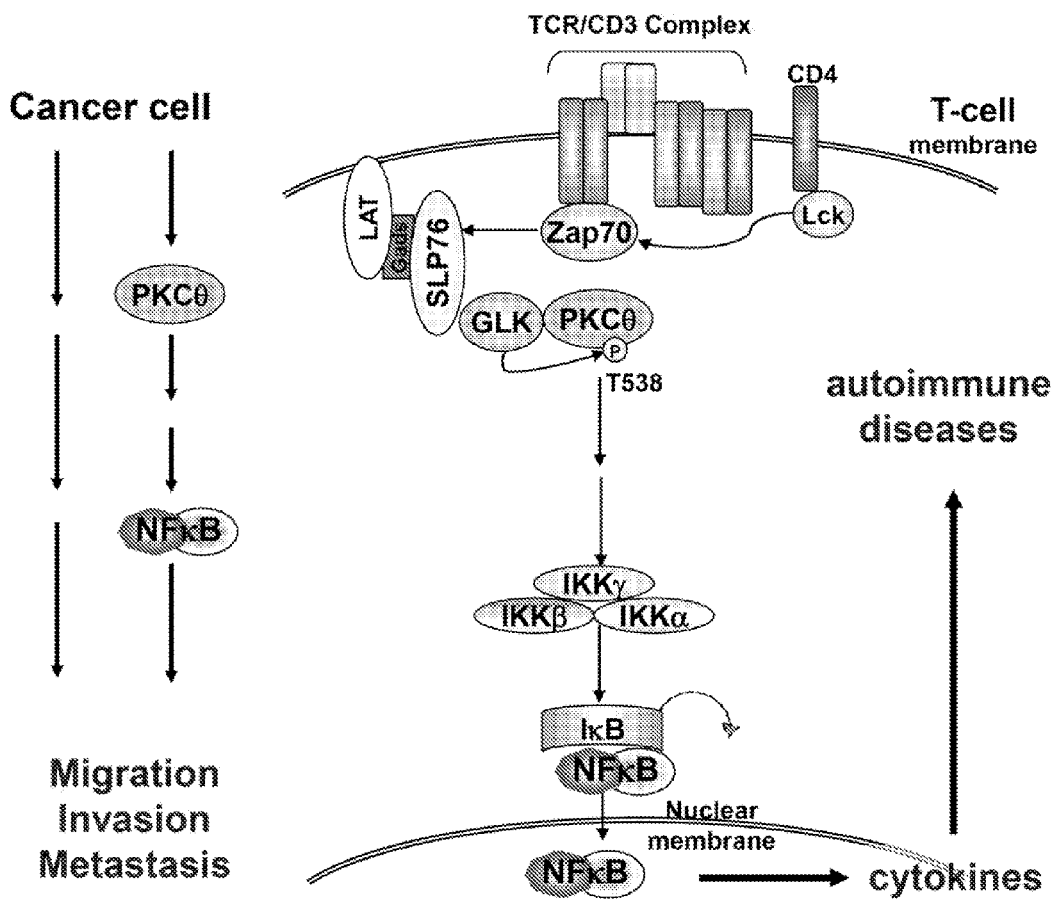

FIG. 6 shows a diagram of GLK-induced PKC-θ/NF-κB activation during TCR signaling. After TCR ligation, activated Lck is recruited to TCR complex and phosphorylates immunoreceptor tyrosine-based activation motifs (ITAMs) of CD3, resulting in Zap70 recruitment and activation. Zap70 activation induces the assembly of the proximal SLP-76 signaling complex. SLP-76 directly interacts with GLK and is required for GLK kinase activation. The activated GLK directly interacts with and phosphorylates PKC-θ at T538, resulting in PKC-θ membrane translocation and kinase activation. The activated PKC-θ in turn induces the activation of the IKK/NF-κB signaling cascade. In cancer cells, GLK induces migration/invasion/metastasis through PKC/NF-κB signaling or PKC-independent signaling.

Figure 7:
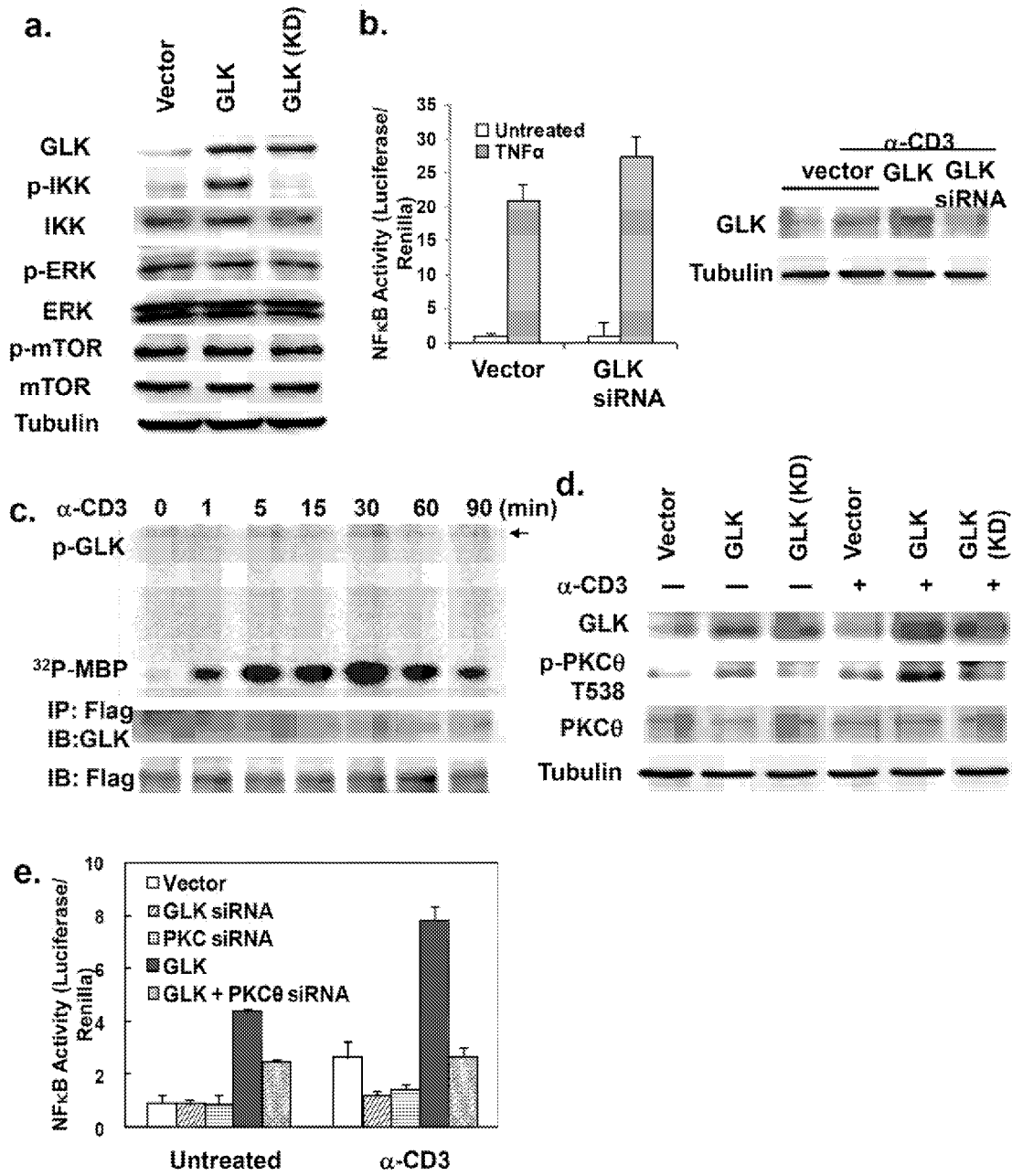

FIG. 7 shows that GLK induces NF-κB activation in T cells upon TCR stimulation, (a) Immunoblot analyses of GLK, p-IKK, IKK, p-Erk. Erk, p-mTOR, mTOR and tubulin in the lysates of vector, GLK, or GLK(KD) mutant-expressing Jurkat T cells stimulated with anti-CD3 antibodies for 15 min. (b) NF-κB reporter assays of Jurkat cells transfected with empty vector or GLK siRNA following TNF-α stimulation (left). Immunoblot analyses of GLK and tubulin in lysates of Jurkat T cells transfected with empty vector, plasmid encoding GLK or GLK siRNA following anti-CD3 stimulation, (c) In vitro kinase assays of GLK isolated from Flag-GLK-expressing J-TAg T cells stimulated with anti-CD3 antibodies. Arrow, GLK autophosphorylation. IP, immunoprecipitation. IB, immunoblot. (d) Immunoblot analyses of GLK, p-PKC-θ, PKC-θ and tubulin in lysates of J-TAg T cells transfected with plasmid encoding GLK or the GLK(KD) mutant following CD3 stimulation for 30 min. (e) NF-κB reporter assays of Jurkat T cells transfected with indicated empty vector, plasmid encoding GLK, GLK or PKC-θ siRNA alone, or plasmids encoding GLK plus PKC-θ siRNA. Cells were stimulated with or without anti-CD3 antibodies for 2 h. Data are representative of three independent experiments. *, P value<0.05; **, P value<0.001. Error bars in panels (b) and (e) are standard deviations (s.d.) of triplicate samples. Data are representative of at least three independent experiments.

Figure 8:
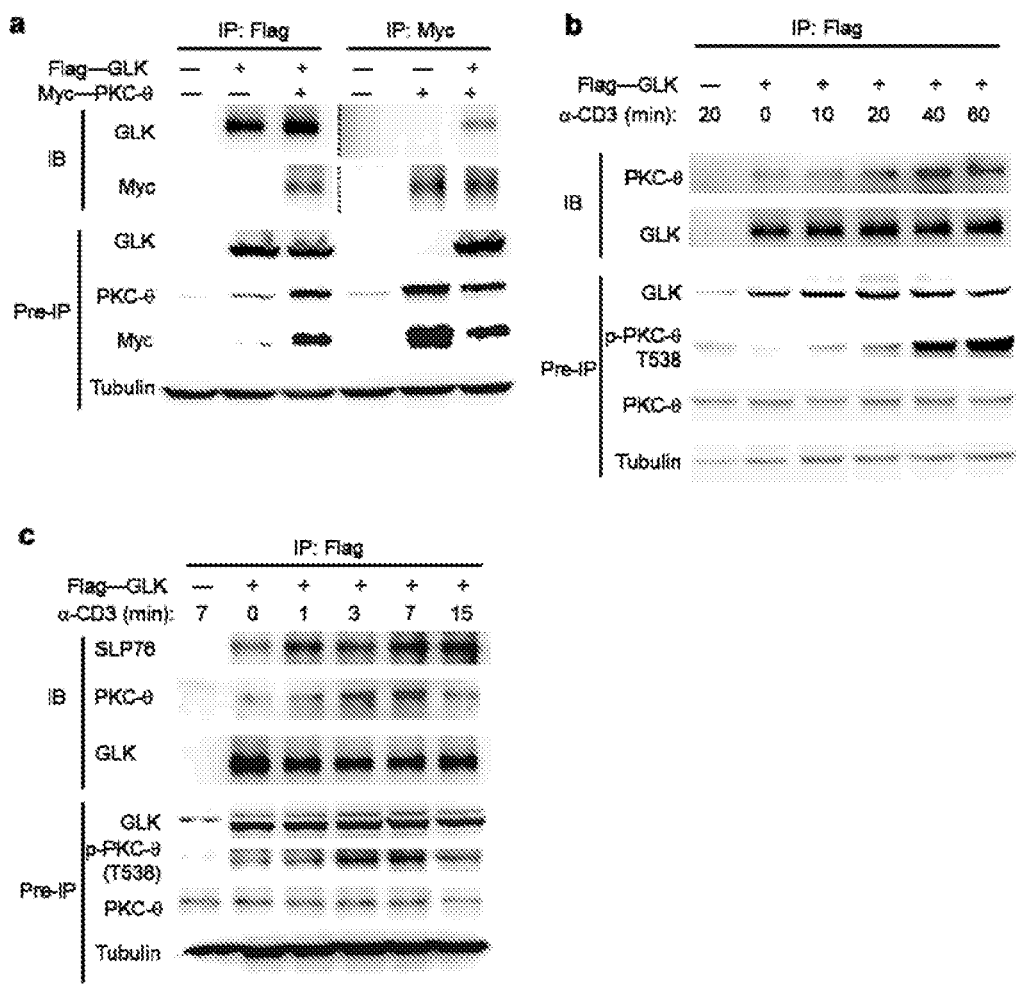

FIG. 8 shows that GLK interacts with PKC-θ. (a) Co-immunoprecipitation (IP) and immunoblot (IB) analyses of GLK and PKC-θ in lysates of HEK293T cells transfected with empty vector or plasmid encoding GLK plus with or without plasmid encoding PKC-θ. (b,c) Co-immunoprecipitations of the Flag-GLK and endogenous PKC-θ in lysates of Flag-GLK-expressing J-TAg (b) or EL4 (c) T cells stimulated with 5 μg/ml anti-CD3 antibodies (upper panel). Immunoblot analyses of GLK, p-PKC-θ, PKC-θ and tubulin in pre-immunoprecipitation samples (lower panel). Data are representative of at least three independent experiments.

Figure 9:
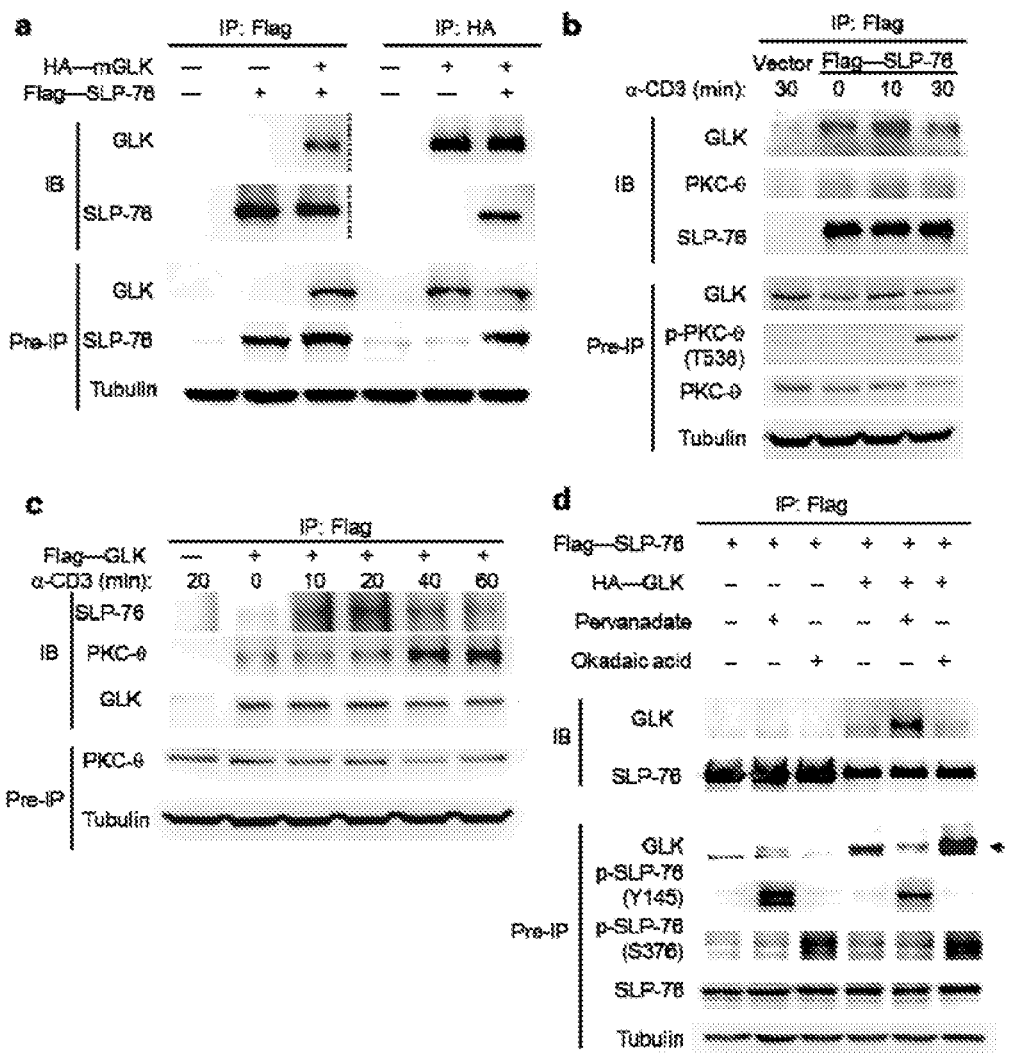

FIG. 9 shows that The interaction between GLK and SLP-76 is mediated through tyrosine phosphorylation, (a) Co-immunoprecipitations (IP) and immunoblot (IB) analyses of GLK and SLP-76 in lysates of HEK293T cells transfected with empty vector or plasmid encoding SLP-76 plus with plasmid encoding GLK. (b) Co-immunoprecipitations of SLP-76 and GLK in lysates of Flag-SLP-76-overexpressed J-TAg T cells stimulated with anti-CD3 antibodies, (c) Co-immunoprecipitations of anti-CD3-induced SLP-76/GLK/PKC-θ interaction in J-TAg T cells transfected with Flag-GLK. (d) Co-immunoprecipitations of GLK and SLP-76 in lysates of HEK293T cells transfected with plasmid encoding SLP-76 plus empty vector or plasmid encoding GLK. Cells were pre-treated with/without the tyrosine phosphatase inhibitor pervanadate or the serine/threonine phosphatase inhibitor okadaic acid. Data are representative of at least three independent experiments.

Figure 10:
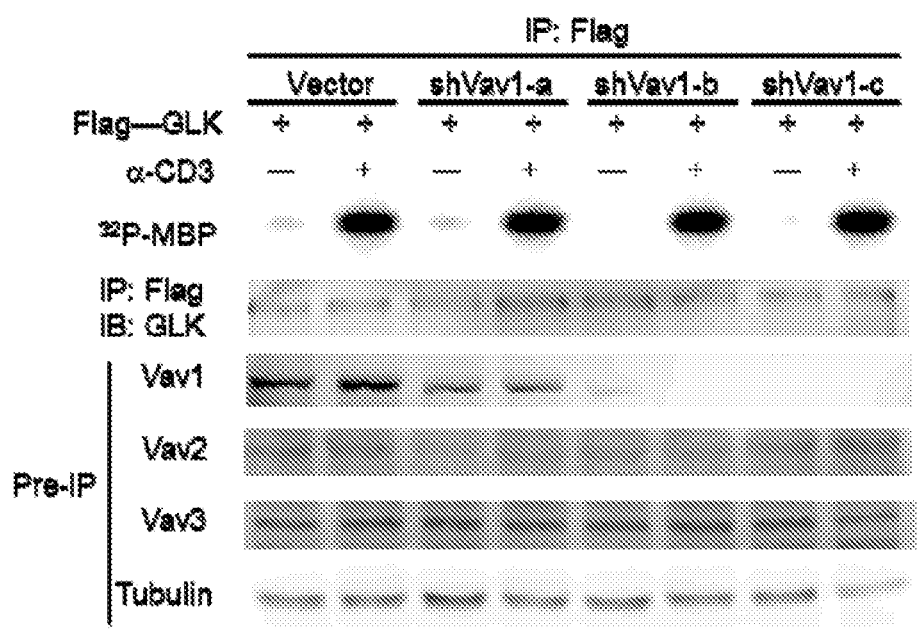

FIG. 10 shows that Vav1 is not required for TCR-induced GLK activation. In vitro kinase assays of Flag-GLK isolated from the Vav1 shRNA-knocked down Jurkat T cells (shVav1 a-c) stimulated for 30 min with or without anti-CD3 antibodies. MBP was used as the substrate. Data are representative of at least three independent experiments.

Figure 11:
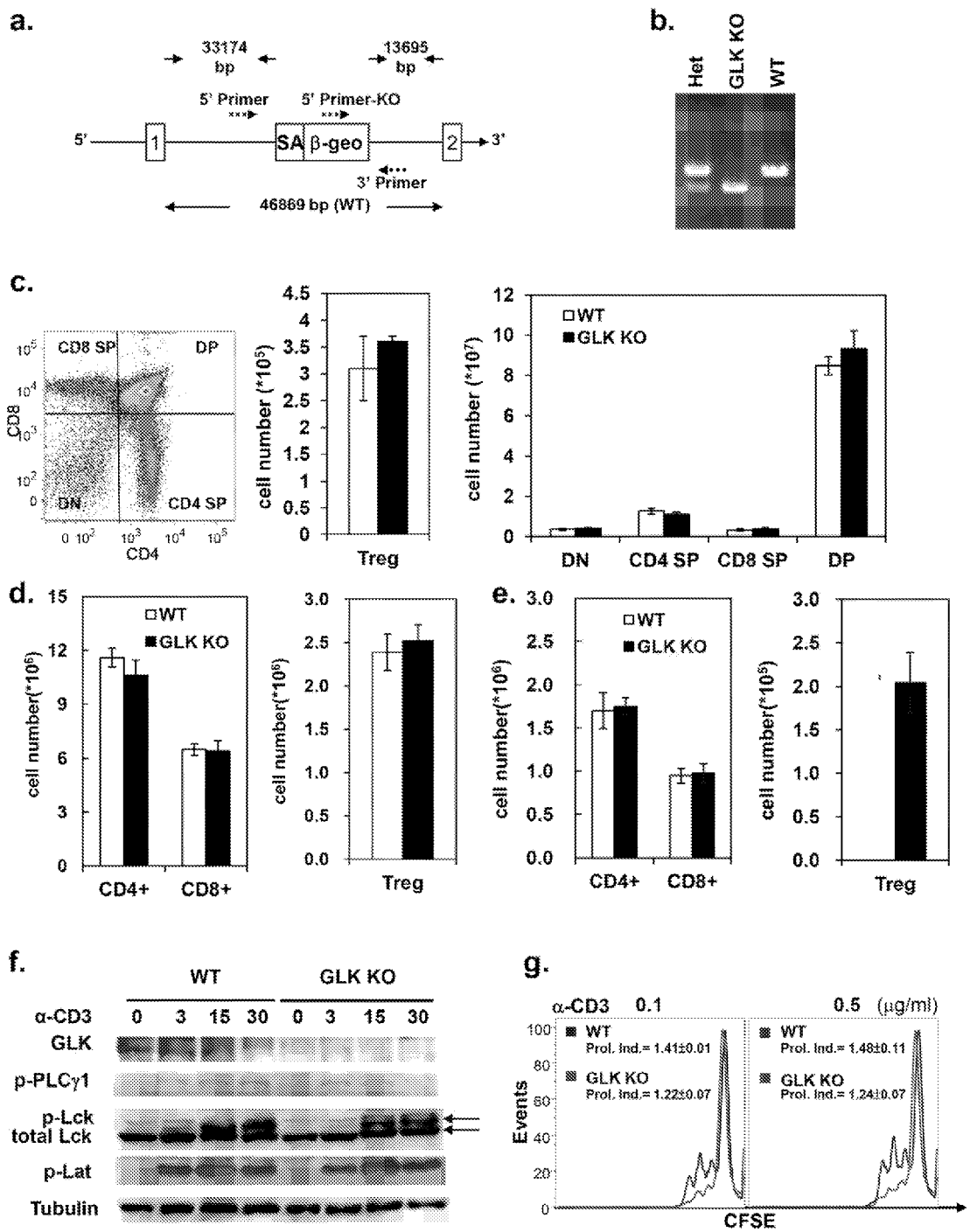

FIG. 11 shows that T cell development is normal in GLK-deficient mice, (a) The structure of the gene-trap vector. β-geo, a fusion with β-galactosidase and neomycin phosphotransferase genes; SA, splicing acceptor; the box with numbers, the exon of GLK; dotted arrow, the primers for PCR. (b) PCR analyses of GLK wild-type and mutant allele in the genomic DNA from mouse tails. The PCR products of the higher band (1400 bp) indicate wild-type (WT) allele, and the lower band (1000 bp) indicates GLK mutant allele, (c-e) Flow cytometry analyses of T lymphocytes from the thymus (c), spleen (d), and lymph nodes (e) of wild-type and GLK-deficient (GLK-KO) mice. Data are presented as mean±s.e.m. (f) Immunoblot analyses of GLK, p-PLCγl, p-Lck, Lck and tubulin in lysates of mouse T cells stimulated with anti-CD3-biotin and streptavidin. (g) CFSE dilution assays of T cell proliferation in purified T cells. Proliferation indexes (mean±s.e.m) analyzed by FlowJo software are also shown. Data are representative of at least three independent experiments (b-g).

Figure 12:
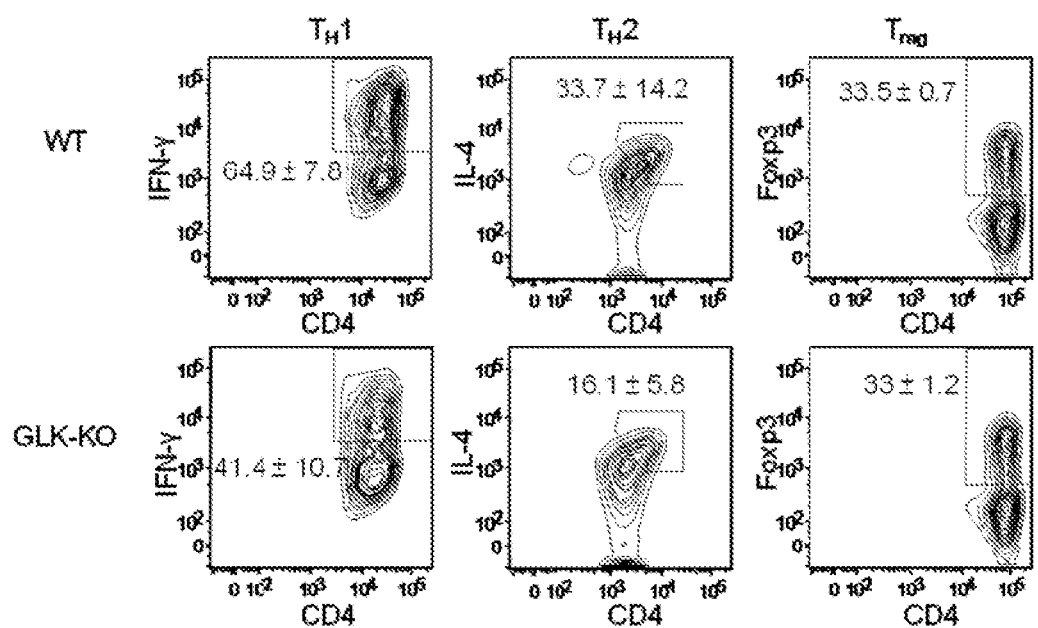

FIG. 12 shows that differentiation of $T_H1$ and $T_H2$ is impaired by GLK deficiency. Flow cytometry of IFN-γ-producing, IL-4-producing and Foxp3-positive $CD4^+$ T cells. Data are presented as mean±s.e.m. Data are representative of at least three independent experiments.

Figure 13:
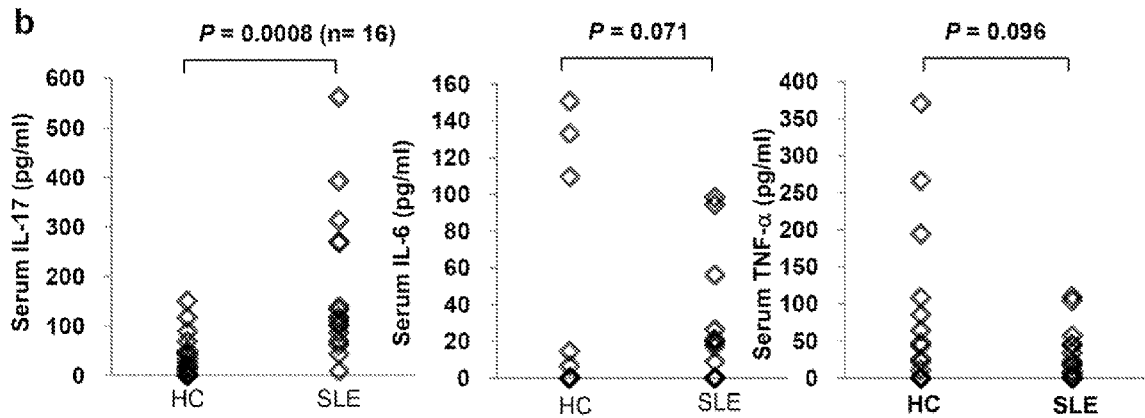

FIG. 13 shows that serum IL-17 levels are increased in SLE patients, (a) Profile of SLE patients and paired healthy control. Data are presented as mean±s.d. (b) ELISA assays of IL-17, TNF-α, and IL-6 in the sera of SLE patients and healthy controls (HC).

Figure 14:
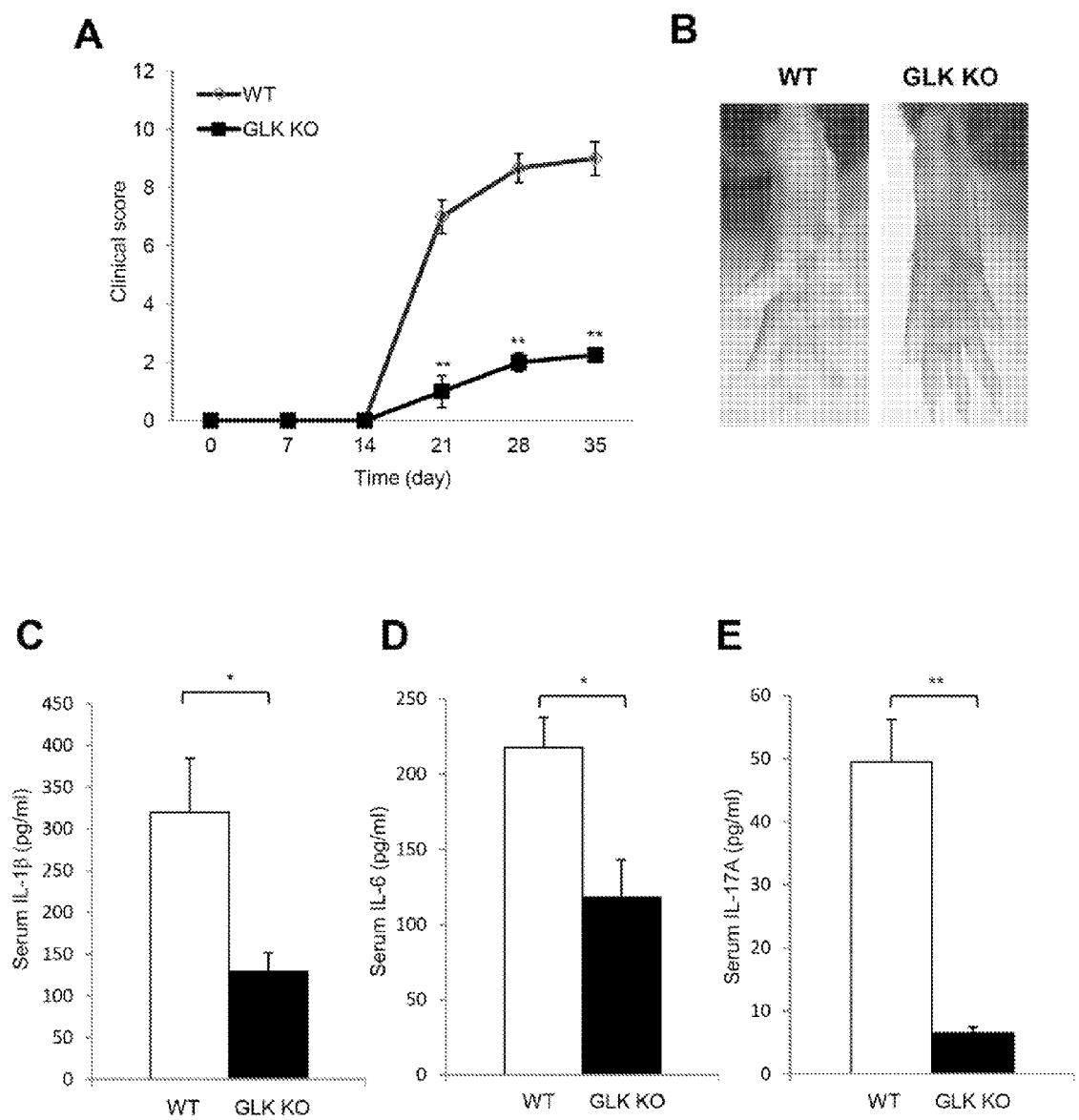

FIG. 14 shows impaired induction of CIA in GLK-deficient mice. (A) The mean clinical scores±SEM comparing disease development between GLK-deficient and wide-type (WT) mice. Animals were scored once per week after collagen immunization. n=5. (B) Hind joints obtained clay 7 after the second immunization. (C) Serum IL-1β levels from GLK-deficient and WT mice on day 7 after immunization were determined by ELISA assays. (D and E) Serum IL-6 (D) and IL-17A (E) levels from mice on day 7 after the second immunization were determined by ELISA assays. *, p<0.5; **, p<0.01.

Figure 15:
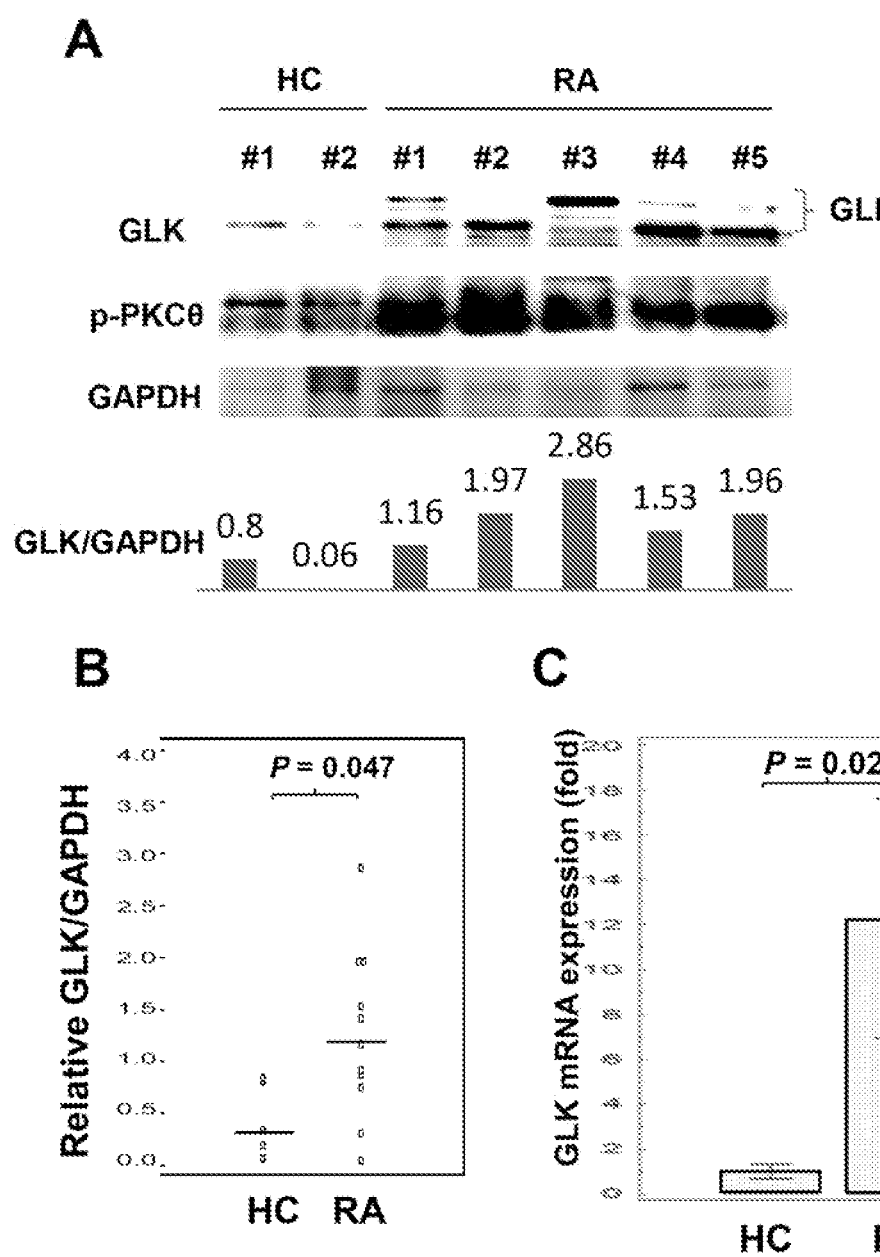

FIG. 15 shows increased GLK protein and mRNA levels in peripheral blood T cells from RA patients. (A) Immunoblotting analyses of GLK and phosphorylated PKC-θ (p-PKC-θ) in purified peripheral blood T cells from five randomly sampled RA patients and two healthy controls (HC). Relative fold changes of GLK. were normalized to GAPDH and are shown at the bottom of the panel. (B) Comparison of GLK expression levels between eleven RA patients and five HC. Data are presented as relative fold changes of GLK with normalization to GAPDH. p=0.047. (C) Levels of GLK messenger RNA (mRNA) in purified peripheral blood T cells of twelve RA patients and thirteen HC. Data are expressed as the ratio of GLK to peptidylprolyl isomerase A (PPIA) mRNA transcripts. Error bars indicate standard errors of the mean (SEM). p=0.0029.

Figure 16:
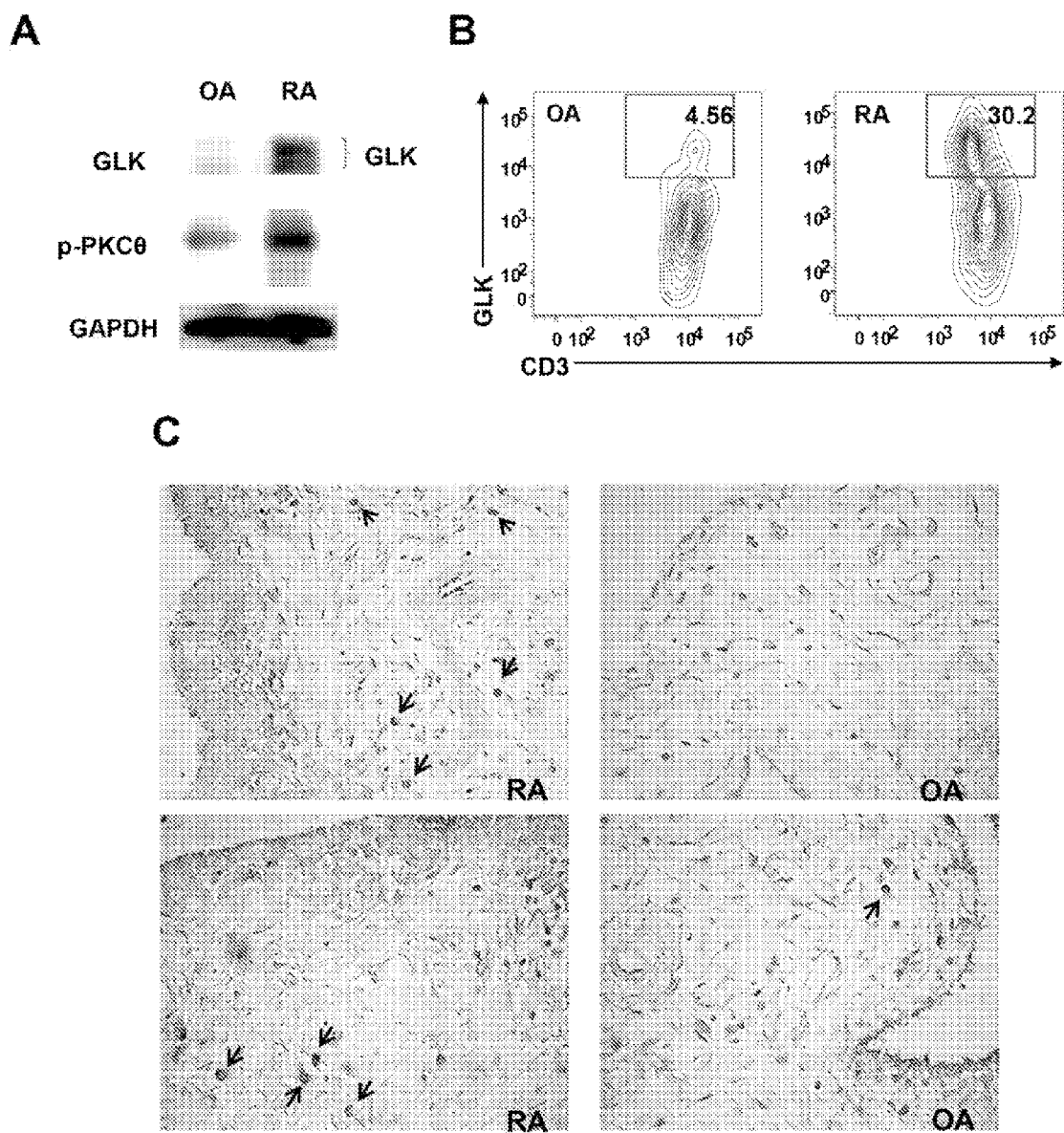

FIG. 16 shows overexpression of GLK in T cells from synovial fluids and synovial tissues of RA patients. (A) Immunoblotting analyses of GLK and p-PKC-θ in synovial fluids leukocytes from representative RA and OA patients. (B) Flow cytometry analyses of GLK-positive CD3-gated T cells in synovial fluids of representative RA and OA patients. (C) Immunohistochemistry staining for anti-GLK (blue) and anti-CD3 (brown) in synovial tissues of two RA and two OA patients. Arrows represent GLK-expressing T cells.

Figure 17:
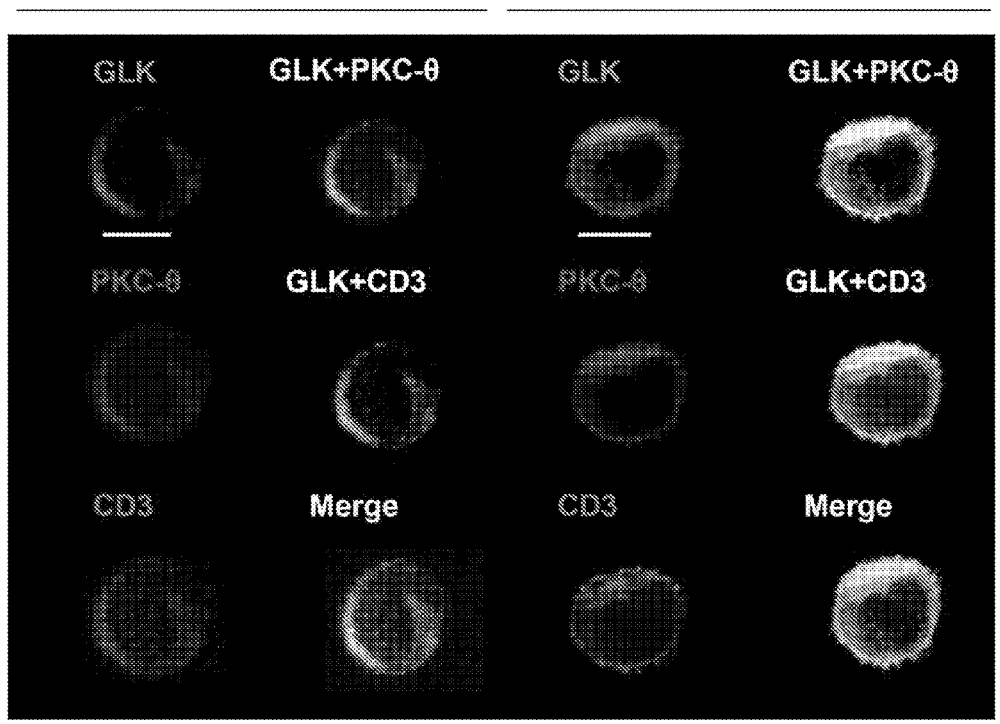
Figure 17:
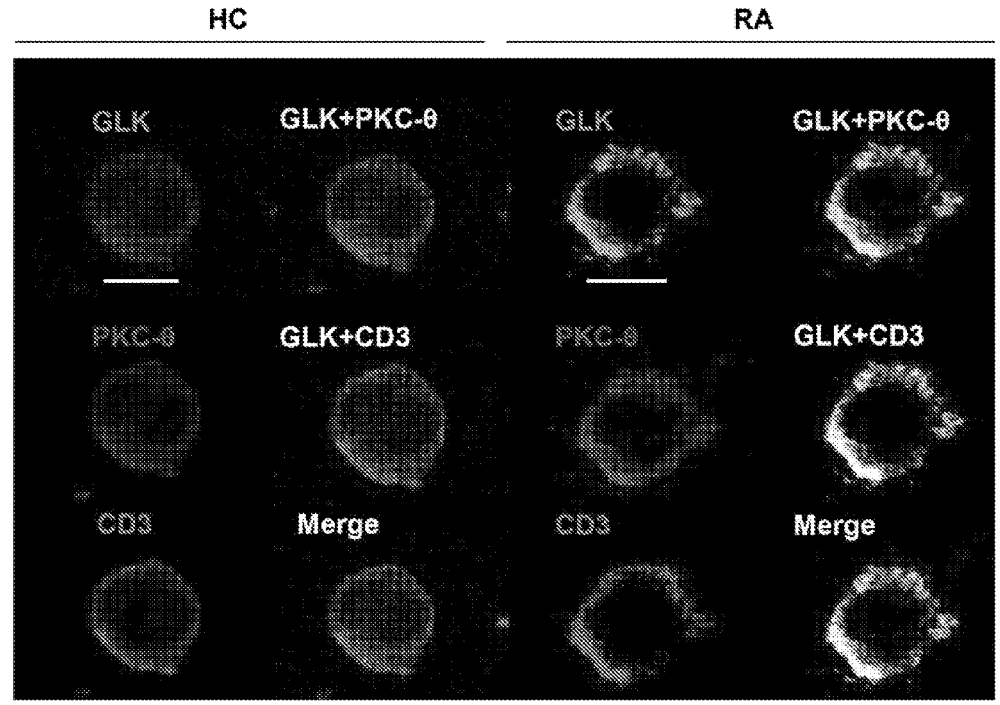

FIG. 17 shows co-localization of GLK, PKC-θ and CD3 in T cells from synovial fluids and the peripheral blood of RA patients. (A) Con focal microscopy of GLK, PKC-θ and CD3 in synovial fluid T cells of RA and OA patients by TCS SP5 (LEICA) confocal system. (B) Confocal microscopy of GLK, PKC-θ. and CD3 in peripheral blood T cells of RA patients and HC by TCS SP5 (LEICA) confocal system.

Figure 18:
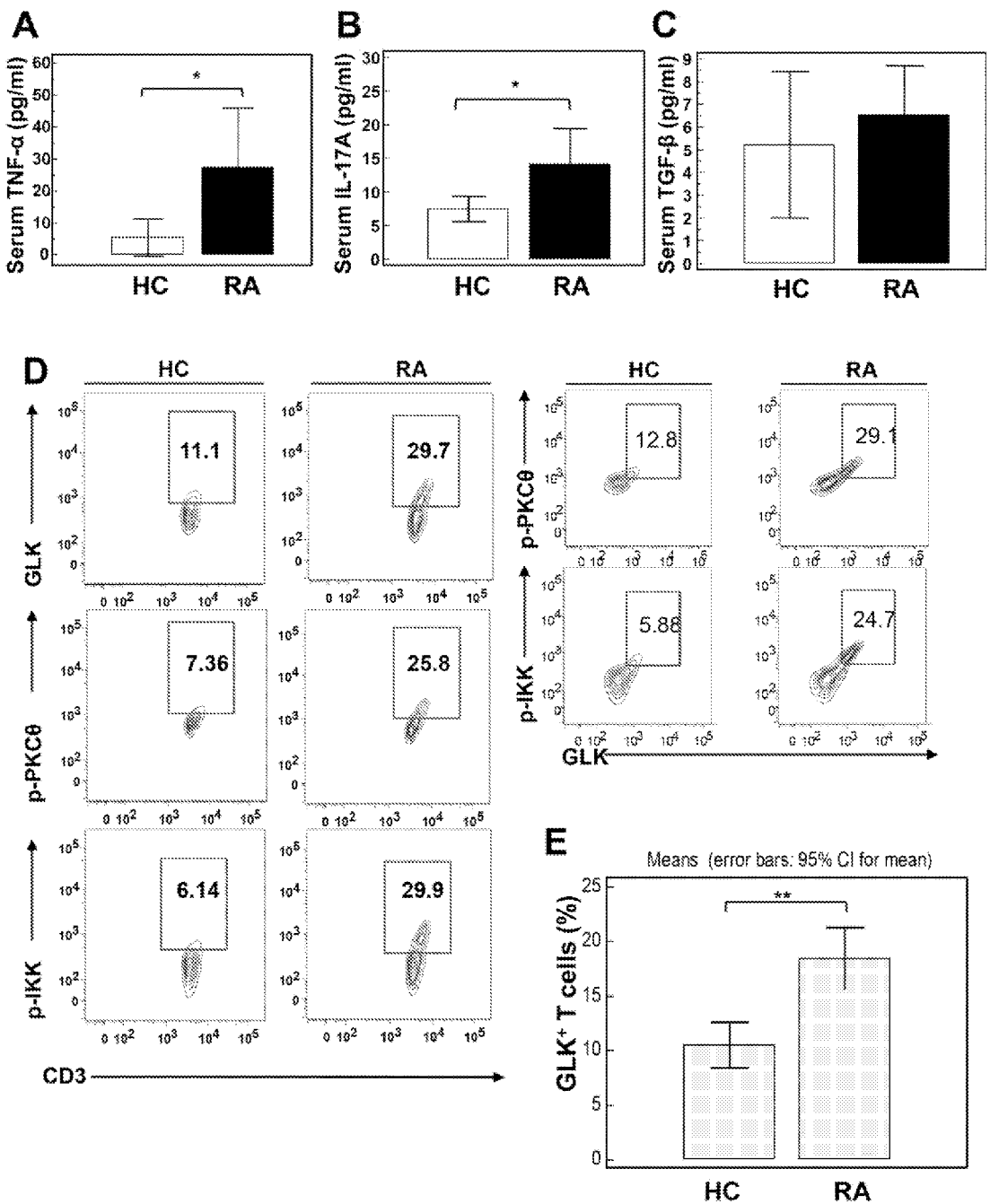

FIG. 18 shows increased inflammatory cytokines levels and co-existence of GLK, p-PKC-θ and p-IKK in peripheral blood T cells of RA patients. Serum levels of (A) TNF-α, (B) IL-6, and (C) TGF-β levels in RA patients and healthy controls were determined by ELISA assays. (D) Flow cytometry analyses of GLK/p-PKC-θ/p-IKK-positive cells from peripheral blood leukocytes of a representative RA patient and healthy control (HC). CD3-positive T cells were gated and then analyzed by How cytometry. (E) Comparison of GLK expression in CD3-gated T cells between 30 RA patients and 24 HC. Error bars indicate 95% confidence interval for means. *, p<0.5; **, p<0.01.

Figure 19:
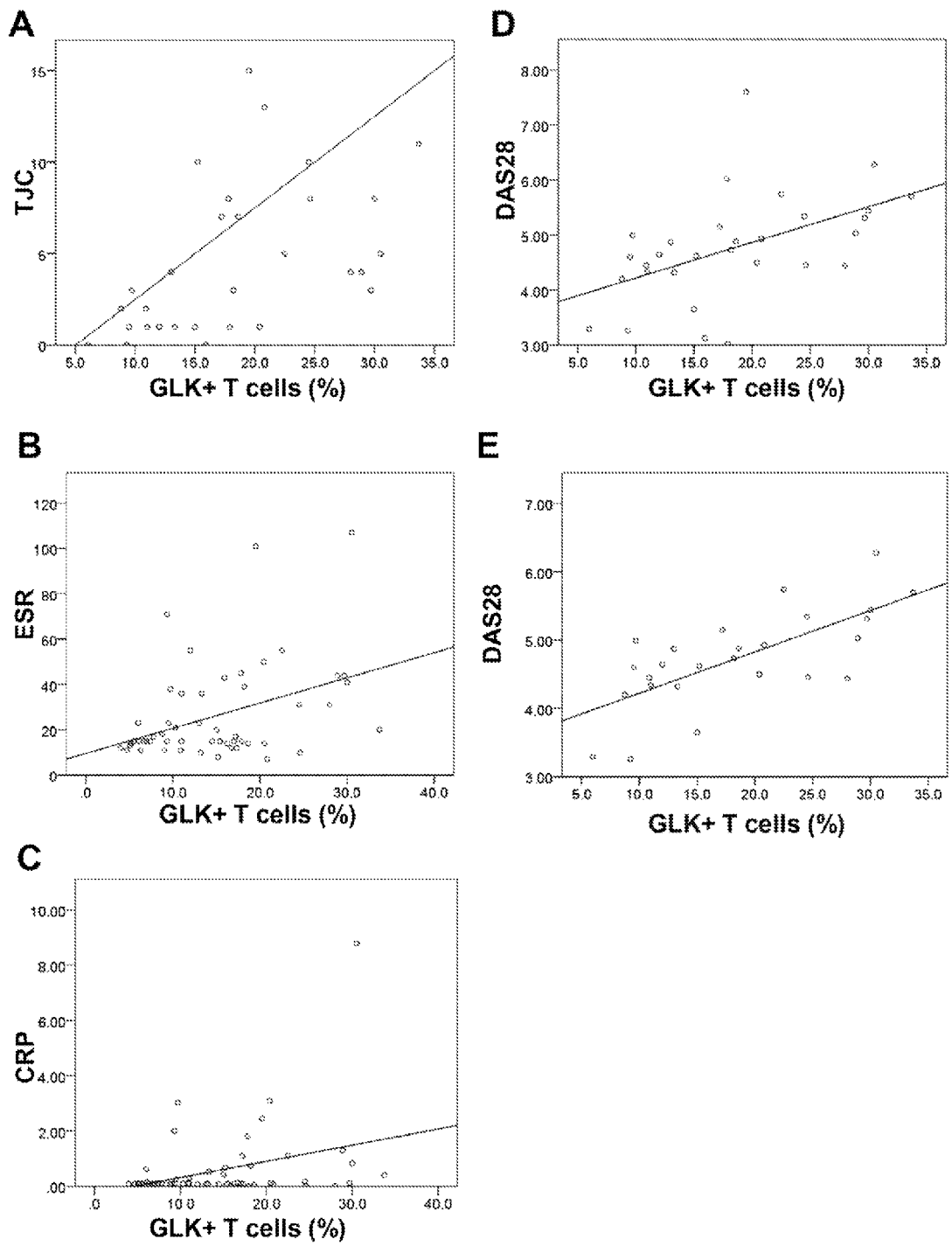

FIG. 19 shows correlation of GLK-expressing T-cell frequencies with RA disease activity. Positive correlation and significant regression between (A) tender joint counts (TJC) and the frequency of GLK-expressing T cells (Pearson's correlation coefficient: r=0.500; simple linear regression: Y=0.274X−0.402, p=0.005) (B) erythrocyte sedimentation rate (ESR) and the frequency of GLK-expressing T cells (Pearson's correlation coefficient: r=0.400; simple linear regression: Y=1.113X+9.602, p=0.003) (C) C-reactive protein (CRP) and the frequency of GLK-expressing T cells (Pearson's correlation coefficient: r=0.330; simple linear regression: Y=0.059X−0.27, p=0.015) (D) DAS28 and the frequency of GLK-expressing T cells from all RA patients (Pearson's correlation coefficient: r=0.606; simple linear regression: Y=0.065X+3.575, p=0.005). (E) Correlation and significant regression between DAS28 and the frequencies of GLK-expressing T cells from 26 of 30 patients (Pearson's correlation coefficient: r=0.713; simple linear regression: Y=0.061X+3.6158, p=0.0000639).

Figure 20:
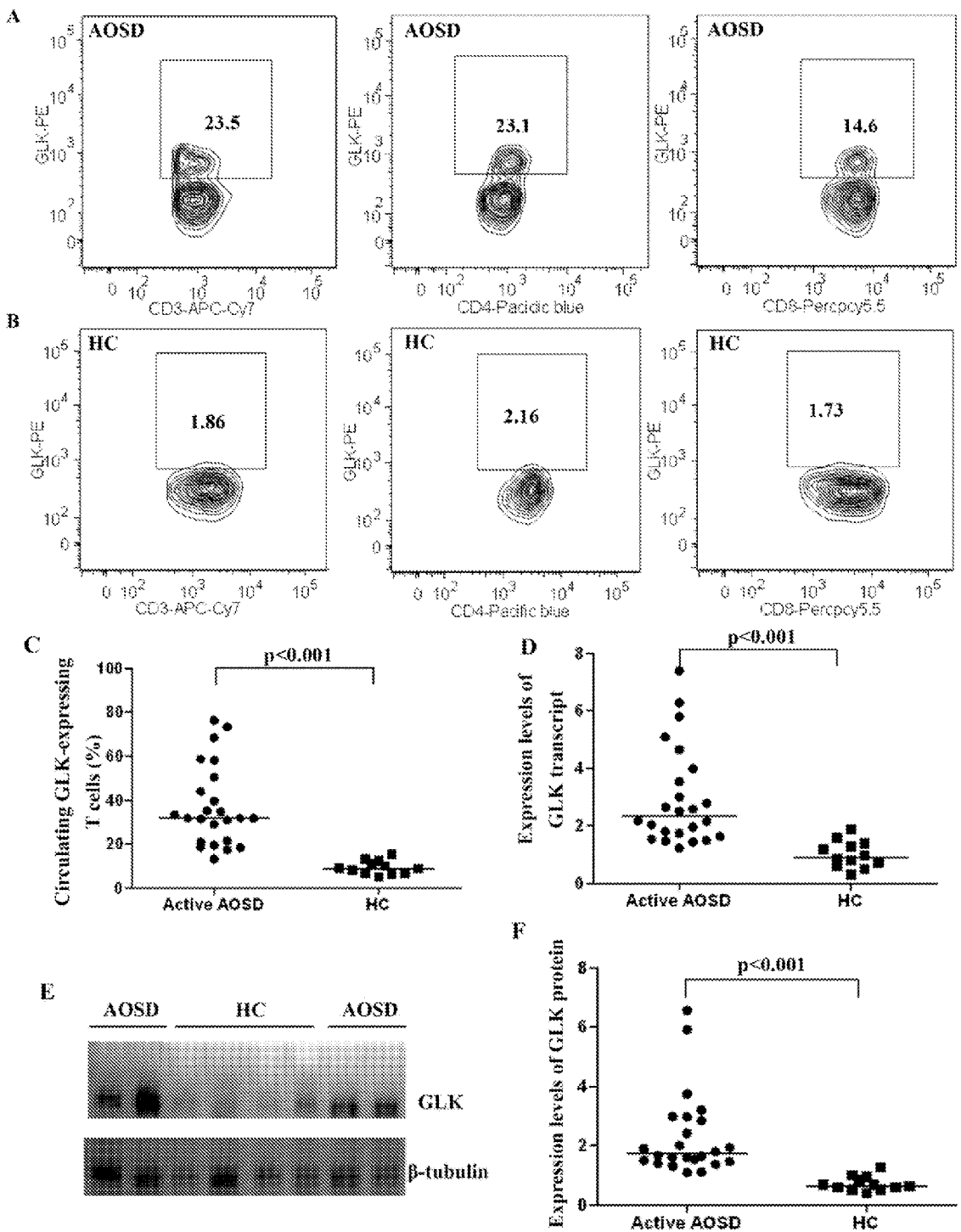

FIG. 20 shows the GLK expression levels in T cells from patients with adult-onset Still's diseases (AOSD) and healthy controls (HC). Representative examples of flow cytometry contour plots of intracellular GLK production in $CD3^+$ T cells, $CD4^+$ T cells, and $CD8^+$ T cells were obtained from peripheral blood of one AOSD patient (A) and one healthy control (B). The frequencies of circulating GLK-expressing CD3+ T cells (C) were obtained from 24 active AOSD patients and 12 HC. The comparison in the relative expression levels of GLK transcript (D) between AOSD patients and HC. Immunoblot analyses of GLK expression (E) in the lysates of peripheral blood T cells from AOSD patients and HC. The comparison in the relative expression levels of GLK protein between active AOSD patients and HC (F). Horizontal bar indicates median value. *P-value was determined by Mann-Whitney U test.

Figure 21:
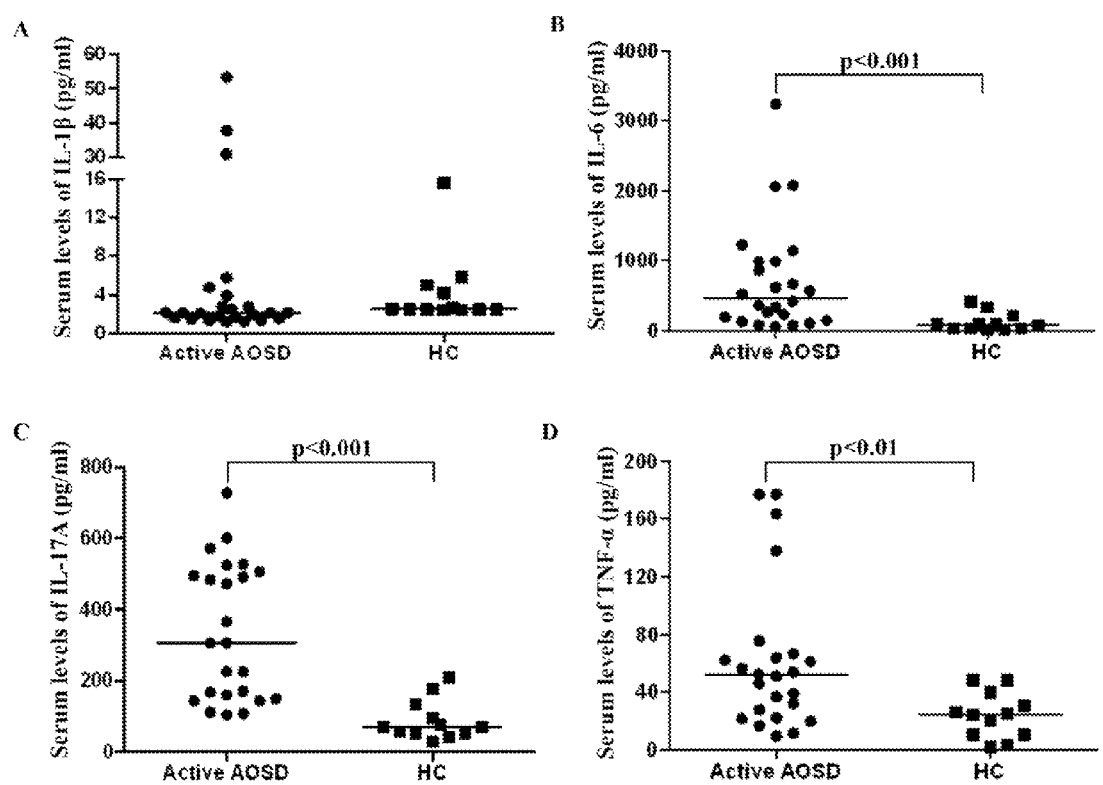

FIG. 21 shows the comparison in serum levels of inflammatory cytokines including IL-1β (A), IL-6 (B). IL-17A (C), and TNF-α (D) from active patients with adult-onset Still's diseases (AOSD) and healthy controls (HQ. Horizontal bar indicates median value. *P-value was determined by Mann-Whitney U test.

Figure 22:
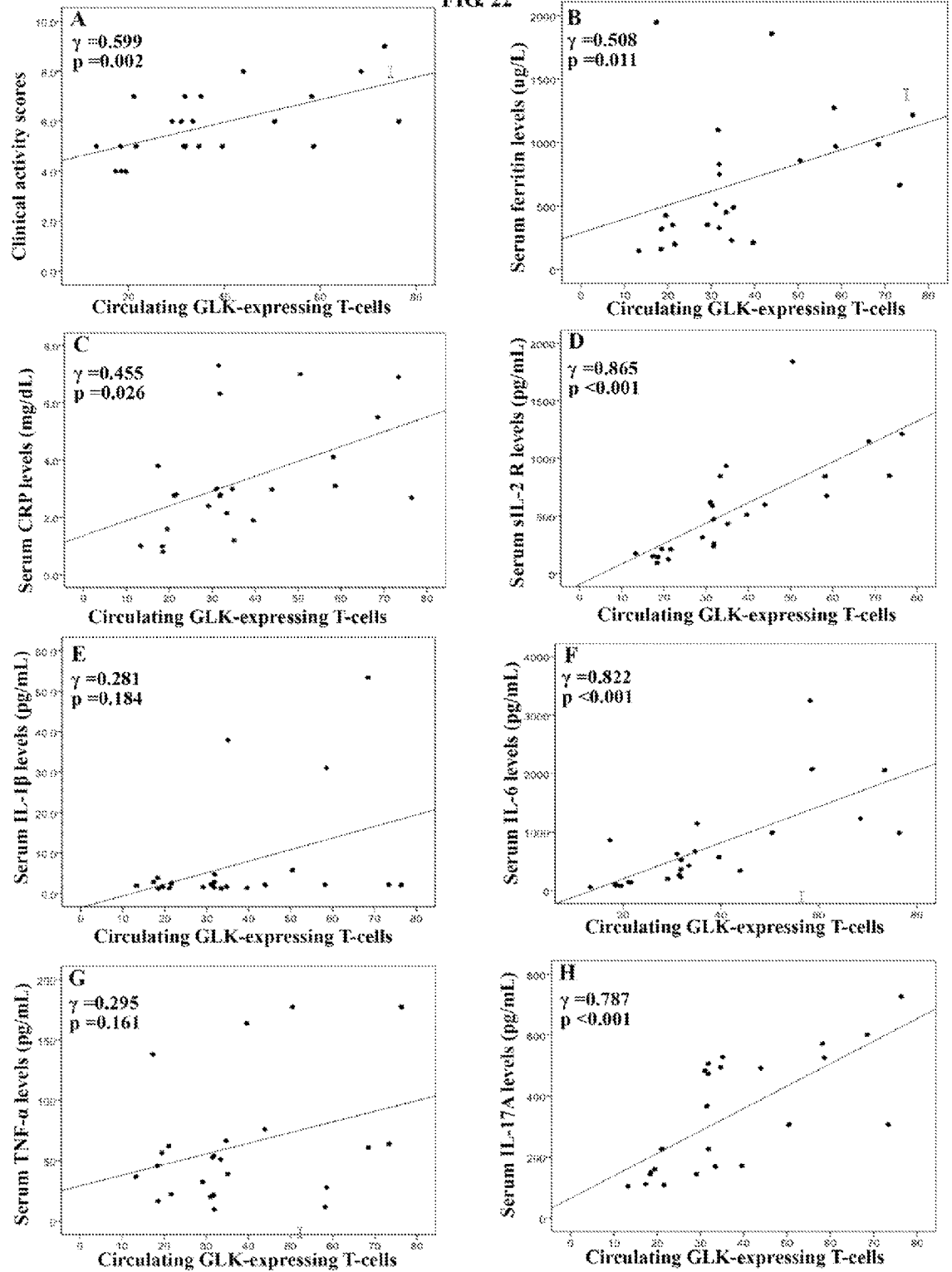

FIG. 22 shows the correlation between the frequencies of circulating GLK-expressing T cells and disease activity score (A), activity parameters including serum ferritin levels (B), C-reactive protein (CRP) levels (C) and soluble interleukin-2 receptor levels (D), and serum levels of cytokines including IL-1β (E), IL-6 (F), TNF-α (G), and IL-17A (H) from 24 patients with adult-onset Still's diseases. Correlation coefficients (γ) and p-value were obtained by the nonparametric Spearman's rank correlation test.

Figure 23:
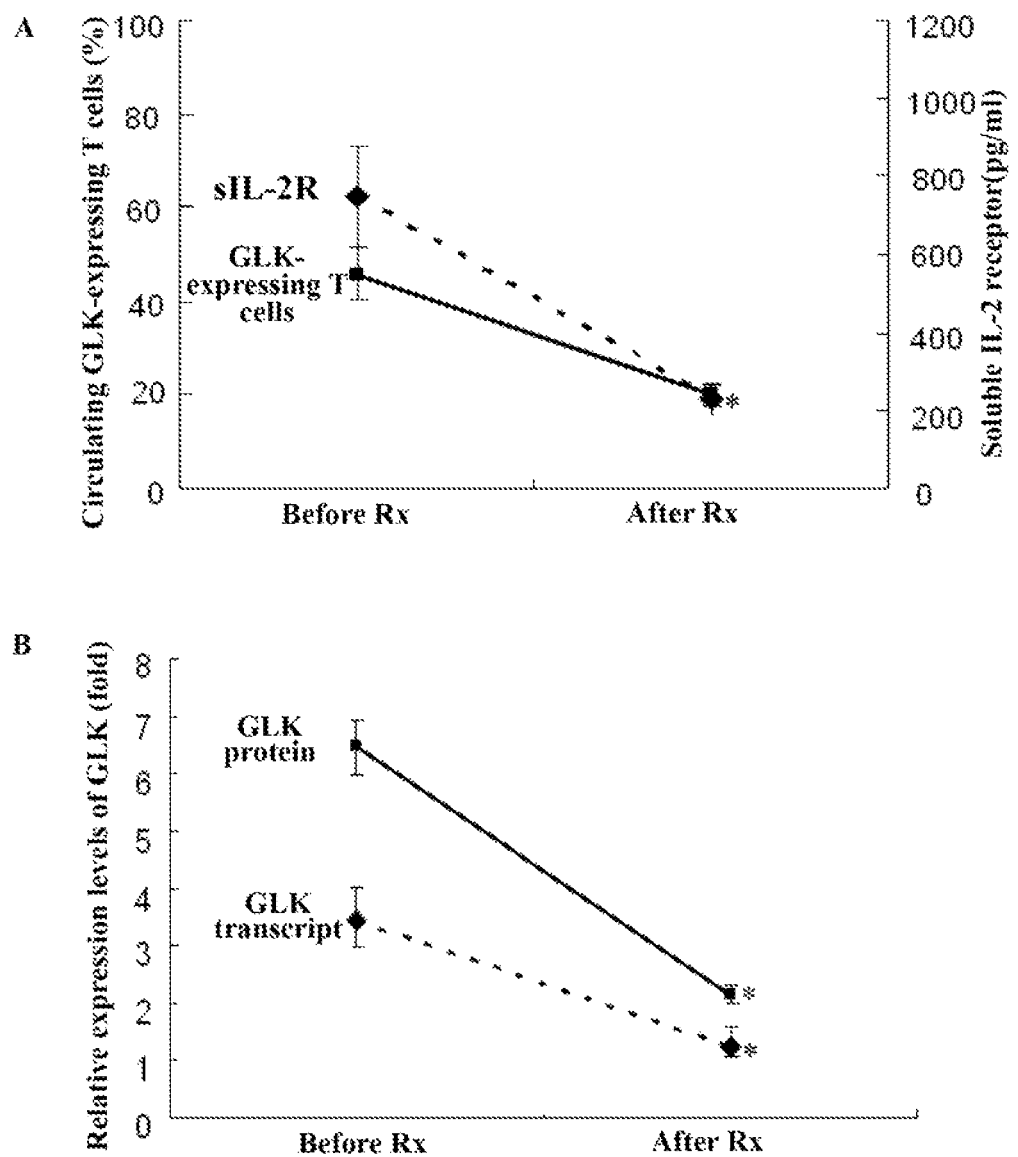

FIG. 23 shows changes in the levels of circulating GLK-expressing T cells, the expression levels of GLK proteins as well as transcripts, and serum levels of soluble interleukin-2 receptors (sIL-2R) in 12 AOSD patients after effective therapy. Data are presented as mean±SEM. *p<0.005, versus before treatment, determined by the Wilcoxon signed rank test.

Figure 24:
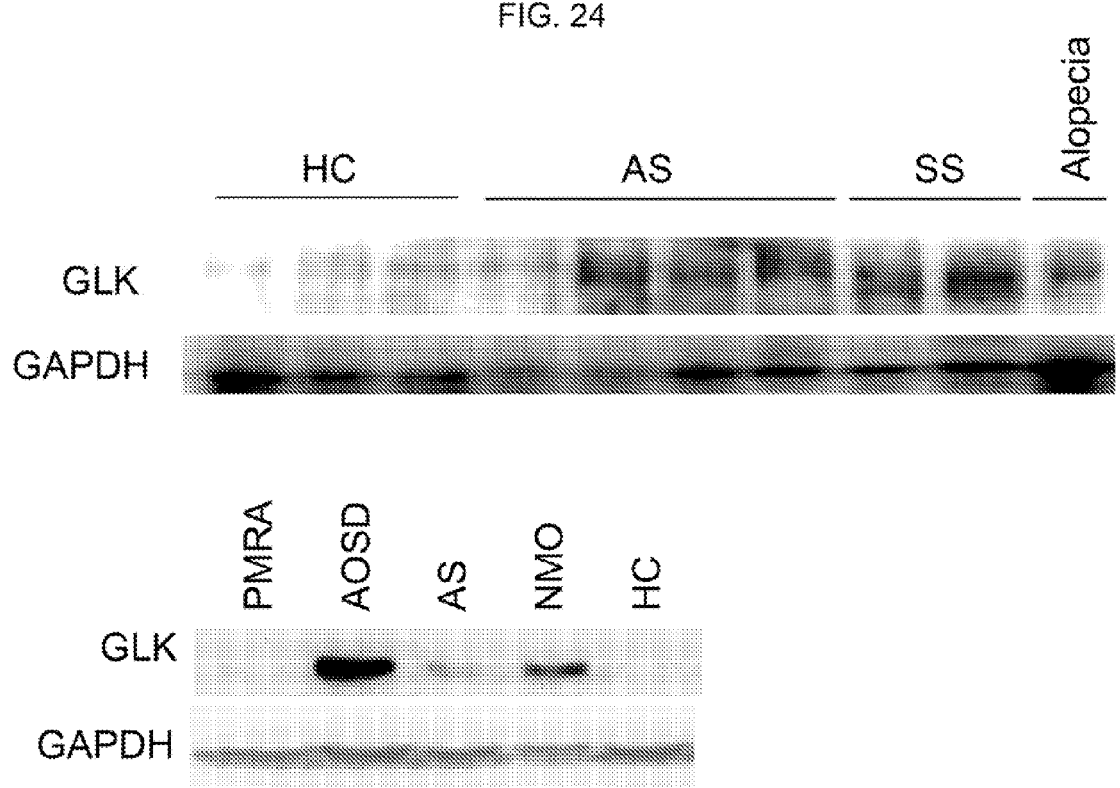

FIG. 24 shows GLK overexpression in T cells from patients with autoimmune diseases. Immunoblotting analyses of GLK and GAPDH in lysates of purified T cells from ankylosing spondylitis (AS), Sjögren's syndrome (SS), alopecia, adult onset Still's disease (AOSD), and neuromyelitis oplitica (NMO) patients. HC: healthy control.

Figure 25:
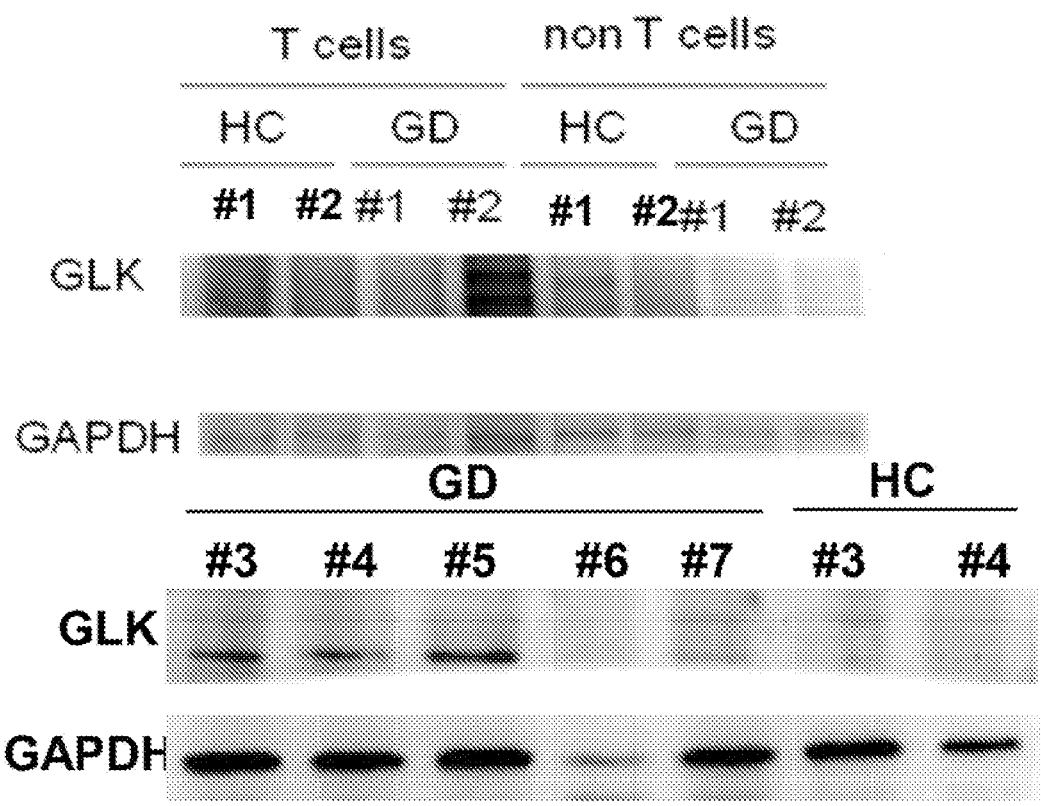
Figure 25:
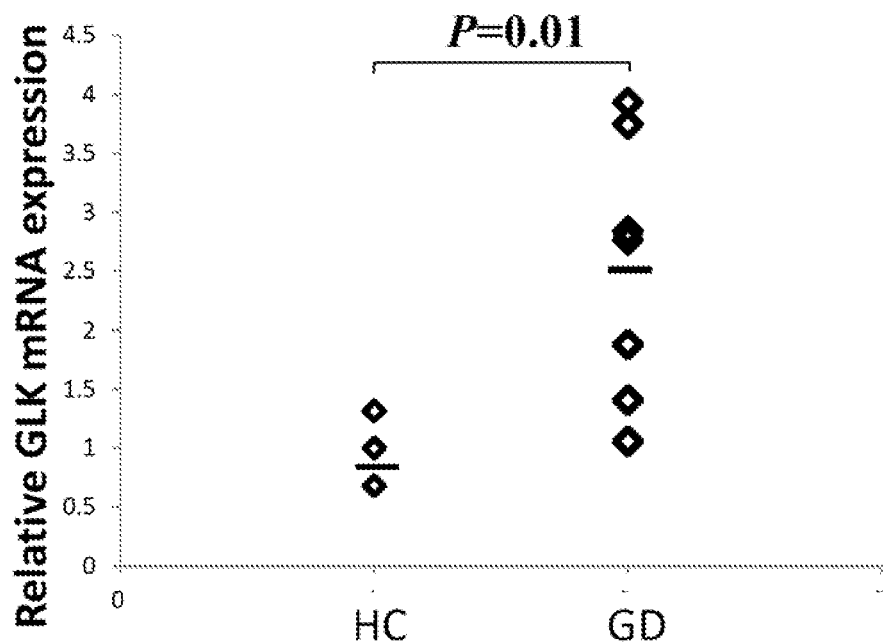

FIG. 25 shows GLK overexpression in T cells from patients with Grave's disease, a. Immunoblotting analyses of GLK and GAPDH in lysates of purified T cells from Grave's disease (GD) patients and healthy controls (HC). b. Quantitative polymerase chain reaction showed relative GLK expression between HC (n=3) and GD (n=7).

Figure 26:
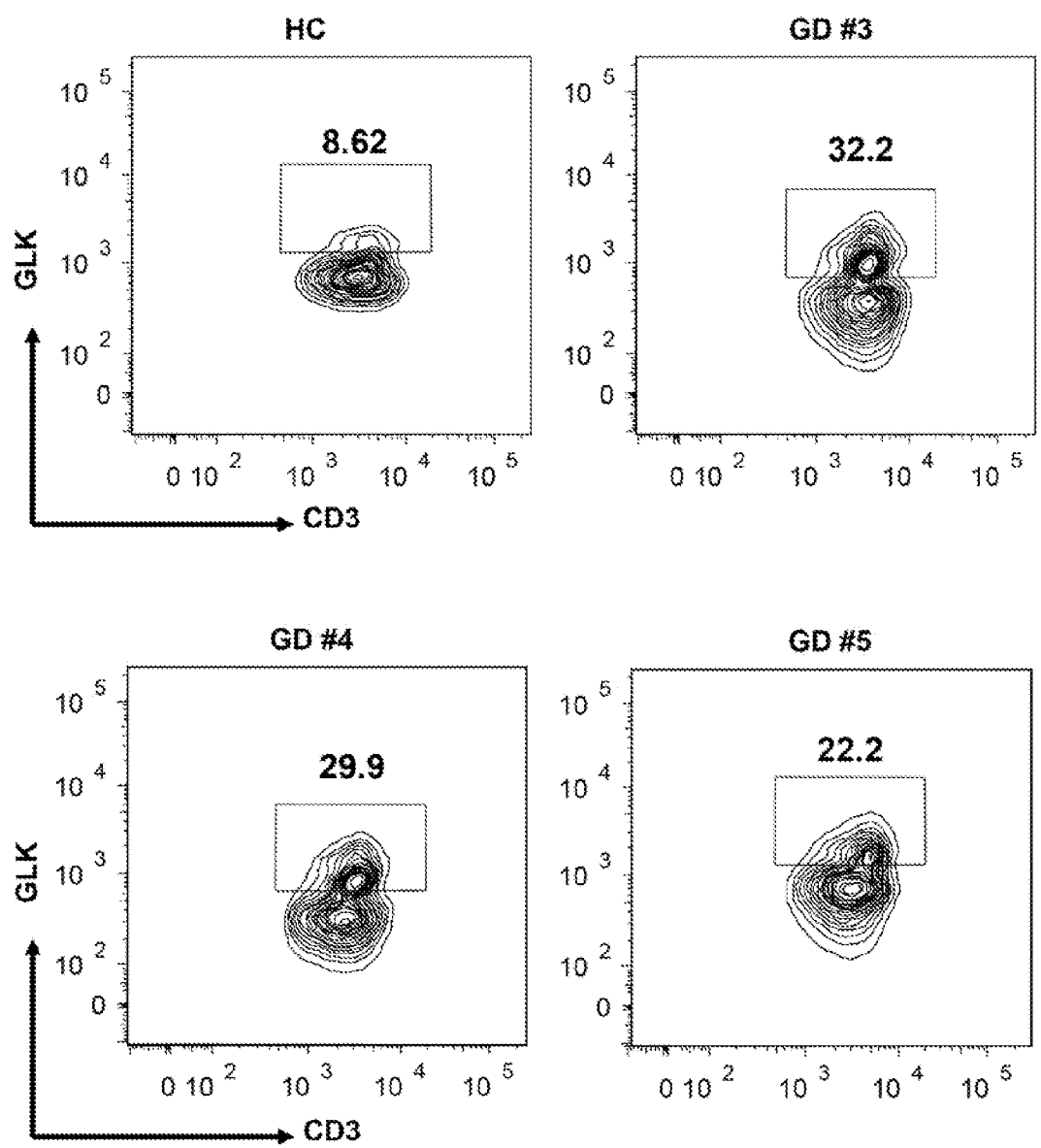

FIG. 26 shows increased percentages of GLK-positive T cells in Grave's disease patients. Flow cytometry analyses of GLK expressing T lymphocytes from peripheral blood of subjects with Grave's disease (GD) and healthy controls (HC).

Figure 27:
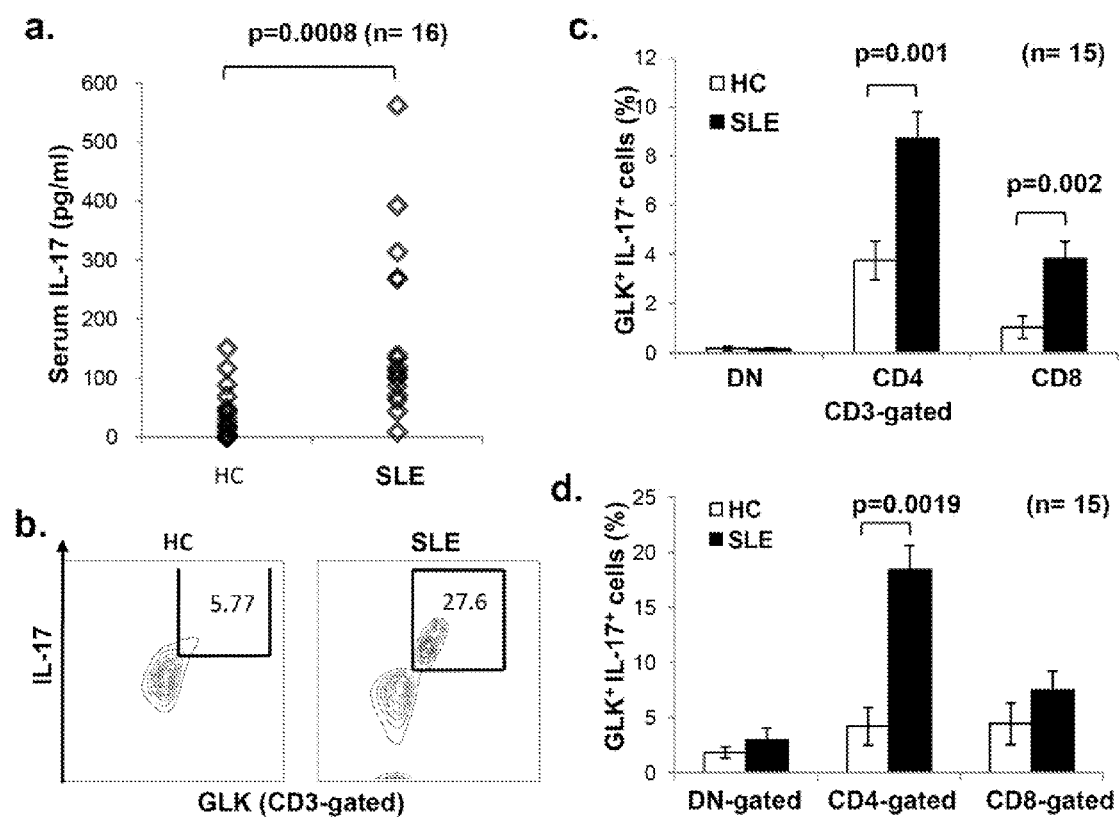

FIG. 27 shows that most GLK-overexpressing T cells are IL-17-producing cells, a. Serum IL-17 levels of SLE patients and healthy controls were determined by ELISA assays, b. Flow cytometry analyses of GLK/IL-17-double-positive T cells (CD3-gated) from the peripheral blood of a representative SLE patient (SLEDA1=12). c. The percentage of GLK/IL-17-double-positive cells in the T cells (CD3-gated) or in the T-cell subsets (individually gated) from HC and SLE patients, d. Double negative, CD4-positive, or CD8-positive T cells were gated and then GLK/IL-17-double-positive cells from the PBLs of SLE patient were analyzed by flow cytometry. The percentages of GLK/IL-17-double-positive cells in different subsets were shown.

Figure 28:
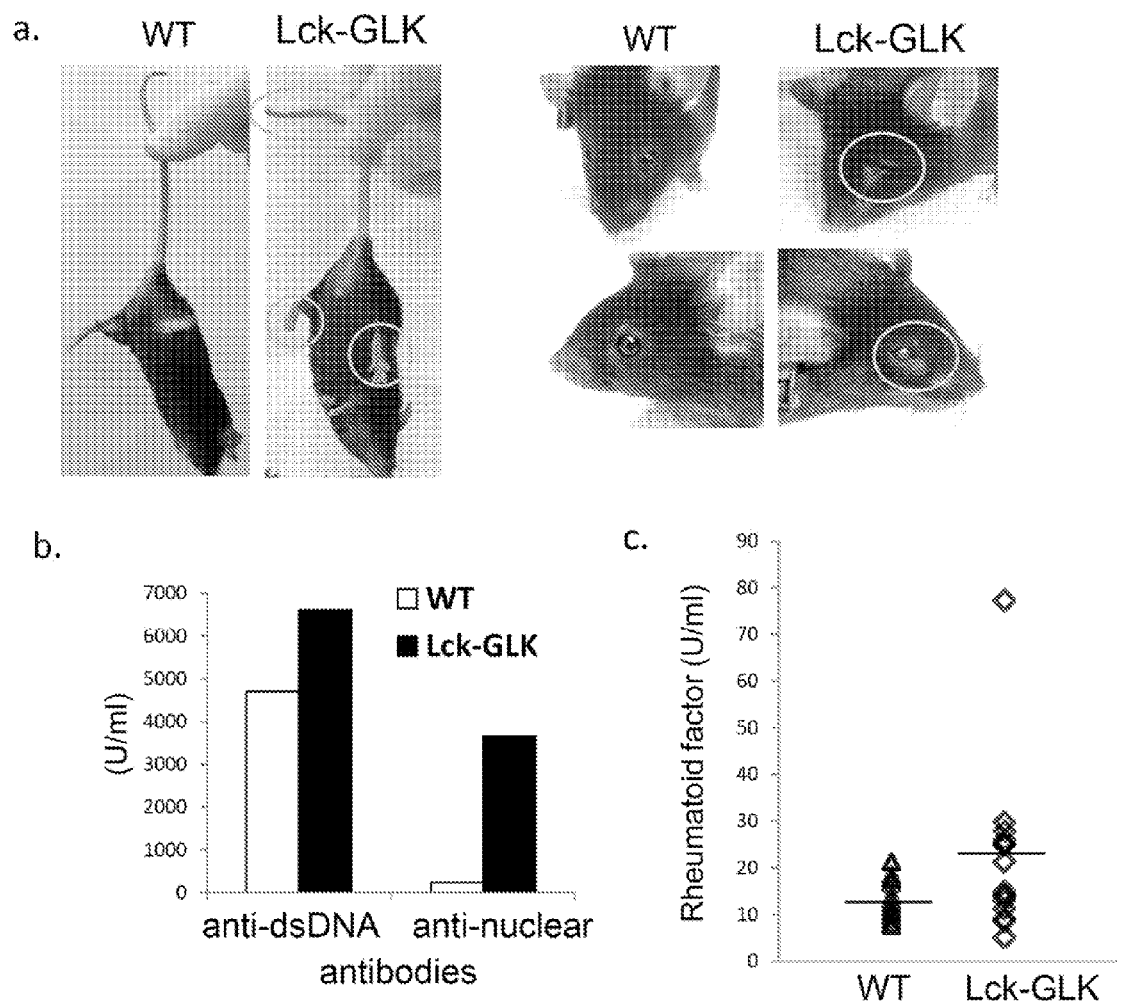

FIG. 28 shows that Lck-GLK transgenic (Tg) mice spontaneously develop autoimmune diseases, a. The phenotypes of Lck-GLK Tg mice: Most of Lck-GLK Tg mice displayed weak tails and hind legs. The Lck-GLK Tg mouse with high GLK expression died at 13-week old. Lck-GLK Tg mice suffered from a cataract and a blind eye. b. and c. Serum autoantibodies of Lck-GLK Tg mice were detected by ELISA assays. Anti-nuclear antibodies are indicative of SLE. Rheumatoid factor is indicative of RA.

Figure 29:
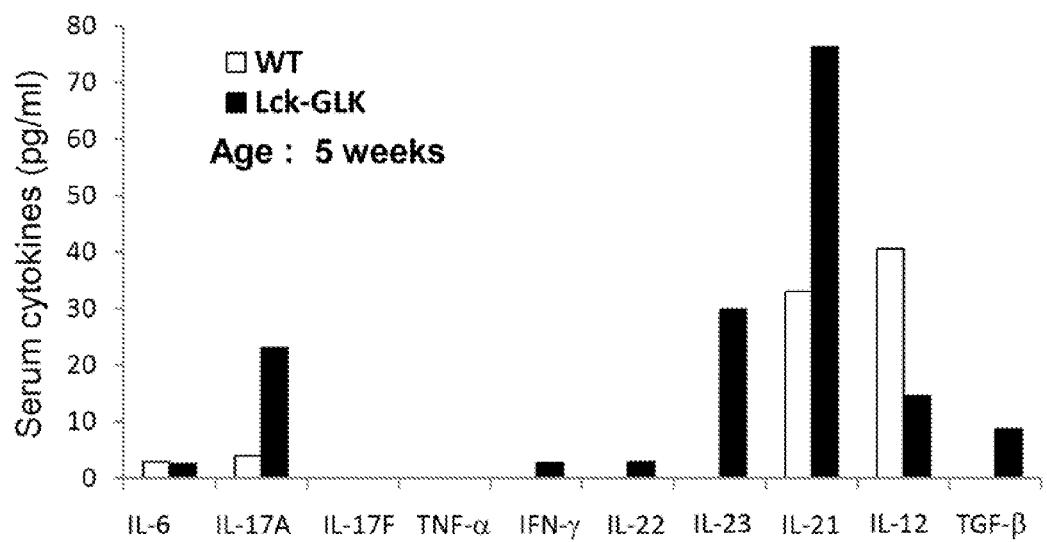
Figure 29:
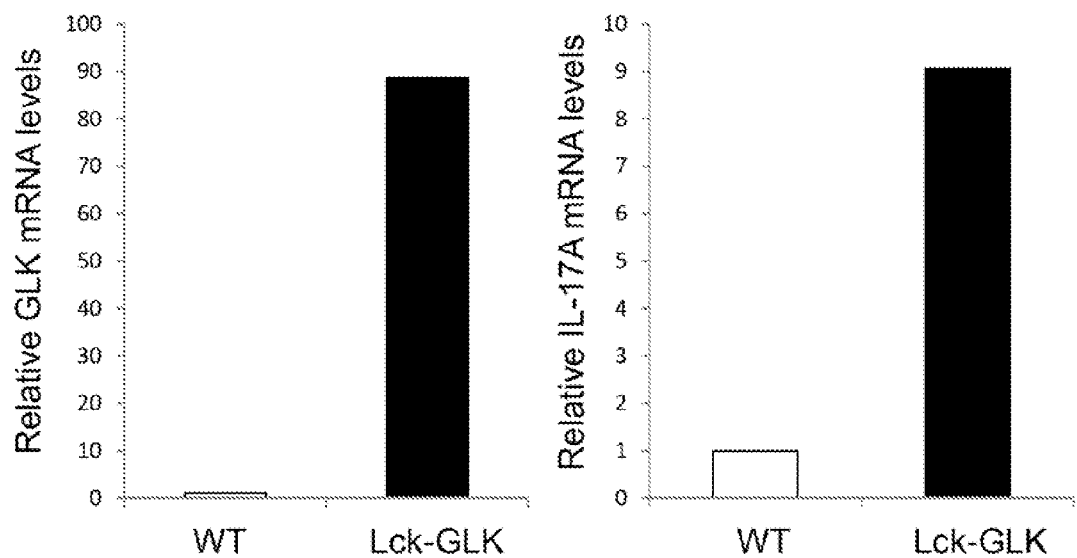

FIG. 29 shows that Lck-GLK transgenic (Tg) mice show increase of IL-17A levels, a. Serum cytokines of mice (5-week-old) were measured by ELISA assays (n=8). b. mRNA levels of GLK and IL-17A in peripheral T cells from pool Lck-GLK Tg mice were determined by Taqman probes using real-time PCR (n=6).

Figure 30:
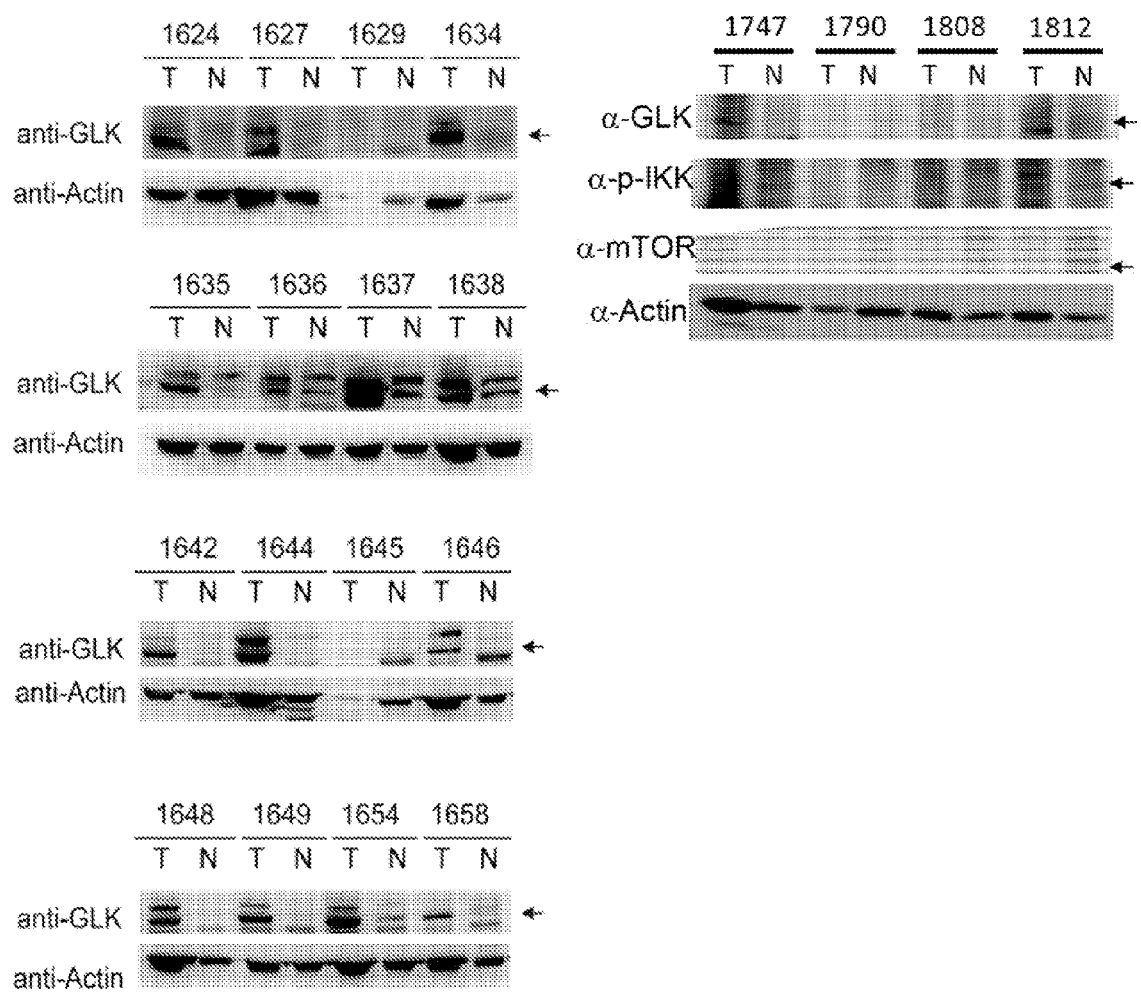

FIG. 30 shows GLK overexpression in non-small-cell lung carcinoma, Immunoblotting analyses of GLK, p-IKK, p-mTOR in the lung tissues from patients with lung cancer, n=20. T: tumor part; N: normal part.

Figure 31:
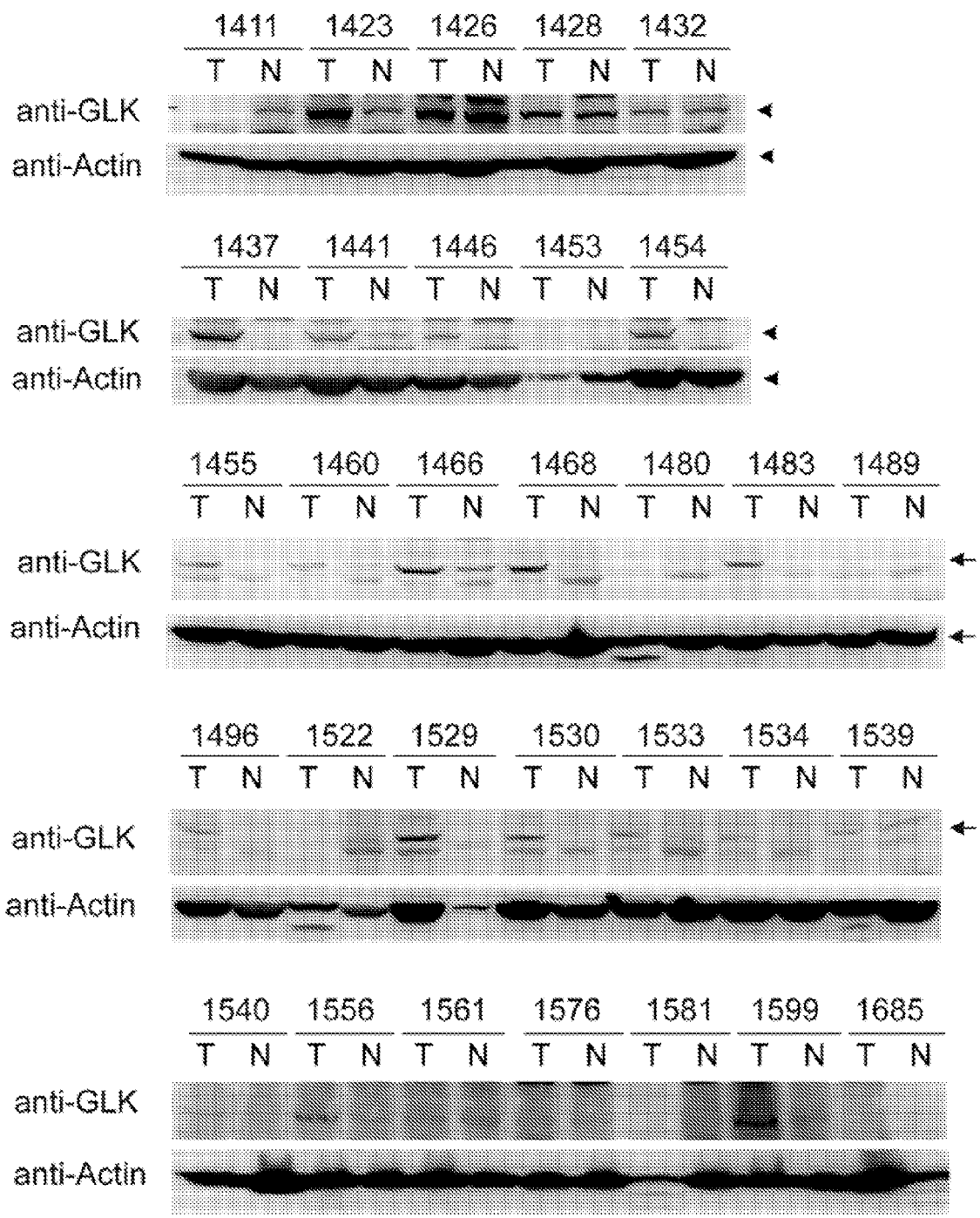

FIG. 31 shows GLK overexpression in esophageal cancer. Immunoblotting analyses of GLK in the esophageal carcinoma samples from patients, n=31. T: tumor part; N: normal part.

Figure 32:
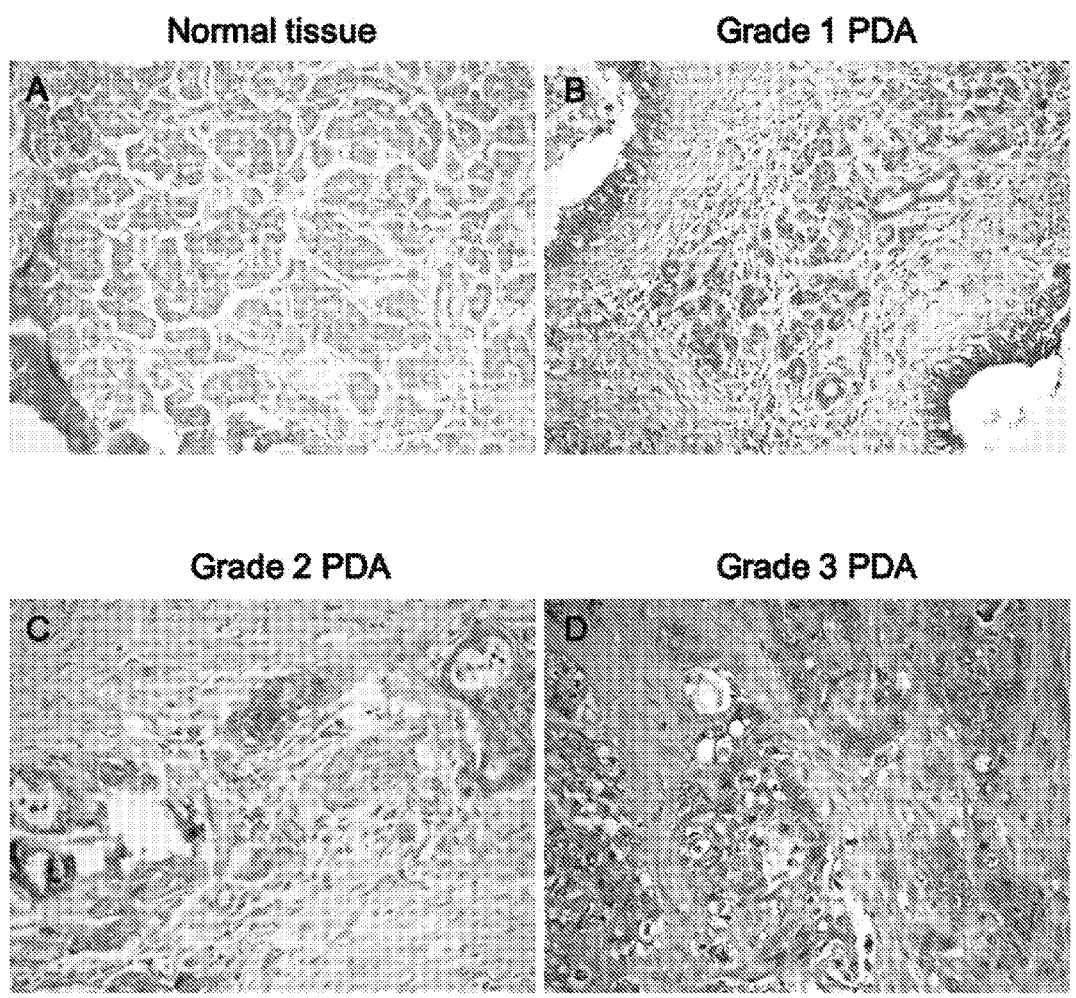

FIG. 32 shows GLK overexpression in pancreatic ductal adenocarcinoma. GLK staining in normal pancreas and pancreatic ductal adenocarcinoma (PDA). Representative images of (A) normal pancreas, (B) grade 1 PDA, (C) grade 2 PDA, and (D) grade 3 PDA are from paraffin-embedded tissues. Original magnification, X20.

Figure 33:
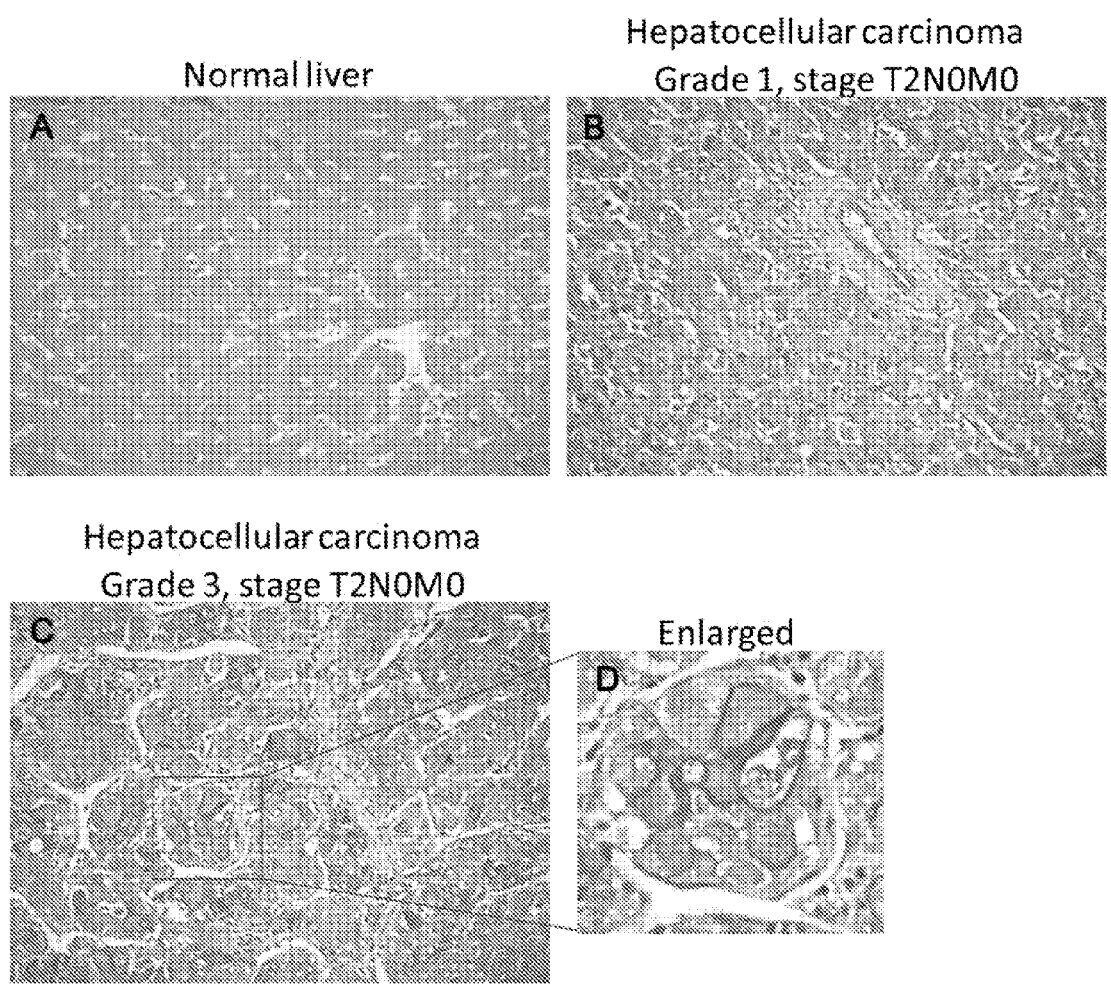

FIG. 33 shows GLK overexpression in hepatocellular carcinoma. GLK staining in normal liver and hepatocellular carcinoma. Representative images of (A) normal liver, (B) grade 1 hepatocellular carcinoma, (C) grade 3 hepatocellular carcinoma, and (D) Enlarged image of (C). Original magnification, X20.

Figure 34:
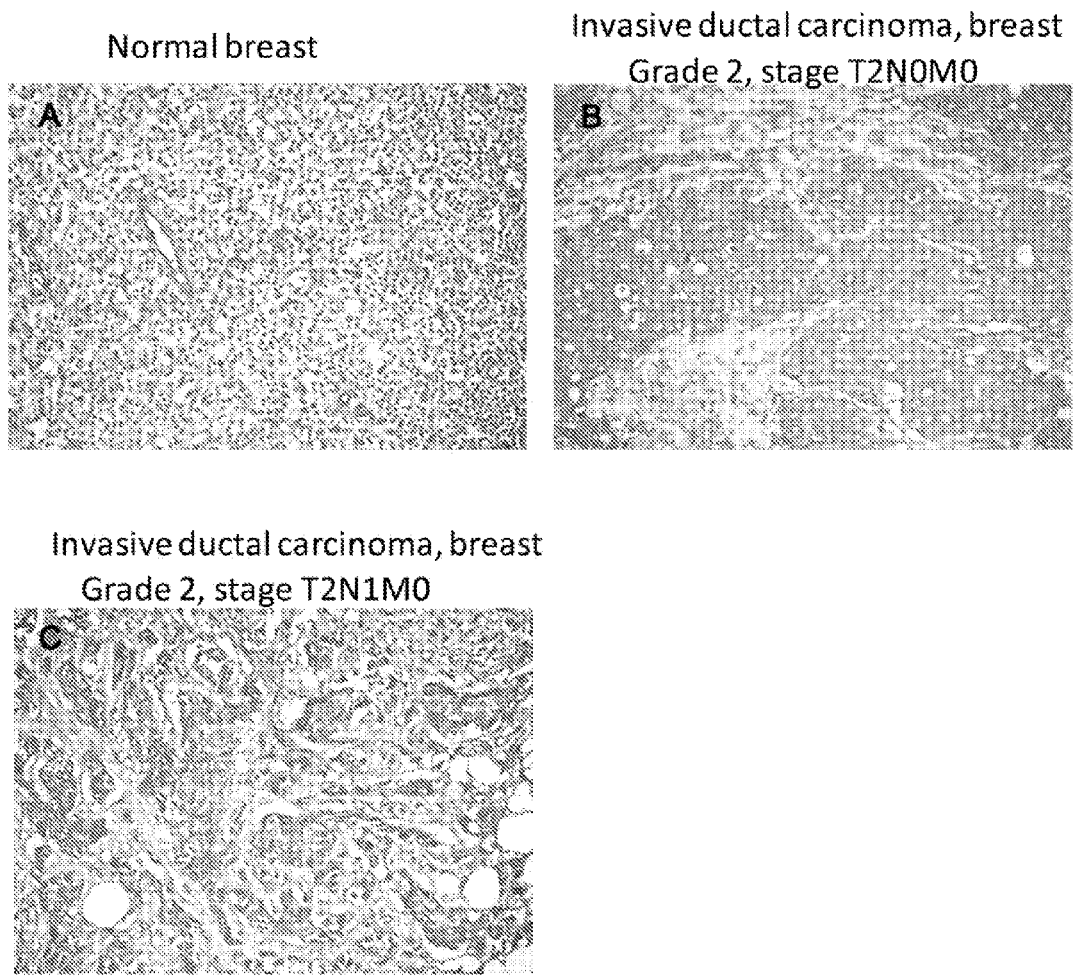

FIG. 34 shows GLK overexpression in breast carcinoma. GLK staining in normal breast and breast cancer. Representative images of (A) normal breast, (B) grade 2, stage T2N0M0 breast carcinoma, (C) grade 2, stage T2N1M0 breast carcinoma. Original magnification, X20.

Figure 35:
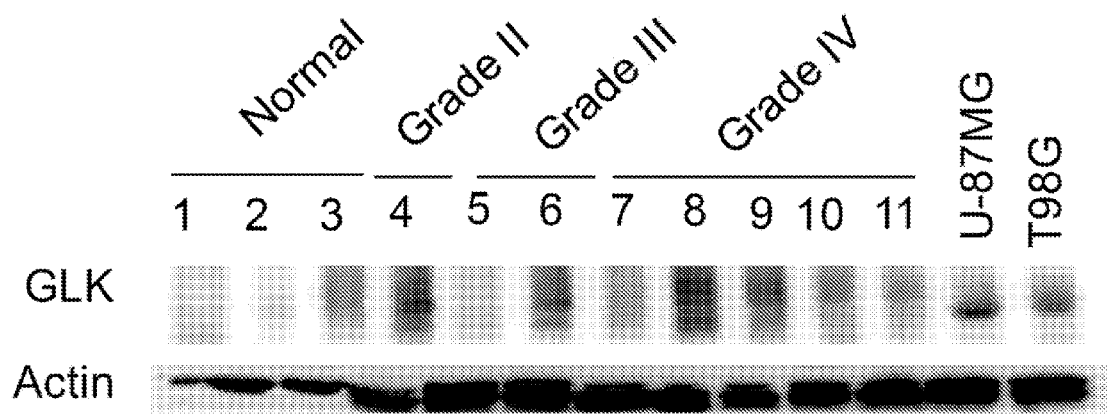

FIG. 35 shows GLK overexpression in glioblastoma. Immunoblotting analyses of GLK protein expression in normal brain tissue, human glioblastomas (grade II to IV), and two brain tumor cell lines (U-87MG and T98G).

Figure 36:
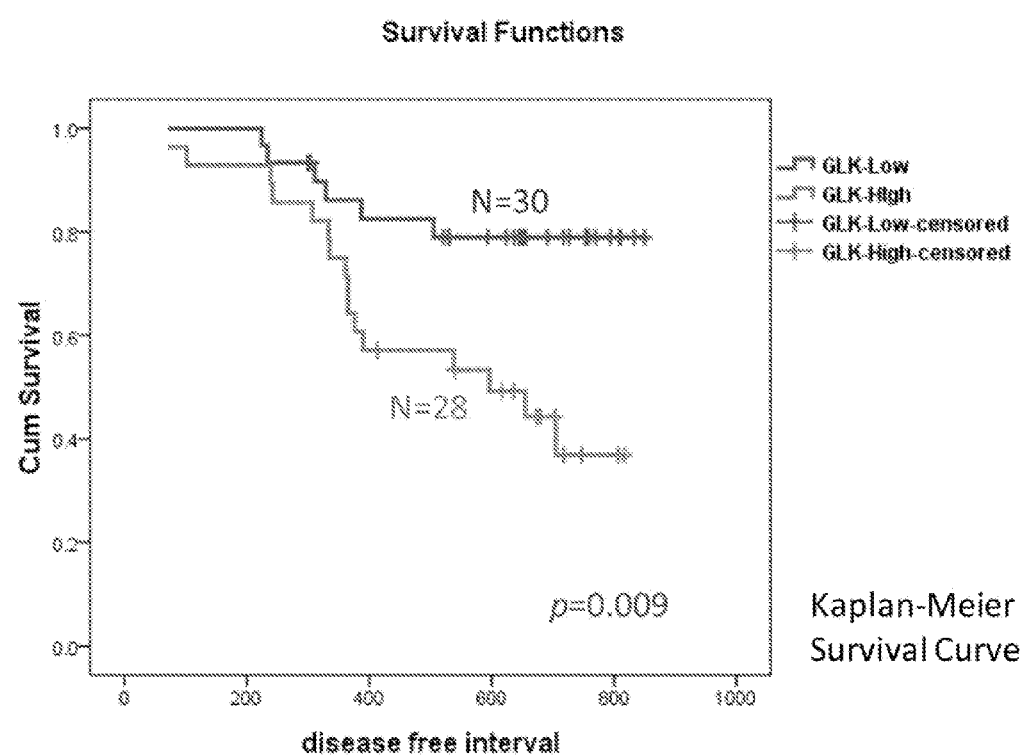

FIG. 36 shows high GLK protein expression predicts early recurrence in non-small-cell lung carcinoma patients. High GLK protein levels (GLK-high) were correlated with early recurrence in non-small-cell lung carcinoma (NSCLC) patients.

Figure 37:
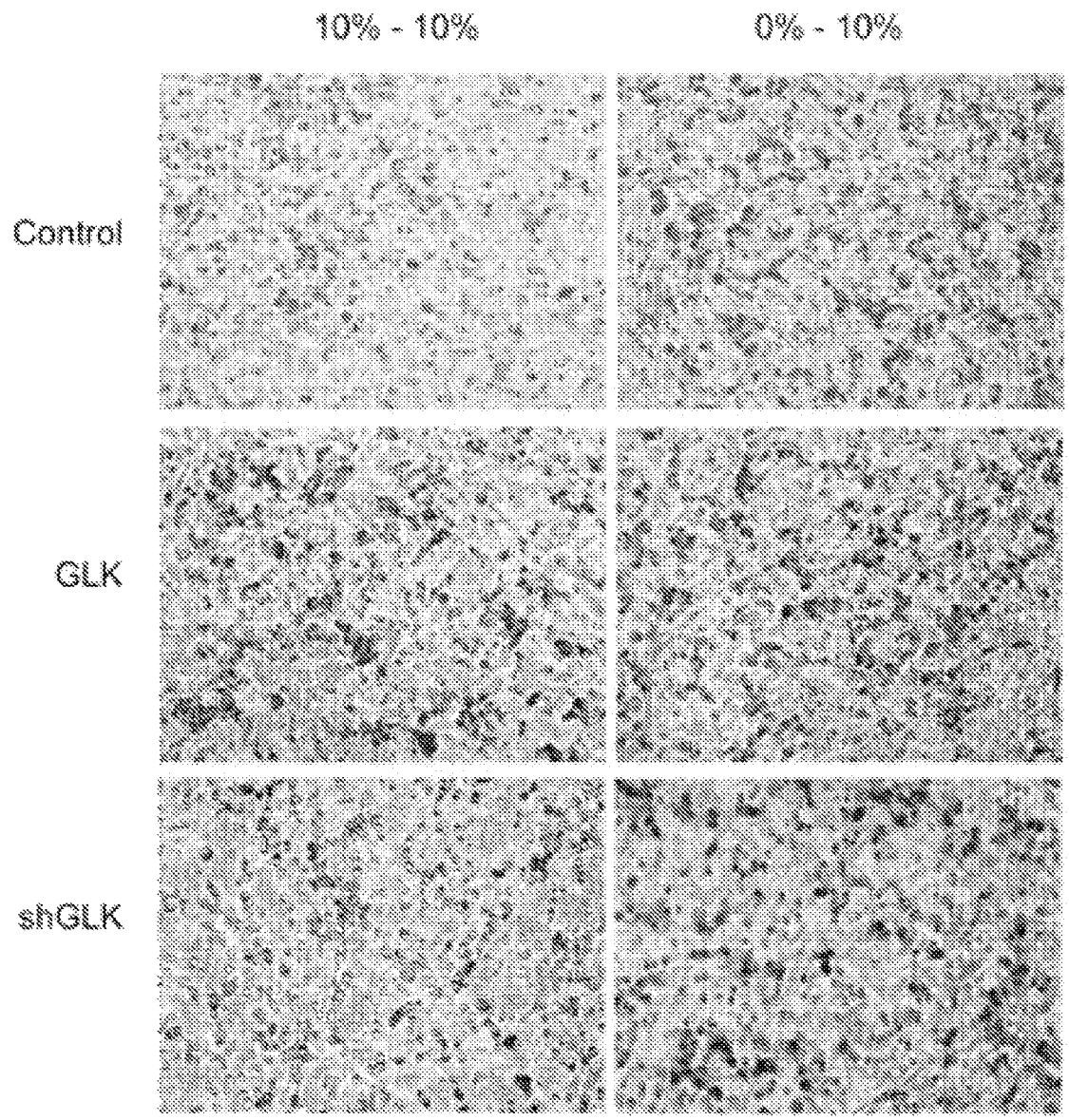

FIG. 37 shows GLK overexpression enhances spontaneous invasion. H1299 cells were transiently transfected with vector (upper panel), GLK (middle panel), or shRNA-GLK (lower panel) for 24 h. After transfection, these cells were examined by transwell assays. 10%-10% serum, spontaneous invasion. 0%-10% serum, serum-induced invasion.

Figure 38:
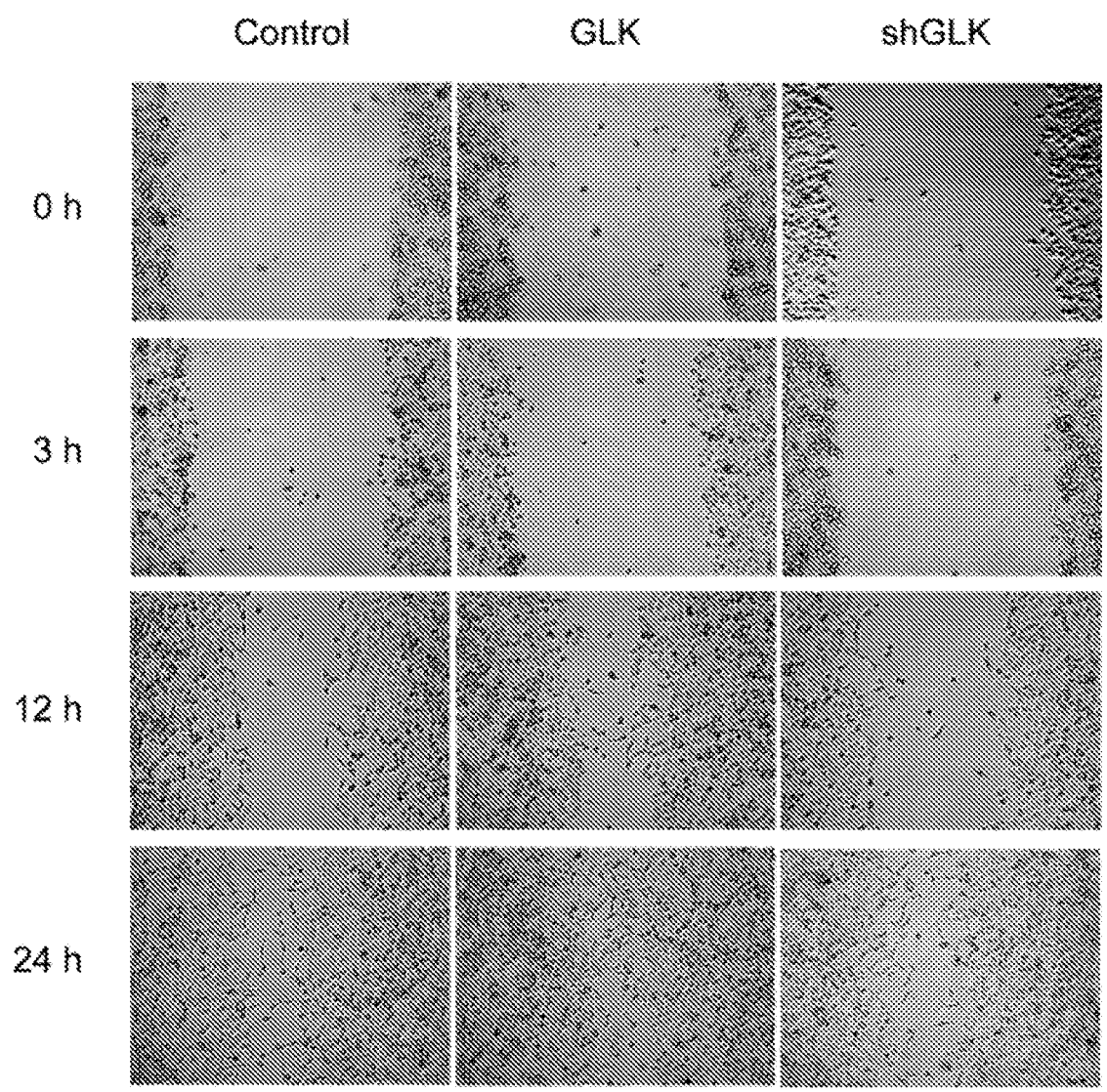

FIG. 38 shows overexpression of GLK promotes cell migration (wound healing). H1299 cells were transfected with the indicated plasmids and cultured until confluent. Scraped the cell monolayer in a straight line to create a "wound" with a p200 pipette tip and removed the debris of the wound by washing the cells with the growth medium. After the incubation for the indicated time points, obtained the images under a phase-contrast microscope.

Figure 39:
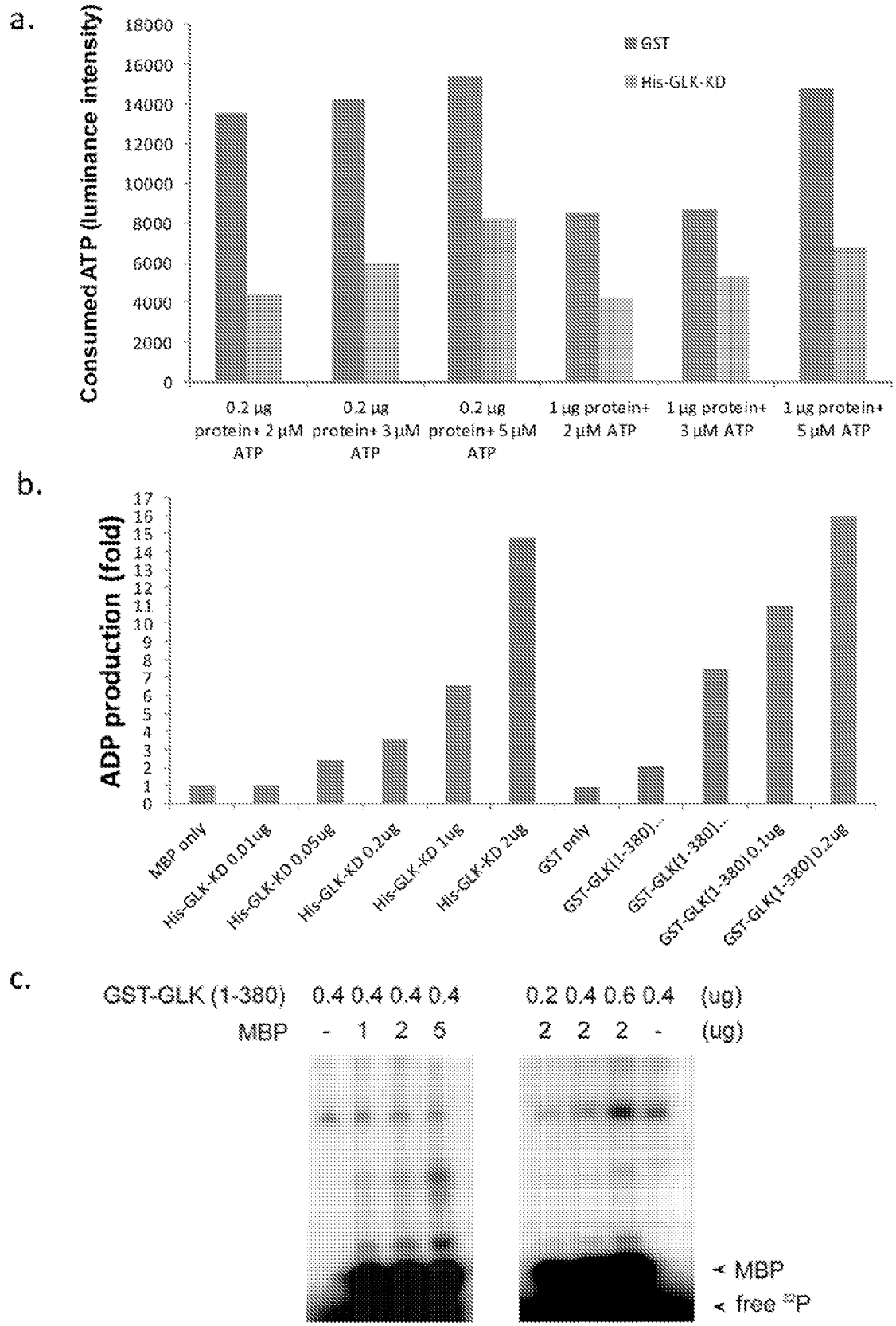

FIG. 39 shows in vitro kinase assays of GLK kinase domain (GLK-KD) recombinant proteins isolated from BL21 E. coli (His-GLK-KD) or from baculovirus in Sf9 insect cells (GST-GLK) using ATP-GLO™ kinase kit (a) or ADP-GLO™ kinase kit (b) or radioactive kinase assays (c).

FIG. 40 shows the interaction between GLK and PKC-θ. (a) FRET analysis of direct interaction between CFP-GLK and YFP-PKC-θ in transient transfected HEK293T cells, (b) Signals of the interaction between Flag-GLK and Myc- PKC-θ in lysates of transient transfected HEK293T cells determined by amplified luminescent proximity homogeneous assays (ALPHA).

DETAILED DESCRIPTION OF THE INVENTION

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "control", depending on the context, may refer to a healthy, normal sample or cells, or refer to a test performed in the absence of a test compound. A measurement obtained from the T cells of a patient subject is compared with a control measurement obtained from the T cells of a healthy, normal subject. A measurements obtained from cancer cells of a patient are compared with a control measurement obtained from non-cancer, normal cells from a non-tumor tissue sample of the same patient or of a healthy, normal subject.

The term "GLK signaling" refers to GLK-mediated signal transduction, i.e., GLK-PKC-θ-IKK-NF-κB-IL17A signal transduction.

FLAG-tag, or FLAG octapeptide, is a polypeptide protein tag that can be added to a protein using recombinant DNA technology. A FLAG-tag can be used in many different assays that require recognition by an antibody. The peptide sequence of the FLAG-tag is: N-DYKDDDDK-C. A myc tag is a polypeptide protein tag derived from the c-myc gene product that can be added to a protein using recombinant DNA technology. The peptide sequence of the myc-tag is: N-EQKLISEEDL-C.

When GLK and PKC-θ proteins are labeled with different, compatible fluorescent probes that allows fluorescence energy transfer from one fluorescent probe to another, the fluorescence energy transfer occurs when GLK binds to (i.e., physically associated with) PKC-θ protein. The first fluorescent probe has a lower excitation wave length, and the second fluorescent probe a higher excitation wave length. The emission wave length of the first fluorescent probe overlaps with the higher excitation wave length, and will thus excite the second fluorescent probe and cause an emission at a higher wave length. If a test compound interferes with GLK binding to PKC-θ, the fluorescent energy transfer will not occur and a higher wave length fluorescence emission will not occur.

The full names for abbreviations used herein are as follows: palindromic rheumatism (PMRA); phorbol-12-myristate-13-acetate (PMA); peripheral blood leukocytes (PBL); Germinal Center Kinase (GCK)-Like Kinase (GLK).

The invention relates to the discovery of the role of GLK in the TCR signaling cascade. It was found that GLK represents the kinase linking signal transduction from SLP-76 to PKC-θ.

The amino acid sequence of homo sapiens germinal center kinase related protein kinase (GLK) is SEQ ID NO: 1, and nucleotide sequence SEQ ID NO: 2. The amino acid sequence of rattus norvegicus mitogen-activated protein kinase kinase kinase kinase 3 (Map4k3) is SEQ ID NO: 3, and nucleotide sequence SEQ ID NO: 4. The amino acid sequence of protein kinase C, theta (human) is SEQ ID NO: 5 and nucleotide sequence SEQ ID NO: 6. The amino acid sequence of mus musculus protein kinase C, theta is SEQ ID NO: 7, and nucleotide sequence SEQ ID NO: 8.

Methods for Screening Compounds
Protein-Based Assays: Radioactive/Nonradioactive in Vitro Kinase Assays Radioactive in vitro kinase assay. Recombinant GLK proteins were incubated with 10 µCi of [γ-$^{32}$P] ATP, 4 µg myelin basic protein (MPB). and 500 µM cold ATP in 35 µl kinase buffer at room temperature for 40 min. Samples were separated by a 12% SDS-page; and the incorporation of radio-labelled phosphate into the substrate was quantified by Typhoon scanner.

Nonradioactive in vitro kinase assay. The nonradioactive in vitro kinase assay was carried out in 96-well. white Proxiplales (PerkinElmer, Boston, Mass.) in a total volume of 100 µl. To determine the levels of ADP generated after GLK kinase reactions, recombinant GLK proteins (2 µg; isolated from either E. coli or baculovirus-infected Sf9 insect cells) were incubated with 10 µg MPB, and 2 µM ATP in 25 µl kinase buffer at room temperature for 40 min. ADP-Glo™ Reagent (25 µl; Promega) was added. After incubating for 40 min, Kinase Detection Reagent (50 µl) was subsequently added and incubated for 30 min. Luminance intensity was measured by an EnVision multilabel reader (PerkinElmer life Science). To determine the levels of ATP consumed after GLK kinase reactions, recombinant GLK proteins (0.2-1 µg) were incubated with 10 µg MPB, and 2 µM ATP in 25 µl kinase buffer at room temperature for 40 min. ATP-Glo™ Reagent (25 µl; Promega) was added incubated for 10 min. Luminance intensity was measured by an En Vision multilabel reader (PerkinElmer life Science).

Cell-based assays: Drug screening using stable GLK-transfected cells determined by IL-17A ELISA, or NF-κB activity reporter assays.

Establish stable GLK-transfected cells. Jurkat cells were transfected with GLK plasmid and P-NF-κB-Luc-hygromycin plasmid using Neon Transfection System (invitrogen Corporation). To select stable GLK-transfected cells, GLK-transfected cells were cultured in RPMI-1640 containing neomycin at least for 2 weeks.

IL-17A enzyme-linked immunosorbent assay (ELISA). Stable GLK-transfected Jurkat cells ($10^6$ per well in 96-well dish) were incubated in RPMI medium (200 µl) for 72 h. The levels of IL-17A in the supernatants were determined by human IL-17A ELISA (PeproTech).

NF-κB activity of luciferase reporter assay. $10^6$ stable GLK-transfected Jurkat cells were resuspended in 60 μl RPMI medium plus 60 μl lysis/Luciferase buffers (Promega). Data represent the mean of firefly-luciferase activity with S.D. error bar.

Transwell migration and invasion assay. Transwell migration assays were used $1 \times 10^5$ cells plated in a non-coated top chamber (24-well insert; pore size 8 μm; Corning Costar) and cultured for 16 h. Invasion assays were used $1 \times 10^5$ cells onto the Matrigel-coated lop chamber (BD Bioscience) and incubated for 24-48 h. Scrape off noninvaded cells that remained on the upper side of the transwell with a cotton swab. Cells on the lower side of the insert filler were quickly fixed by 4% paraformaldehyde for 10 min and then stained with 1% crystal violet for 20 min. Count the number of the cells on the lower side of the filter under a light microscope. Results are expressed as a number of migrating or invasive cells per ten fields.

Wound healing assay (cell migration). Human lung carcinoma H1299 cells are transfected with vector (empty without transgene), pClneo-GLK (plasmid with GLK transgene), or shRNA-GLK (plasmid with shRNA of GLK transgene). These cell monolayers should be absolutely confluent. Two parallel scratch wounds are made with a p200 pipette tip. The wounds are observed using phase contrast microscopy. Images are taken at regular intervals over the course of 0-24 h of both areas flanking the intersections of the wound:

Protein-Protein Interaction Assays:

Fluorescence resonance energy transfer (FRET) assays and Amplified luminescent proximity homogeneous assays (ALPHA; PerkinElmer).

Fluorescence resonance energy transfer (FRET) assays. HEK293T cells were transfected with CFP-GLK and YFP-PKC-θ plasmids, and the fluorescence intensities were determined using EnSpire 2300 Multilabel Reader (Perkin Elmer) 24 h later. The CFP was excited at 432 nm; the resulting fluorescence intensity emitted at 485 nm was measured. The YFP was excited at 485 nm; the resulting fluorescence intensity emitted at 540 nm was measured. The FRET signal was excited at 432 nm; the resulting fluorescence intensity emitted at 540 nm was measured.

Amplified luminescent proximity homogeneous assays (ALPHA). The AlphaScreen binding assay was carried out in 384-well, white Proxiplates (Perk in Elmer, Boston, Mass.) in a total volume of 20 μl. The AlphaScreen Flag detection kit was from PerkinElmer Life Science. The AlphaScreen donor beads were supplied as Flag-coated, and the acceptor beads were conjugated to an anti-Myc antibody. Purified Flag-GLK plus Myc-PKC-θ or Flag-SLP-76 plus Myc-GLK were mixed together in 384-well plates (5 μl/well). If HEK293T transfectants were used, 0.2 μg lysates were added per well. Acceptor beads (5 μl/well) were added and incubated for 30 min. Donor beads (5 μl/well) were subsequently added and incubated for 3 h. The ALPHA signals were determined by an EnVision multilabel reader (PerkinElmer life Science). The final concentrations of donor and acceptor beads were 20 μg/ml. All dilutions were made in HEPES buffer (10 mM HEPES, 150 mM NaCl. 0.05% Tween-20, 0.5 mM DTT).

It was discovered that GLK overexpression is associated with cancer and metastasis. Such GLK-mediated cancer and metastasis does not involve mammalian target of rapamycin (mTOR). The invention relates to the discovery of GLK-PKC-θ-IKK-NFκB-1L-17 signal transduction pathway useful as a cancer prognosis biomarker and therapeutic target for GLK-mediated disease.

In one aspect, the invention relates to a method for identifying a therapeutic agent for treating a Germinal Center Kinase (GCK)-Like Kinase (GLK)-mediated disease. The method comprises detecting a modulation of GLK-mediated signal transduction by a test compound, in which the detecting step comprises: a) culturing GLK-expressing cells in the presence of the test compound, wherein said modulation is detected by measuring the expression level of GLK transcripts or protein, the amount of IL-17A produced or the activity of NF-κB; orb) allowing a GLK protein to react at the presence of ATP with a substrate thereof in the presence of the test compound, wherein said modulation is detected by measuring the amount of ADP produced, the amount of ATP consumed and/or the amount of the substrate being phosphorylated; or c) culturing GLK-expressing cancer cells in the presence of the test compound, wherein the modulation is detected by measuring migration/invasion/wound healing of said cancer cells; or d) allowing a GLK protein to interact with a substrate protein thereof in the presence of the test compound, wherein said modulation is detected by measuring the interaction between the GLK and the substrate protein; and e) comparing said modulation in the presence of the test compound with a control identifies a therapeutic agent for treating a GLK-mediated disease. The interaction between GLK and the substrate proteins (such as PKC-θ protein) may be measured by using fluorescence resonance energy transfer (FRET) assays or amplified luminescent proximity homogeneous assays.

In the aforementioned step d), the substrate may comprise a PKC-θ protein and said GLK and PKC-θ proteins are labeled with different, compatible fluorescent probes, one probe with fluorescence excitation and emission wave lengths higher than the other probe, and said modulated association is detected by a change at a higher fluorescence emission wave length.

The ATP may be either non-radioactive or labeled with a radioisotope. The interaction of the GLK protein and the substrate may be allowed to occur within a cell or in a test lube in vitro. The GLK-mediated disease may be selected from the group consisting of an autoimmune disease, an inflammatory disease, cancer and cancer metastasis. The substrate may be selected from the group consisting of PKC-θ protein and myelin basic protein (MBP). The test compound may be selected from the group consisting of an RNAi molecule, microRNA, an antisense molecule, and a small organic molecule. The GLK-expressing cells may comprise GLK-expressing T cells, and/or GLK-expressing cancer cells may comprise GLK-expressing lung cancer cells. The GLK-expressing cells may comprise GLK-overexpressing cells such as GLK-overexpressing T cells, and/or GLK-expressing cancer cells may comprise GLK-overexpressing cancer cells such as GLK-overexpressing lung cancer cells.

The autoimmune disease may be selected from the group consisting of systemic lupus erythematosus, rheumatoid arthritis, adult-onset Still's disease, Graves' disease, Sjogren's syndrome, ankylosing spondylitis, neuromyelitis optica, autoimmune encephalomyelitis, and alopecia. The cancer may be selected from the group consisting of lung carcinoma, esophageal carcinoma, glioblastoma, pancreatic cancer, breast cancer, and hepatoma. In one embodiment of the invention, said cancer is a type of GLK protein-mediated cancer and independent of (or does not involve) mammalian target of rapamycin (mTOR) protein.

In another aspect, the invention relates to a method for detecting the presence and/or severity, of a Germinal Center Kinase (GCK)-Like Kinase (GLK)-mediated disease. Detecting the presence and/or severity of GLK-mediated disease may comprise determining the prognosis of a cancer, such as lung cancer. The method comprises: a) obtaining a sample comprising T cells or cancer cells from a subject suspected of having a GLK-mediated disease or cancer; b) measuring the expression level of GCK-like kinase (GLK) in the T cells or in the cancer cells; and c) determining the presence and/or severity of the GLK-mediated disease; wherein an increase in the expression level of GLK in the T cells or in the cancer cells as compared with the expression level of GLK in a control is an indication that the subject is at risk of developing or having the GLK-mediated disease, or at risk of recurrence and/or metastasis of the cancer. The determining step may comprise determining the prognosis of the cancer. In one embodiment of the invention, the increase in the expression level of GLK in the cancer cells is independent of mammalian target of rapamycin (mTOR) protein.

The measuring step may comprise measuring the expression level of GLK protein in the T cells, and/or performed by immunoblotting analyses, flow cytometry analyses, and/or immunohistochemistry. Alternatively, the measuring step may comprise measuring the expression level of GLK transcript, which may further comprises normalizing the measured expression level of GLK transcript to a housekeeping gene to obtain a normalized expression level of GLK transcript.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

I. GLK Controls Autoimmunity and NF-κB Signaling by Activating PKC-θ in T Cells

Methods and Materials

GLK-deficient mice. A 129 mouse embryonic stem cell clone with GLK knockout (clone RRO270) was purchased from EUCOMM and injected into C57BL/6 blastocysts to generate chimeric mice at the Transgenic Mouse Model Core, National Research Program for Genomic Medicine, Taiwan. All animal experiments were performed according to protocol approved by the IACUC at the National Health Research Institutes.

Patients and healthy controls. Forty-nine patients diagnosed with systemic lupus erythematosus (SLE) based on American College of Rheumatology criteria were studied. All patients were referred to the Division of Allergy, Immunology, and Rheumatology at Taichung Veterans General Hospital (TVGH). Thirty-five healthy individuals were enrolled as the control. The study was approved by the Institutional Review Board of TVGH, and written informed consent was obtained from all individuals.

Antibodies, plasmids and purified proteins. The anti-mouse CD3ε (I45-2C11) and anti-human CD3ε (OKT3) were purified from mouse ascites by protein A-Sepharose chromatography. Antibodies for GLK, HPK1, p-Erk (T202/Y204), Erk, p-SLP-76 (S376), and SLP-76 were generated by immunizing rabbits with individual peptides. Anti-p-PKC-θ (T538) and anti-p-PKC-θ (S695) antibodies were from Upstate Biotechnology, Inc. Anti-PKC-θ (C-19), anti-p-PKC-θ (S676), anti-Vav1 (D-7), anti-Vav2 (E-12), and anti-Vav3 (K-19) antibodies were from Santa Cruz Biotechnology, Inc. Anti-Flag (M2), anti-Myc, anti-HA, and anti-tubulin antibodies were from SIGMA. Anti-p-IKK (S181), anti-p-PDK1 (S214), anti-IKK, and anti-PDK1 antibodies were from Cell Signaling. Anti-p-PKC-θ (T538) (19/PKC) antibody for intracellular staining was from BD Pharmingen. Anti-p-mTOR and anti-mTOR antibodies were from Abcam.

The expression plasmids for GLK, GLK kinase-dead (KD) mutant, and Flag-SLP-76 were as described previously. Myc-tagged PKC-θ, HA-tagged GLK and GFP-tagged GLK were constructed by subcloning the individual cDNA into pCMV6-AC-Myc, pCMV6-AC-HA, and pCMV6-AC-GFP vector (OriGene Technologies), respectively. The shRNA plasmids were established by the National RNAi Core Facility. NF-κB reporter plasmid (pNF-κB-Luc) and normalized plasmid (pRL-TK) were purchased from Promega.

For in vitro binding assays, purified GLK and SLP-76 were isolated from Flag-GLK-transfected and Flag-SLP-76-transfected HEK293T cells, respectively, followed by Flag-peptide elution. Purified recombinant GST-PKC-θ expressed from baculovirus in Sf9 insect cells was purchased from SignalChem.

Transient transfection and T cell activation. For transient transfection assays, cells were transfected using Neon Transfection System (Invitrogen Corp.). The specific settings for individual cell lines or primary cells were as follows: 1420 V, duration of 30 ms. and 1 pulse for Jurkat T and J14 cell lines; 1080 V, duration of 50 ms, and 1 pulse for EL4 cells; 2000V, duration of 20 ms, and 2 pulses for primary T cells. To induce T cell activation, J-TAg and EL4 cells were stimulated with 5 µg/ml anti-CD3 antibodies for indicated time at 37° C. To induce primary T cell activation, $3 \times 10^6$ purified T cells were stimulated with 3 µg/ml anti-CD3-biotin (500A2; eBioscience) plus 3 µg/ml streptavidin (SIGMA).

In vitro kinase assays. Flag-GLK was immunoprecipitated from unstimulated or anti-CD3-stimulated Jurkat T or J-14 cell lysates (80 µg) using anti-Flag agarose beads. Anti-Flag immunoprecipitates were either washed three limes with lysis buffer plus one time with kinase buffer or subjected to Flag peptide elution for purification of Flag-GLK. Anti-Flag-GLK beads or purified Flag-GLK were incubated with 500 µM cold ATP, 4 µg myelin basic protein, and with or without 10 µCi of [γ-$^{32}$P]ATP in 35 µl kinase buffer at room temperature for 40 min. Samples were separated by SDS-PAGE. The phosphorylation of the substrate was detected by immunoblot analyses or the incorporation of radio-labelled phosphate into the substrate, which was quantified by Typhoon scanner (GE).

Flow cytometry analyses. Cells were stimulated with PMA plus ionomycin for 2 h, and treated with Golgi-stop for another 2 h. Cells were harvested, washed with cold PBS, and stained with indicated antibodies for 30 min on ice. For clinical sample analyses, PBLs were immediately treated with Golgi-stop without any other stimulation and then stained with anti-surface markers at the room temperature. For intracellular staining, PBLs were permeabilized in 200 µl Cytofix/Cyioperm buffer (BD Biosciences) for 2 h and washed with Perm-Wash buffer, and then incubated in antibodies (1:50 dilution) for 2 h. The following antibodies were used for staining: anti-mCD3-APC (145-2C11), anti-mCD3-FITC (145-2C11), anti-Foxp3-PE (150D), anti-IFNγ-FITC (XMG1.2), anti-IL-4-PE (11B11) and anti-IL-17A-PE (TC11-18H10.1) antibodies were purchased from BioLegend; and anti-mCD4-pacific blue (RM4-5), anti-hCD3-PECy7 (SK7), and anti-hCD19-PE (SJ25C1) antibodies were purchased from BD Pharmingen. Data were collected using FACSCanto II flowcytometer (BD Biosciences) and analyzed by FlowJo software.

In vivo T cell-mediated immune responses and induction of EAE. Mice used in each experiment were 6-10-week-old sex-matched littermates. The production of antigen-specific (KLH) antibodies, $T_H1$ and $T_H2$ cytokines from immunized mice was measured as previously described. The induction of EAE was done as described.

In vitro T-cell differentiation assays. $CD4^+$ $CD25^-$ cells were purified from lymph node of mice. Cells ($2.5 \times 10^5$) were cultured in 500 µl medium in 48-well plates coated with anti-CD3 (2 µg/ml) and anti-CD28 (3 µg/ml) antibodies. For $T_{reg}$ differentiation, cells were cultured in the medium containing 10 ng/ml IL-2, 10 ng/ml TGF-β, 2.5 µg/ml anti-IL4 and 2.5 µg/ml anti-IFN-γ antibodies. For $T_H17$ differentiation, cells were cultured in the medium containing 20 ng/ml IL-6, 5 ng/ml TGF-β, 50 ng/ml IL-23, 5 µg/ml anti-IL4 and 5 µg/ml anti-IFN-γ antibodies. For $T_H1$ differentiation, cells were cultured in the medium containing 5 ng/ml IL-12 and 1 µg/ml anti-IL4 antibodies. For $T_H2$ differentiation, cells were cultured in the medium containing 10 ng/ml IL-4 and 1 µg/ml anti-IFNγ antibodies.

In vitro suppression assays. Mouse $CD4^+$ T cells were negatively selected from the spleen and lymph nodes of mice, in second round of purification, $CD4^+$ $CD25^+$ T ($T_{reg}$) cells were isolated from the $CD4^+$ T cells using magnetically coupled antibodies against mouse CD25. $T_{reg}$ cells were added to $CD3^+$ T cells (final concentration of $2 \times 10^5$ cells/500 µl), and then stimulated with anti-CD3 antibodies for 72 h.

Statistical methods. P values were determined by Student's t-test. For analyses of data derived from clinical samples, Pearson correlation (r) was initially employed. Simple linear regression for flow cytometry data of clinical samples was employed to show statistically significant correlation between the percentage of GLK-expressing T cells and SLE-DAI of SLE patients.

Results:
GLK Directly Phosphorylates and Activates PKC-θ

Figure 1:
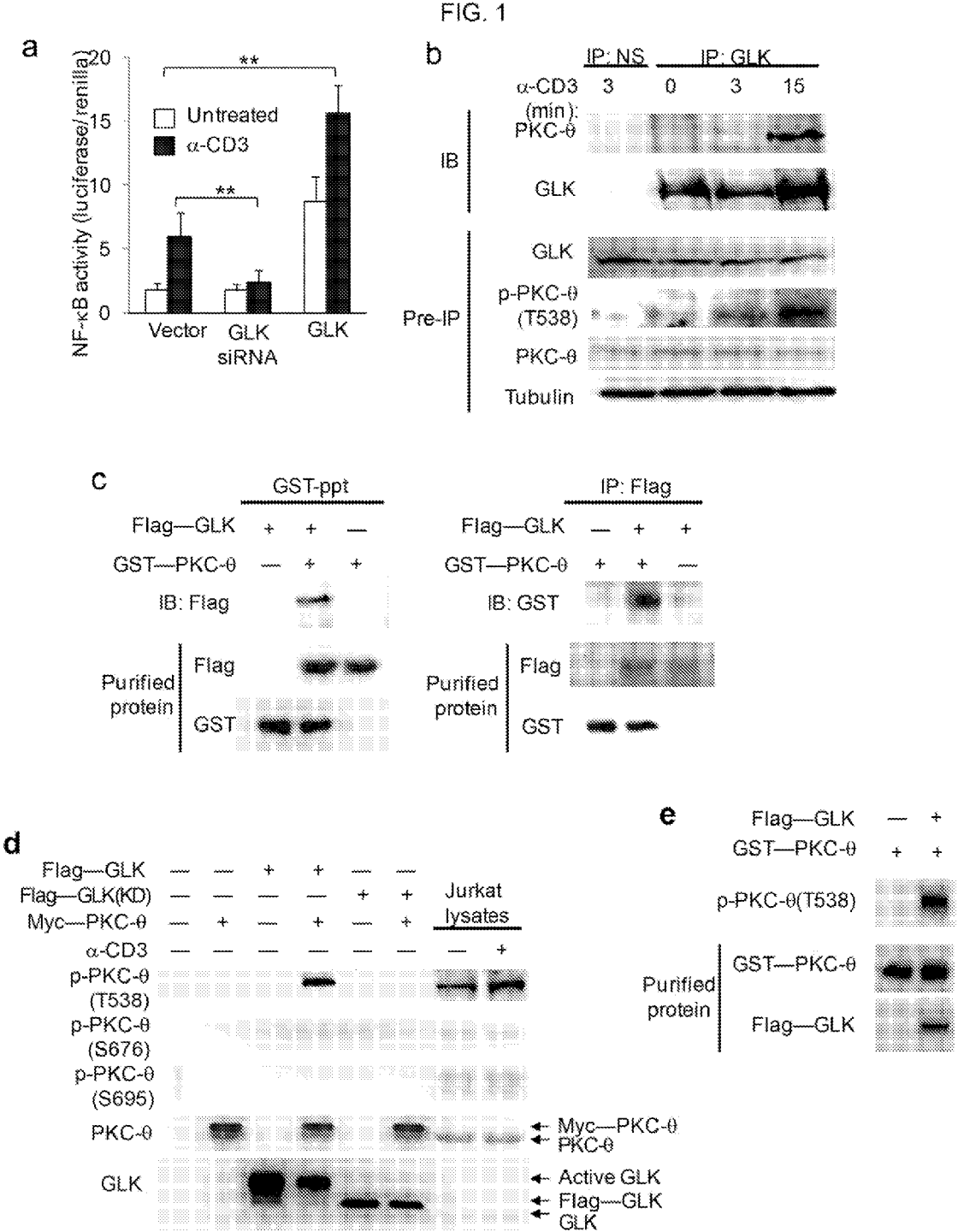
FIG. 1 shows that GLK directly interacts with and phosphorylates PKC-θ at T538. (a) Luciferase activity for NF-κB reporter assays in Jurkat T cells transfected with GLK siRNA or plasmid encoding GLK. Error bars are standard deviations (s.d.) of triplicate samples, (b) Co-immunoprecipitations (IP) of endogenous GLK with PKC-θ in lysates of mouse primary T cells following CD3 stimulation. NS, normal serum. IB, immunoblot. (c) In vitro binding assays of purified Flag-GLK and GST-PKC-θ proteins, ppt, precipitation, (d) Immunoblot analyses of GLK expression and GLK-induced PKC-θ phosphorylation in in vitro kinase assays using Flag-GLK and Myc-PKC-θ (as substrate) isolated from transfected HEK293T cells. Immunoblot analyses of PKC-θ in lysates of Jurkat cells are shown as control bands (right two lanes), (e)

We studied the role of GLK in TCR signaling by GLK overexpression or GLK siRNA knockdown in Jurkat T cells following by anti-CD3 stimulation (FIG. 1a and FIG. 6). Anti-CD3-induced NF-κB activity and IKK phosphorylation, but not Erk or mTOR activation in Jurkat T cells were suppressed by GLK siRNA or a kinase-dead (KD) mutant of GLK and were enhanced by GLK overexpression (FIG. 1a and FIG. 7a,b). Moreover, GLK kinase activity was induced by TCR signaling at 1 min and peaked at 30 min (FIG. 7c). These findings suggest that GLK is involved in TCR-induced NF-κB activation. Because SLP-76 regulates both Erk and IKK pathways, SLP-76 was unlikely to be the target of GLK. We thus examined the effect of GLK on the activation of PKC-θ, a critical regulator upstream of IKK-NF-κB and downstream from SLP-76 in TCR signaling. PKC-θ phosphorylation was regulated by GLK (FIG. 7d); therefore, we examined whether GLK activated the IKK-NF-κB pathway by targeting PKC-θ. PKC-θ siRNA knockdown abolished GLK-induced NF-κB activation upon anti-CD3 stimulation (FIG. 7e), indicating that GLK targets PKC-θ to induce NF-κB activation.

To address if GLK may directly phosphorylate and activate PKC-θ during T cell signaling, we investigated whether GLK interacted with PKC-θ during TCR signaling using co-immunoprecipitation assays. CD3 stimulation induced interaction between the endogenous GLK and PKC-θ in primary T cells and GLK-PKC-θ interaction was concomitant with PKC-θ activation (FIG. 1b). Similar results were also observed using HEK293T, Jurkat and EL4 cell lines (FIG. 8a-c). The direct interaction between GLK and PKC-θ was further demonstrated in vitro, using binding assays of purified GLK and PKC-θ proteins (FIG. 1c). To determine the sites of PKC-θ phosphorylation by GLK, we examined PKC-θ phosphorylation at T53S, S676 and S695[4], which are the three major phosphorylation sites of PKC-θ. T538 phosphorylation is the most critical for PKC-θ kinase activation and subsequent NF-κB activation. In vitro kinase assays using immunoprecipitated Flag-GLK and Myc-PKC-θ showed that GLK phosphorylated PKC-θ at T538, but not at S676 or S695 (FIG. 1d).

In in vitro kinase assays using purified GLK and PKC-θ proteins, PKC-θ-T538 was directly phosphorylated by GLK (FIG. 1e). Taken together, our results indicate that GLK directly interacts with PKC-θ and phosphorylates PKC-θ at T538 during TCR signaling.

SLP-76 is a Direct Upstream Regulator of GLK

SLP-76 is a critical scaffold protein in T cells and is required for TCR-induced PKC-θ-IKK activation[2]. We asked whether SLP-76 was a direct upstream regulator of GLK in TCR signaling. CD3 stimulation induced an interaction between endogenous GLK and SLP-76 in primary T cells (FIG. 2a). The SLP-76-GLK interaction preceded the GLK-PKC-θ interaction and PKC-θ activation. Similar results were also observed using Jurkat and HEK293T cells (FIG. 9a-c). Moreover, the interaction between SLP-76 and GLK was mediated through tyrosine phosphorylation (FIG. 9d). In vitro binding assays using purified GLK and SLP-76 demonstrated a direct interaction between these two proteins (FIG. 2b). Next, we studied whether SLP-76 was required for GLK activation. The GLK kinase activity induced by CD3 stimulation was abolished in SLP-76-deficient J14 cells (FIG. 2c) and SLP-76 shRNA-transfected Jurkat cells (FIG. 2d). A previous report demonstrates that Vav1 is associated with SLP-76 and is involved in PKC-θ translocation, suggesting that Vav1 controls PKC-θ activation. Thus, we studied whether Vav1 regulated GLK activation. However, TCR-induced GLK kinase activation was not affected by Vav1 shRNA knockdown (FIG. 9). These data ruled out the involvement of Vav1 in the regulation of GLK kinase activation in TCR signaling. As another MAP4K, namely HPK1, is also activated by SLP-76 and in turn negatively regulates SLP-76 activation by inducing SLP-76-S376 phosphorylation, we asked whether GLK was involved in the negative feedback regulation of SLP-76. SLP-76-S376 phosphorylation was induced only by HPK1, but not by GLK (FIG. 2e), suggesting GLK does not feedback to negatively regulate SLP-76. These findings indicate that SLP-76 directly interacts with and activates GLK during TCR signaling.

GLK Controls T Cell-Mediated Immune Responses In Vivo

To study the role of GLK in vivo, we generated GLK-deficient mice (FIG. 11a,b). T cell development was normal in GLK-deficient mice (FIG. 11c-e). The effect of GLK deficiency on TCR signaling was studied in primary T cells. Consistent with our previous observations (FIG. 1), the phosphorylation of PKC-θ and IKK was abolished in GLK-deficient T cells upon CD3 (FIG. 3a) or CD3-CD28 co-stimulation (FIG. 3b). In contrast, Erk and PDK1 activation was unaffected by GLK deficiency (FIG. 3b). The phosphorylation of Lck, LAT and PLCγ1, as well as $Ca^{2+}$ signaling were also unaffected (FIG. 11f and FIG. 8c). As NF-κB signaling regulates T cell proliferation, we also studied the effect of GLK on T cell proliferation using [$^3$H]thymidine incorporation and CFSE dye dilution assays. GLK deficiency significantly blocked T cell proliferation induced by CD3 stimulation, but not by PMA plus ionomycin stimulation (FIG. 3d,e; FIG. 11g). Because PMA and ionomycin bypass proximal TCR signaling, this result suggests that GLK activity is induced by TCR proximal signaling complex. Furthermore, the reduced cell proliferation of GLK-deficient T cells was rescued by ectopically expressed GLK (FIG. 3c). These data demonstrate that GLK is important for T cell proliferation.

We next investigated whether GLK played an important role in T cell-mediated immune responses in vivo. We immunized wild-type and GLK-deficient mice with keyhole limpet hemocyanin (KLH), a T cell-dependent antigen, using alum as an adjuvant. T cells from KLH-immunized GLK-deficient mice showed hypo-proliferation after KLH restimulation (FIG. 4a). Moreover, the levels of cytokines, including interferon-γ (IFN-γ), interleukin 2 (IL-2) and IL-4 were also significantly decreased in KLH-restimulated splenic T cells from GLK-deficient mice (FIG. 4b). suggesting impaired in vivo T cell activation. Production of antigen-specific antibodies in the sera after primary and secondary immunization was also greatly reduced in GLK-deficient mice (FIG. 4c,d). These results indicate that GLK is required for mounting immune responses and antibody productions.

GLK-Deficient Mice are Resistant to Autoimmunity

The experimental autoimmune encephalomyelitis (EAE) is mainly mediated by IL-17-producing CD4+ T lymphocytes ($T_H17$)[11]. PKC-θ deficiency results in ameliorated EAE and $T_H17$ responses. Because GLK activated PKC-θ. we studied the roles of GLK in $T_H17$-mediated autoimmune diseases by using the experimental autoimmune encephalomyelitis model. GLK-deficient mice barely showed any symptom, while their wild-type littermates developed severe experimental autoimmune encephalomyelitis (FIG. 4e). The percentage of $T_H17$ cells in the infiltrating lymphocytes in the brains and spinal cords of immunized mice at day 14 was significantly lower in GLK-deficient mice (FIG. 4f). In addition, the titer of IL-17 in sera was also significantly lower in GLK-deficient mice (FIG. 4g). To investigate whether the defective $T_H17$ response in GLK-deficient mice is a T cell intrinsic effect, we determined the in vitro $T_H17$ differentiation potential of GLK-deficient naive T cells. Consistently, in vitro differentiation of $T_H17$ cells, as well as $T_H1$ and $T_H2$ cells, was reduced by GLK deficiency (FIG. 4h and FIG. 12). In vitro $T_{reg}$ differentiation was not affected by GLK deficiency (FIG. 12); however, GLK-deficient $T_{reg}$ cells displayed higher suppressive activity in vitro (FIG. 4i). These results indicate that GLK deficiency in vivo protects mice from the development of $T_H17$-mediated autoimmune diseases. Defective TCR signaling and $T_H17$ differentiation, as well as enhanced $T_{reg}$ function in GLK-deficient T cells may play critical roles in the resistance of GLK-deficient mice.

GLK-Induced PKC-θ Activation in Human SLE $T_H17$-mediated inflammation also plays an important role in the human autoimmune disease systemic lupus erythematosus (SLE). Since autoimmune induction and $T_H17$ responses were attenuated in GLK-deficient mice and GLK activates the PKC-θ-IKK pathway, we studied whether the GLK-PKC-θ-IKK-IL-17 cascade was involved in human SLE. We examined GLK expression and PKC-θ-IKK activation in peripheral blood leukocytes (PBLs) isolated from 49 SLE patients and 35 paired healthy controls (FIG. 13a). Flow cytometry analyses showed that the percentage of GLK-expressing T cells, but not B cells, from freshly isolated PBLs of SLE patients was significantly increased (FIG. 5a). The percentage of GLK-expressing T cells correlated with SLE disease activity index (SLEDAI) (FIG. 5b; Pearson correlation coefficient: r=0.773). Notably, one third (16/49) of SLE patients with high percentages (≥21%) of GLK. expression (GLK+) T cells showed higher correlation (r=0.807; FIG. 5c, Table 1), compared to patients with GLK in the normal range (r=0.451: Table 1). The amount of GLK protein expression was also increased in SLE patients (FIG. 5d). These results suggest that GLK overexpression is involved in SLE pathogenesis for 30% of patients. Table 1 shows Comparison of the correlation between SLEDAI and the percentages of GLK+ T cells from different SLE patient subsets.

TABLE 1

| Subsets of people with SLE and GLK+ T cells | SLEDAI (mean) | Pearson correlation coefficient (r) |
| --- | --- | --- |
| Total | 9.6 | 0.773 |
| ≥21% | 16.4 | 0.807 |
| <21% | 6.9 | 0.451 |

For people with SLE and low GLK+ T cells (<21%), the adjusted regression correlation coefficient is $r^2 = 0.177$, P value = 0.008503.

We next investigated whether GLK overexpression in the T cells from SLE patients induced PKC-θ-IKK activation. The percentage of phospho-PKC-θ or phospho-IKK positive T cells was increased and co-stained with GLK expression in T cells from SLE patients (FIG. 5e). Similarly, immunoblot analyses showed an induction of PKC-θ-IKK activation in SLE patients (FIG. 5d). These data suggest that GLK activates PKC-θ in T cells from SLE patients. The titer of IL-17, but not TNF or IL-6, was enhanced in the sera of SLE patients (FIG. 8b). These results suggest that GLK overexpression in T cells drives autoimmune pathogenesis in lupus patients. Thus, GLK is an important positive regulator of autoimmune diseases by directly activating PKC-θ in T cells.

Discussion

A key finding of our study is the identification of GLK as a kinase that directly phosphorylates PKC-θ at T538 during TCR signaling. PKC-θ phosphorylation at residue T538 within the activation loop is essential to NF-κB activation in T cells[4]. GLK-induced PKC-θ-IKK phosphorylation was independent of PDK1 activation and of CD28 co-stimulation, suggesting that GLK functions independent of PDK1 activation. These data clearly indicate that GLK is the direct upstream kinase for PKC-θ in TCR signaling.

Results from in vitro T cell differentiation assays further indicate that GLK plays an intrinsic and positive role in T helper cell differentiation. The mechanism by which GLK regulates T helper cell differentiation is still unknown. However, in vitro differentiation of $T_H1$, $T_H2$, and $T_H17$ was all reduced by GLK deficiency, suggesting that GLK may regulate T helper cell differentiation through a common mechanism (e.g., enhancing TCR signaling or IL-2 production) instead of regulating different cytokine signaling pathways for different T helper differentiation pathways.

Our studies of the in vivo roles of GLK demonstrate that GLK is required for optimal T cell immune responses and antibody production. The decrease in T cell-secreted cytokines, such as IL-2, IFN-γ (a $T_H1$ cytokine), and IL-4 (a $T_H2$ cytokine) as well as the reduction in the production of antigen-specific antibodies after primary and secondary immunization in GLK-deficient mice are similar to deficiencies reported in PKC-θ-deficient T cells. The resistance of GLK-deficient mice to EAE induction and decreased $T_H17$ responses are also consistent with the phenotypes of PKC-θ-deficient mice. The number of thymic natural $T_{reg}$ was unaffected in GLK-deficient mice. However, $T_{reg}$ numbers are impaired in PKC-θ-deficient, CARMA1-deficient, BCL10-deficient, or IKK2-mutant mice due 10 impaired PKC-θ-NF-κB signaling. PKC-θ can be activated by multiple signaling pathways, such as CD28, CD4, CD5, LFA-1 stimulation or ER stress signaling. It remains unclear how PKC-θ-NF-κB signaling is activated during $T_{reg}$ development. Our data indicate that GLK activates PKC-θ by phosphorylating the T538 residue, but not other known phosphorylation sites (such as S676 and S695). GLK is probably not the only PKC-θ activating kinase. Thus, it is likely that PKC-θ-CARMA1-BCL10-IKK2 can still be activated by other kinases in $T_{regs}$, leading to normal numbers of $T_{reg}$ in GLK-deficient mice. Although $T_{reg}$ numbers were unaffected in GLK-deficient mice, $T_{reg}$ activity was enhanced by GLK deficiency. PKC-θ plays a negative role in $T_{reg}$-mediated suppression. Taken together, the roles of GLK in regulating $T_H1$, $T_H2$, $T_H17$ and $T_{reg}$ cells were essentially consistent with those of PKC-θ, supporting the idea that GLK is probably the sole activator of PKC-θ in TCR signaling.

In this study we also report that GLK expression was induced in peripheral blood T cells of SLE patients and positively correlated with disease severity. T cells with GLK overexpression isolated from SLE patients also displayed increased PKC-θ-IKK activation suggesting that the activation of the GLK-PKC-θ-IKK pathway controls SLE pathogenesis. This is the first demonstration of GLK overexpression and PKC-θ-IKK hyperactivation in T cells of SLE patients. The elevation of serum IL-17 in SLE patients is consistent with previous reports. In comparison to the correlation between serum IL-17 and SLEDAI (Pearson correlation coefficient: r=0.41), the correlation between GLK and SLEDAI (r=0.773) is much higher and significant. Taken together, our findings indicate that GLK plays an important role in autoimmune pathogenesis and could serve as a novel diagnostic biomarker for the progression of SLE; in addition, the inhibition of GLK and its downstream PKC-θ-IKK signaling may offer novel therapeutic strategies for SLE.

II. GLK Overexpression in T Cells as a Novel Biomarker of Rheumatoid Arthritis

Our previous study demonstrated that GLK controls autoimmunity through activation of the protein kinase C-θ (θ)—inhibitor of NF-κB kinase (IKK)—NF-κB signaling pathway in T cells (Chuang el al. (2011) "The kinase GLK controls autoimmunity and NF-κB signaling by activating the kinase PKC-θ in T cells". Nat Immunol. 12(11): 1113-1118, which is incorporated herein by reference). T cells from systemic lupus erythematosus (SLE) patients display GLK overexpression, which is highly correlated with disease severity; however, the role of GLK in RA remained unknown.

Collagen-induced arthritis (CIA) is an extensively studied animal model that develops a destructive inflammatory synovitis resembling RA. PKC-θ deficient mice display attenuated response to CIA [14]. IKK-β inhibition is an effective treatment for bone and cartilage destruction in an arthritis animal model. Because PKC-θ and IKK play critical roles in inflammatory arthritis, we investigated the potential role of the upstream kinase GLK in the pathogenesis of RA using collagen-immunized mice and clinical samples from human RA patients.

Materials and Methods

Participants. Thirty patients fulfilling the 1987 revised criteria of the American College of Rheumatology for RA were enrolled. Twenty-four healthy volunteers served as healthy controls. Synovial tissues and fluids from eight osteoarthritis (OA) and eight RA patients were obtained. This study protocol was approved by the Ethics Committee of Clinical Research, Taichung Veterans General Hospital.

Disease activity. Serum levels of erythrocyte sedimentation rate (ESR), C-reactive protein (CRP), and 28-joint disease activity score (DAS28) were used to assess RA disease activity.

GLK-deficient mice. A 129 mouse embryonic stem cell clone with GLK deficiency (RRO270) from the European Conditional Mouse Mutagenesis Project was injected into blastocysts from the mouse line C57BL/6 to generate chimeric mice at the Transgenic Mouse Model Core, National Research Program for Genomic Medicine of Taiwan. GLK-deficient mice were backcrossed to C57BL/6 background for nine generations. All animal experiments were performed to protocols approved by the Institutional Animal Care and Use Committee at the National Health Research Institutes, Taiwan.

Induction and scoring of arthritis. Collagen-induced arthritis (CIA) was induced in wide type (WT) or GLK-deficient mice as previously described (Campbell et al (2000) "Collagen-induced arthritis in C57BL/6 (H-2b) mice: new insights into an important disease model of rheumatoid arthritis" Eur J Immunol. 30(6): 1568-1575). At 12 weeks of age (day 0), mice were intradermally injected into the base of the tail with a total of 100 μl of an emulsion containing the chicken type II chicken collagen/Freund's complete adjuvant emulsification (MD Biosciences, Zurich, Switzerland). The same injection was repeated intraperitoneally on day 21. Then, clinical signs of disease in WT or GLK-deficient mice using following clinical scores, where 1=swollen digit(s), 2=erythema, 3=swollen paw/ankle, and 4=loss of function.

Determination of serum cytokines. Serum levels of TNF-α, IL-1β, IL-6 and IL-17A in WT or GLK-deficient mice and RA patients were determined using ELISA according to the manufacturer's instructions (eBiosciences, San Diego, Calif., USA).

Reagents A antibodies. Antibodies for GLK were generated by immunizing rabbits with individual peptides. Anti-p-PKC-θ (T538) antibody (Upstate Biotechnology, Lake Placid, N.Y., USA) was used for western blotting. Anti-PKC-θ antibody (Santa Cruz Biotechnology, Santa Cruz, Calif., USA) was used for intracellular staining. Anti-hCD3-PECy7 (SK7; BD Pharmingen, San Diego, Calif., USA), anti-p-PKCθ T538 (19/PKC; BD Pharmingen, San Diego, Calif. USA), and anti-p-IKK (2681S) (Santa Cruz. Biotechnology, Santa Cruz, Calif., USA) antibodies were used for flow cytometry analyses. TaqMan probes and primer sets (Applied Biosystems, Foster City, Calif., USA) were used for GLK mRNA detection.

Western blotting analyses & Flow cytometry analyses. For immunoblotting analyses, samples of synovial leukocytes and purified peripheral blood T cells were performed as described previously (Chuang et al. (2011) "The kinase GLK controls autoimmunity and NF-κB signaling by activating the kinase PKC-θ in T cells". Nat Immunol. 12(11): 1113-1118, which is incorporated herein by reference). Flow cytometry analyses of peripheral blood and synovial fluids were also performed as described previously.

Immunohistochemistry. Immunostaining of GLK on synovial membranes was performed in RA and OA patients. Paraffin-embedded tissues were boiled for 10 min and washed with water for 2 min. Sections were then pre-incubated with hydrogen peroxidase block (Thermo Scientific, Wallham. Mass., USA) for 1 h and incubated with anti-CD3 antibody (Santa Cruz Biotechnology, Santa Cruz, Calif., USA) plus anti-GLK antibody at 4° C. overnight. Colors were produced with LVBlue/LVRed (MultiVision Polymer Detection System, Thermo Scientific, Waltham, Mass., USA).

Statistical Analysis. Statistical Package for the Social Sciences (SPSS) version 13.0 software (SPSS Inc., Chicago, Ill., USA) was used for statistical analyses. Student's t-test was used for comparisons between continuous variables. Pearson's correlation was used to determine the correlation between variables. Simple linear regression was used to study the correlation between the frequencies of GLK-expressing T cells and DAS28 in RA patients.

Results

Impaired Development of Collagen-Induced Arthritis in GLK-Deficient Mice

We previously demonstrated that T cell-mediated immune responses are impaired in GLK-deficient mice (Chuang et al. Nat Immunol. 2011; 12(11): 1113-1118, which is incorporated herein by reference). To investigate the contribution of GLK to inflammatory arthritis, we studied the induction of autoimmune responses in wild-type (WT) and GLK-deficient mice using the CIA model. WT mice developed severe CIA. whereas GLK-deficient mice showed drastically reduced symptoms (FIG. 14A, B). The inflammatory cytokines are induced during CIA development. We found that serum levels of IL-1β, IL-6, and IL-17A were significantly decreased in collagen-immunized GLK-deficient mice as compared with WT mice (FIG. 15 C-E). These results suggest that GLK is required for inflammatory arthritis.

Demographic Data and Clinical Features of HA Patients

To study whether GLK levels was increased in T cells from RA patients, thirty RA patients (66.7% female, mean age: 50.3±15.7 years) and 24 healthy controls (62.5% female, mean age: 33.4±8.3) were enrolled (Table 2). Table 2 shows Demographic data, clinical manifestations, and laboratory findings of rheumatoid arthritis (RA) patients and healthy controls (HC)[#].

TABLE 2

|  | RA (n = 30) | HC (n = 24) |
| --- | --- | --- |
| Age at study entry (years) | 50.3 ± 15.7* | 33.4 ± 8.3 |
| Gender (female, %) | 20 (66.7) | 15 (62.5) |
| Disease duration (years) | 6.7 ± 9.8 | NA |
| RF (IU/ml) | 64.8 ± 63.1 | NA |
| Anti-CCP antibody (unit) | 133.4 ± 86.5 | NA |
| DAS28 | 4.8 ± 1.0 | NA |
| ESR (mm/hour) | 35.9 ± 24.4** | 14.0 ± 2.3 |
| CRP (mg/dl) | 1.00 ± 1.72* | 0.09 ± 0.02 |
| Daily prednisolone dose (mg) | 5.9 ± 2.8 | NA |
| Methotrexate (%) | 23 (76.6) | NA |
| Hydroxychloroquine (%) | 11 (36.6) | NA |
| Sulfasalazine (%) | 4 (13.3) | NA |
| Anti-TNF-α therapy (%) | 19 (63.3) | NA |

[#]Values are mean ± standard deviation or the number (%) of patients.
*p < 0.05:
** p < 0.001, HC versus RA patients, determined by Student's t-test.
RF: rheumatoid factor;
CCP: cyclic citrullinated peptide:
DAS28: disease activity score for 28-joints:
ESR: erythrocyte sedimentation rate;
CRP: C-reactive protein;
TNF-α: tumor necrosis factor-α;
NA: not applicable.

Increased (ILK Expression in Purified Peripheral Blood T Cells from RA Patients

Protein levels of GLK were increased in purified peripheral blood T cells from RA patients determined by Western blotting (FIG. 15A). GLK expression levels in purified T cells from RA patients were significantly higher than that in healthy controls (1.3±0.8 vs. 0.4±0.4, p=0.047, FIG. 15B). Moreover, GLK mRNA levels in purified peripheral blood T cells were also significantly higher in RA patients compared with healthy controls (12.3±18.5 vs. 1.0±1.2, p=0.029, FIG. 15C). Because GLK activates PKC-θ, we studied whether GLK-induced PKC-θ activation was involved in RA. PKC-θ activation was also enhanced in peripheral T cells from RA patients (FIG. 15A).

Increase of GLK Expression in T Cells From RA Synovial Fluids and Synovial Tissues We next studied whether GLK was also expressed in the T cells from synovial microenvironment of human RA patients. GLK expression and PKC-θ activation were enhanced in synovial fluid leukocytes from RA patients by Western blotting (FIG. 16A). The frequency of GLK-expressing CD3$^+$ T cells in synovial fluids from RA patients was much higher than that in OA patients by flow cytometry analyses (FIG. 16B). Immunohistochemistry staining for anti-GLK (blue) and anti-CD3 (brown) in synovial tissues of RA and OA patients were performed. As illustrated in FIG. 16C, GLK-expressing T cells were increased in synovial tissues from RA patients but could barely be detected in those from OA patients.

Co-Localization of GLK, PKC-θ and CD3 in T Cells from Synovial Fluids and the Peripheral Blood Confocal microscopy showed that GLK co-localized with PKC-θ and CD3 in T cells from both synovial fluids (FIG. 17A) and peripheral blood (FIG. 17B) of RA patients, suggesting that GLK interacts with active PKC-θ on the T-cell membrane.

TABLE 3

|  | Pearson's correlation coefficient (r) | p value |
| --- | --- | --- |
| TJC | 0.500 | 0.005 |
| SJC | 0.132 | 0.488 |
| ESR | 0.400 | 0.003 |
| CRP | 0.330 | 0.015 |
| DAS28 | 0.606 | 0.0005 |

RA: rheumatoid arthritis;
GLK: GCK-like kinase;
TJC: tender joint counts;
SJC: swelling joint counts;
DAS28: disease activity score for 28-joints;
ESR: erythrocyte sedimentation rate;
CRP: C-reactive protein.

Correlation of GLK-Expressing T-Cell Frequencies with RA Disease Activity

Serum TNF-α (27.6±42.4 v.s. 5.4±13.9 pg/ml, p=0.019) and IL-17A (14.2±12.1 v.s. 7.5±4.4, pg/ml, p=0.15), but not TGF-β (6.5±5.14 v.s. 5.2±7.6 pg/ml, p=0.5) levels were higher in RA patients than those in healthy controls (FIG. 18A-C). Flow cytometry analyses showed that the frequencies of GLK-expressing, phospho-PKC-θ-positive, and phospho-IKK-positive peripheral blood T cells were greater from RA patients (FIG. 18D). The frequencies of GLK-expressing peripheral blood T cells were significantly higher in RA patients than in healthy controls (18.4±7.6 vs. 10.5±5.0, p<0.001, FIG. 18E). Moreover, these GLK-expressing T cells also expressed phosphorylated PKC-θ and IKK in RA patients. These data suggests that the GLK-PKC-θ-IKK cascade is involved in the pathogenesis of human RA. The frequencies of GLK-expressing T cells were correlated with lender joint counts (r=0.500, p=0.005, FIG. 19A). erythrocyte sedimentation rate (ESR; r=0.400, p=0.003, FIG. 19B), C-reactive protein (CRP; r=0.330, p=0.015, FIG. 19C), or 28-joint disease activity score (DAS28; r=0.606, p=0.0005, FIG. 19D) in RA patients (Table 3). After removing 4 outliers that showed high residual (modulus>1) in simple linear regression, the remaining eighty-six percent (26 of 30) of RA patients showed even higher correlation between the frequencies or GLK-expressing T cells and DAS28 (r=0.712, p=0.0000639, FIG. 19E). These results suggest that GLK signaling plays important roles in the pathogenesis of RA.

Table 3 shows Pearson's correlation between RA disease activity and GLK-expressing T-cell frequencies in enrolled subjects.

In this study, we found that GLK was overexpressed in T cells of peripheral blood and synovial tissues from RA patients. GLK deficiency attenuated the development of CIA in mice. Moreover, the frequencies of GLK-expressing T cells were significantly correlated with RA disease severity, indicating that GLK contributes to the pathogenesis of RA. Our results suggest that GLK is a novel diagnostic biomarker and is a potential target for therapeutic regimens.

Over the past years, p38MAPK has been considered crucial to the induction and maintenance of Th1/Th17-mediated chronic inflammation in RA; but inhibition of p38MAPK does not provide significant benefits in early-phase trials. GLK is a serine/threonine kinase that is widely expressed in different human tissues and is an upstream kinase of MAPK signaling. Our recent study demonstrates that GLK induces the IKK-NF-κB pathway by directly phosphorylating and activating PKC-θ. Our studies and previous reports using EAE and CIA models showed that both GLK-deficient and PKC-θ-deficient mice display lower Th1/Th17-mediated autoimmune responses, suggesting that GLK signaling controls autoimmunity. GLK co-localized with PKC-θ in T cells from peripheral blood and synovial fluids of RA patients. Furthermore, most of the GLK-expressing T cells were PKC-θ/IKK activated cells. To our knowledge, the present study is the first report that GLK overexpression and PKC-θ/IKK hyperactivation in T cells are novel biomarkers for RA patients. Moreover, the frequency of GLK-positive T cells was positively correlated with RA disease activity, indicating that the GLK-PKC-θ-IKK pathway plays a crucial role in the pathogenesis of RA.

Up-regulation of the NF-κB pathway is critical for synthesis of matrix-degrading enzymes, leading to bone erosion in RA, while inhibition of IKK protects against bone and cartilage destruction. Anti-CD3-induced NF-κB activation is also enhanced by GLK overexpression and suppressed by GLK siRNA in T cell lines, suggesting that inhibition of GLK may alleviate inflammation in RA. Compromised regulatory T cells (Treg) function has been reported in RA patients, while inhibition of PKC-θ restores defective Treg activity from RA patients. GLK-deficient mice show that Treg-mediated suppressing function is enhanced. Thus, the GLK-PKC-θ pathway negatively regulates Treg function. Taken together, antagonizing GLK in RA patients might diminish T cell-mediated immune responses and boost Treg-mediated suppressing functions, suggesting that GLK is a promising therapeutic target for RA.

This study has some limitations. First, its design is cross-sectional, making it difficult to assess the influence of pharmacologic treatment on GLK expression. Previous reports have shown that glucocorticoids inhibit PKC-θ signaling and that TNF-α inhibitors reduce NF-κB-regulated gene expression. Although immunosuppressive agents may reduce the expression of GLK, PKC-θ, IKK, or NF-κB in T cells of RA patients, GLK levels were still significantly higher and correlated with disease activity in at least 86% of RA patients. Second, the role of GLK in the pathogenesis of bone destruction and cartilage damage is still elusive. Nevertheless, our results demonstrate a link between GLK and joint inflammation in RA patients.

Our results indicate that GLK plays a critical role in the pathogenesis of RA and is a potential diagnostic biomarker for disease severity. In addition, the inhibition of GLK and its downstream PKC-θ-IKK signaling may offer novel therapeutic strategies for RA.

III. Germinal Center Kinase (GCK)-Like Kinase (GLK/MAP4K3) Expression is Increased in Adult-Onset Still's Disease and May Act as an Activity Marker The enhanced expression of GLK has been shown to correspond with disease severity in patients with systemic lupus erythematosus (SLE). We investigated the role of GLK in the pathogenesis of adult-onset Still's disease (AOSD), which shares some similar clinical characteristics with SLE.

Methods

Subjects. Twenty-four consecutive patients with active untreated AOSD (15 females and 9 males, mean age±SD, 33.3±9.9 years) fulfilling the Yamaguchi criteria were enrolled. Patients with infections, malignancies or other rheumatic diseases were excluded. The disease activity scores (range, 0-12) for each AOSD patient were assessed according to the criteria described by Pouchot et al. After an initial determination of the levels of circulating GLK-expressing T-cells and Th17-related cytokines, all AOSD patients received corticosteroids and non-steroidal anti-inflammatory drugs (NSAIDs). The disease-modifying anti-rheumatic drugs (DMARDs) used were methotrexate (20 patients), hydroxychloroquine (18 patients), sulfasalazine (8 patients), and azathioprine (3 patients). Twelve age-matched healthy volunteers (8 females and 4 males, mean age 32.4±8.2 years), who had no rheumatic disease, served as normal controls. Peripheral blood was collected using endotoxin-free heparinized vacuum lubes (KABI-ET; Chromogenix, Antwerp, Belgium) to avoid cytokine production during the interval between sampling and culture. The Ethics Committee of Clinical Research, Taichung Veterans General Hospital, approved this study (No. C10130) and written consent was obtained from all participants according to the Declaration of Helsinki.

Quantitation of circulating GLK-expressing T-cells using flow cytometry analysis. Circulating GLK-expressing T-cells were quantified using flow cytometry analysis according to the technique described in a recent study. Antibodies for GLK were generated by immunizing rabbits with individual peptides. Briefly, peripheral blood mononuclear cells (PBMCs) were harvested, washed with cold PBS. and stained with indicated antibodies for 30 min on ice. PBMCs were then treated with Golgi-stop (10 μg/ml of Brefeldin A, Sigma, Germany) without any other stimulation and then stained with anti-CD3-allophycocyanin [APC]-Cy7 (BD Pharmingen), anti-CD4-pacidic blue (BD Pharmingen), and anti-CD8-peridinin chlorophyll protein (PerCP) cyanin 5.5 (Cy5.5) (BD Pharmingen), at the room temperature. For intracellular staining, PBMCs were permeabilized in 200 μl Cytofix/Cytoperm buffer (BD Biosciences) for 2 h and washed with Perm-Wash buffer. The pellet was incubated with 100 μl Reagent 2, saponin (Beckman Coulter, USA) for 5 minutes at RT in the dark. Samples were washed twice with 0.1% BSA-PBS, and incubated with PE-conjugated GLK-specific mAb (eBiosciences, USA) for 30 minutes at RT in the dark. An isotype control IgGI-PE (eBiosciences, USA) was used for GLK staining at RT in the dark. After staining, the cells were washed and immediately analyzed using flow cytometry (Beckman Coulter, USA). Lymphocytes were gated on the basis of forward and size scatter properties, and at least 10,000 $CD3^+$ cells were analyzed. Data were collected using FACSCanto II flowcytometer (BD Biosciences) and analyzed by FlowJo software.

Western blotting for GLK expression. For immunoblotting analysis, samples of purified T cell were performed as described in our recent study. For GLK, the reaction mixtures an equal amount of cell extracts from each set of experiments Were fractionated on 6-8% SDS-PAGE in running buffer (25 mM Tris, 192 mM glycine, 0.1% SDS). The gel was run at 90V 30 minutes then at 130V until the blue dye front reached the bottom. The gel was transferred to polyvinylidene difluoride membrane (PVDF) in transfer buffer (50 mM Tris, 384 mM glycine, 20% methanol) at 21V 1 hr with the Trans-Blot SD Semi-Dry Electrophoretic Transfer Cell (BIO-RAD, USA). The membranes were blocked with 5% BSA in TBST (150 mM NaCl, 20 mM Tris-HCl (pH 7.4), 0.1% Tween-20) at room temperature for 1 hr then probed with Anti-GLK (1:1000), which was generated by immunizing rabbits with the appropriate peptide and anti-p-tubulin (1:1000 T4026, Sigma, USA) at 4° C. overnight. The membranes were washed about 3 times with TBST, followed by incubation with peroxidase-conjugated secondary antibody (1:6000) at room temperature for 1 hr. The membranes of antibody reaction were washed 3 times with TBST and performed using the enhanced Immobilon Western Chemiluminescent HRP Substrate (WBKLS0500, Millipore, USA) that exposed with new MegaCam 810 scientific grade CCD camera (UVP, LLC. Calif., USA). The relative expression level of GLK protein was normalized to β-tubulin, and values were expressed relative to control.

Quantitative PCR (qPCR) for GLK expression. PBMCs were immediately isolated from venous blood using Ficoll-Paque™ PLUS (GE Healthcare Biosciences, Sweden) density gradient centrifugation. Total cellular RNA was obtained from PBMCs by the guanidinium isothiocyanate method and was quantified by spectrophotometry at 260 nm. A 2.5 µg RNA aliquot was reverse transcribed with 200 U of Moloney murine leukemia virus reverse transcriptase (Fermentas, Thermo Fisher Scientific Inc., USA) according to standard procedures. GLK mRNA expression levels were determined by qPCR assay supplied in a TaqMan PCR Core Reagent Kit (Applied Biosystems, USA). Primers specific for GLK and the internal control glyceraldehydes-3-phosphate dehydrogenase (GAPDH) were obtained from Applied Biosystems (Foster City, Calif., USA). The purity of PCR products was assessed by dissociation curve plots. To standardize mRNA levels of GLK, transcript levels of the housekeeping gene GAPDH were also determined in parallel for each sample. The relative expression level of GLK was calculated with comparative threshold cycle (Ct) method and evaluated by $2^{-\Delta\Delta Ct}$, $\Delta\Delta Ct$=Patent $(Ct_{GLK\ gene}-Ct_{GAPDH})$–Mean of controls $(Ct_{GLK\ gene}-Ct_{GAPDH})$.

Determination of serum levels of soluble IL-2 receptor (sIL-2R) and Th17-related cytokines. Serum sIL-2R levels were determined using an ELISA kit (Cellfree; Endogen Inc, Mass. USA). Serum levels of IL-1β, IL-6, IL-17A, and TNF-α were determined in AOSD patients and healthy controls using enzyme-linked immunosorbent assay according to the manufacturer's instructions (eBiosciences, San Diego, Calif., USA).

Statistical analysis. Results are presented as the mean±SD or median (interquartile range). The nonparametric Kruskal-Wallis test was used for between-group comparison of the frequencies of circulating GLK-expressing T-cells, the expression levels of GLK transcript and protein, and serum levels of Th17-related cytokines. When this test showed significant differences, then the exact p values were determined using the Mann-Whitney U test. The correlation coefficient was calculated using the nonparametric Spearman's rank correlation test. Wilcoxon signed rank test was employed to compare the levels of circulating GLK-expressing T-cells and the expression levels of GLK during follow-up in AOSD patients after effective therapy. For comparison of, Wilcoxon signed rank test was employed. A probability of less than 0.05 was considered significant.

Results

Clinical Characteristics of AOSD Patients

As illustrated in Table 4, all 24 patients with active untreated AOSD had daily spiking fevers (≥39° C.). Other common manifestations included evanescent rash (20, 83.3%), sore throat (17, 70.8%) and arthritis (15, 62.5%). Lymphadenopathy and hepatosplenomegaly were noted in 10 (41.7%) and 6 (25.0%) patients respectively. There were no significant differences in age at entry of this study or the proportion of females between the AOSD patients and healthy controls. Table 4 shows demographic data and clinical characteristics of patients with adult-onset Still's disease (AOSD) and healthy controls (HC)[#].

TABLE 4

| Characteristics | AOSD (n = 24) | HC (n = 12) |
| --- | --- | --- |
| Age at study entry (years) | 33.3 ± 9.9 | 32.4 ± 8.2 |
| Proportion of females | 15 (62.5%) | 8 (66.7%) |
| Fever (≥38° C.) | 24 (100%) | NA |
| Evanescent rash | 20 (83.3%) | NA |
| Sore throat | 17 (70.8%) | NA |
| Arthritis | 15 (62.5%) | NA |
| Lymphadenopathy | 10 (41.7%) | NA |
| Liver dysfunction | 10 (41.7%) | NA |
| Hepatosplenomegaly | 6 (25.0%) | NA |
| Clinical activity score | 5.83 ± 1.34 | NA |
| CRP levels (U/L) | 3.3 ± 0.4 | NA |
| Ferritin levels (µg/L) | 692.9 ± 103.6 | NA |
| sIL-2R levels (pg/ml) | 563.5 ± 87.5 | NA |

[#]Data are presented as mean ± SD or number (percentage);
NA: not applicable.
Liver dysfunction was defined as alanine aminotransferase (ALT) level ≥ 40 IU/L:
CRP: C-reactive protein;
sIL-2R: soluble interleukin-2 receptor.

Increased Frequencies of Circulating GLK-Expressing T-Cells in AOSD Patients

Representative examples of flow cytometry contour plots of GLK expression in peripheral blood CD3[+] T cells, CD4[+] T cells, and CD8[+] T cells of one patient with active AOSD and one healthy control are shown in FIG. 20A-B, respectively. Significantly higher median frequencies of circulating GLK-expressing CD3 T cells were observed in patients with active AOSD (median=31.85%. interquartile [IQ] range 21.21%-48.84%) than in healthy controls (median=8.93%, IQ range 6.81%-12.08%; p<0.001, FIG. 20C).

Increased Expression of GLK Transcripts and Proteins in AOSD Patients

As shown in FIG. 20D, significantly greater fold increases in relative expression of GLK transcripts were observed in patients with active AOSD (median=2.35, IQ range 1.66-3.88) than in healthy controls (median=0.92, IQ range 0.63-1.37; p<0.001). Similarly, active AOSD patients had increased expression of GLK in the lysates of purified T cells determined by Western blotting (FIG. 20E). The relative expression levels of GLK proteins in active AOSD patients (median=1.74, IQ range 1.47-2.95) were significantly higher than those in controls (median=0.66, IQ range 0.54-0.94; p<0.001, FIG. 20F).

Increased Serum Levels of Th17-Related Cytokines in AOSD Patients

As shown in FIG. 21, active AOSD patients had significantly higher median levels of serum IL-6 (median=474.81, IQ range 156.42-987.55), IL-17A (median=306.80, IQ range 152.17-503.70), and TNF-α (median=51.85, IQ range 23.63-65.93) compared to those in healthy controls (median=85.78. IQ range 31.13-189.98, p<0.001 for IL-6; median=70.90, IQ range 51.42-124.53, p<0.001 for IL-17A; and median=24.66, IQ range 10.50-37.76, p<0.01 for TNF-α). However, mere was no significant difference in serum IL-1β levels between AOSD patients and HC.

Correlation Between GLK Expression and Disease Activity as Well as Cytokines in AOSD Patients

TABLE 5

|  | Circulating GLK-expressing T-cells (%) | Relative expression levels of GLK protein | Relative expression levels of GLK transcript |
|---|---|---|---|
| Clinical activity scores | 0.599** | 0.435* | 0.452* |
| CRP (mg/dL) | 0.455* | 0.315 | 0.364 |
| Ferritin (μg/L) | 0.508* | 0.296 | 0.318 |
| sIL-2R (pg/ml) | 0.865*** | 0.569** | 0.803*** |
| IL-1β (pg/ml) | 0.281 | 0.152 | −0.063 |
| IL-6 (pg/ml) | 0.822*** | 0.423* | 0.547** |
| IL-17A (pg/ml) | 0.787*** | 0.699*** | 0.740*** |
| TNF-α (pg/ml) | 0.295 | 0.177 | 0.310 |

AOSD: adult-onset Still's disease;
CRP: C-reactive protein;
sIL-2R: soluble interleukin-2 receptor;
IL-1β: interleukin-1β;
IL-6: interleukin-6;
IL-17A: interlukin-17A;
TNF-α: tumor necrosis factor-α.
*p < 0.05, p < 0.005, *p < 0.001 was obtained by the nonparametric Spearman's rank correlation test.

As illustrated in Table 5, the frequencies of circulating GLK-expressing CD3$^+$ T cells were positively correlated with disease activity including clinical activity scores, CRP levels, ferritin levels, and serum levels of sIL-2R which reflected T-cell activation in AOSD patients. Similarly, the relative expression levels of GLK proteins and transcripts were positively correlated with clinical activity scores and sIL-2R levels in AOSD patients. Among the Th17-related cytokines, GLK expression levels were positively correlated with serum levels of IL-6 and IL-17A. However, there was no significant correlation of GLK expression with clinical manifestations in our AOSD patients (data not shown). Table 5 shows the correlations between the frequencies of circulating GLK-expressing T cells, the relative expression levels of GLK protein as well as GLK transcript and disease activity parameters as well as Th17-related cytokines in 24 patients with AOSD.

Changes in the Levels of GLK Expression in AOSD Patients after Effective Therapy Twelve AOSD patients were available for examination both at the active phase and at the remission phase. As shown in FIG. 22, the levels of circulating GLK-expressing T cells, and the relative expression levels of GLK proteins as well as transcripts were significantly decreased (mean±SEM. 45.77±5.58 vs. 20.11±2.53; 3.01±0.49 vs. 0.93±0.17; and 3.45±0.56 vs. 1.21±0.38, respectively, all p<0.005), paralleling clinical remission and the decrease in serum levels of sIL-2R (747.8±131.8 pg/ml vs. 229.1±38.5 pg/ml, p<0.005) in AOSD patients after effective therapy.

This study is the first investigation to demonstrate GLK overexpression in active AOSD patients relative to healthy controls. The advent of flow cytometry analysis of intracellular signaling molecules has greatly expanded the opportunities to study single cell in heterogeneous cell populations. In the present study, CD3$^+$ T cells, including CD4 and CD5 subsets demonstrated increased GLK expression in patients with active AOSD. Our results also showed significantly elevated frequencies of circulating GLK-expressing T cells which correlated with disease activity, including clinical activity scores and serum ferritin levels, in AOSD patients. Moreover, a parallel decrease in GLK production with disease remission was found in the AOSD patients. These data concerning AOSD patients were similar to the results of our recent study showing elevated levels of circulating GLK-expressing T cells correlated with activity index in SLE patients, suggesting that GLK overexpression plays an important role in AOSD pathogenesis, and is thus a potential activity marker of this disease. However, a large prospective study should be conducted to confirm the findings presented herein.

To verify the GLK expression at the protein and transcript levels in AOSD patients, Western blotting and qPCR for GLK expression were performed in peripheral blood lymphocytes from our patients with active untreated AOSD. We have demonstrated that the relative expression levels of GLK proteins and transcripts were significantly higher in AOSD patients than in HC. Moreover, the positive correlations between the frequencies of circulating GLK-expressing T cells and the expression levels of GLK proteins in our study are consistent with the findings of previous studies showing that intracellular flow cytometry and Western blotting are equivalent assays for measuring MAPK signaling status. In addition, the expression levels of GLK proteins as well as transcripts were significantly correlated with clinical activity scores in our AOSD patients. These data provide the first direct and robust evidence of GLK overexpression in the T cells of AOSD patients.

Accumulating evidence indicates that Th17 cells play an important role in the pathogenesis of both AOSD and SLE. IL-6 synergizes with IL-1β to enhance the differentiation and generation of Th17 cells. Th17 cells can secrete IL-17, a pleiotropic cytokine which participates in tissue inflammation by inducing the expression of proinflammatory cytokines and chemokines. Our recent study showed that GLK-deficient mice are resistant to the development of EAE and showed decreased Th17 responses. The results from in vitro T cell differentiation assays also indicate that GLK plays a positive role in Th17 cell differentiation. In the present study, the results revealed elevated serum levels of Th17-related cytokines, IL-6 and IL-17A, which were correlated with the expression levels of GLK in T cells from AOSD patients. Our data also support previous findings showing that MAPK pathway plays an important role in the regulation of Th17-cell function, and that IL-17 production is mediated by MAPK-dependent mechanism. In addition, inhibition of MAPK could suppress IL-17 production in Vogt-Koyanagi-Harada syndrome, and attenuate Th17-mediated autoimmune disease, EAE. These observations suggest either GLK overexpression or MAPK signaling can participate in the production of Th17-related cytokines. However, there still exists the possibility that GLK upregulation may represent an epiphenomenon of inflammation rather than a primary event in the pathogenesis of AOSD.

Our longitudinal follow-up of AOSD patients showed significantly decrease in the levels of circulating GLK-expressing T-cells as well as the expression levels of GLK protein and transcript, paralleling the clinical remission and the decrease in inflammatory parameters after effective therapy (FIG. 23). Our results support the hypothesis that inhibitors of more upstream MAPK signaling pathways, such as MAP2K (MKK3 or MKK6) and MAP3K (transforming growth factor activated kinase 1, TAK1), can be a promising therapeutic modality for rheumatic diseases. As an upstream MAP kinase, GLK could also be targeted as a potential therapeutic strategy by broadly inhibiting downstream MAPKs or several p38 isoforms. Furthermore, upstream signaling molecules might be better targets than downstream molecules such as p38MAPK, blockade of which could result in considerable toxic effects.

Although some studies reported elevated IL-1β levels in AOSD and substantial benefit of IL-1β receptor antagonist (anakinra) for treatment of inflammatory diseases, our results showed no significant difference in IL-1β levels between AOSD patients and health volunteers.

Our results revealed that GLK overexpression with increasing levels of Th17-related cytokines may be involved in the pathogenic mechanisms of AOSD. Our data add to the evidence supporting the association between GLK overexpression and a list of inflammatory diseases. Our results also showed that GLK expression levels were positively correlated with disease activity of AOSD, indicating that GLK might be a novel activity biomarker and a potential therapeutic target.

IV. GLK as a Diagnostic Biomarker

Besides SLE patients, patient samples from seven additional autoimmune diseases also showed dramatically enhanced GLK expression in peripheral blood T cells (Table 6, FIGS. 24-26). GLK expression was correlated with the disease severity of RA and AOSD, as disclosed above. The GLK-overexpressing T cells were detected in synovial tissues from RA patients.

Our data showed that GLK-overexpressing peripheral blood T cells were all IL-17-producing cells in SLE patients (FIG. 27). To study the regulatory role of GLK in the pathogenesis of autoimmunity, we further generated T-cell-specific GLK transgenic (Tg) mice named Lck-GLK. Lck-GLK Tg mice spontaneously developed multiple autoimmune diseases with increase of serum IL-17 and SLE/rheumatoid arthritis autoantibodies (FIGS. 28 and 29). Lck-GLK Tg mice displayed phenotypes of rheumatoid arthritis and multiple sclerosis. IL-17 transcription in T cells was induced by transgenic GLK (FIG. 29). These results of LCK-GLK Tg mice suggest that the activation of the GLK-PKCθ-IKK-IL-17 axis contributes to autoimmune diseases.

Thus, GLK is a diagnostic biomarker and therapeutic target of multiple autoimmune diseases, including systemic lupus erythematosus, rheumatoid arthritis, adult onset Still's disease. Graves' disease, Sjogren's syndrome, neuromyelitis optlica, ankylosing spondylitis, and alopecia.

Since GLK induces NF-κB activation, which is involved in tumorigenesis, we studied the GLK expression in the carcinoma samples. Our recent data showed that GLK expression was significantly enhanced in human non-small-cell lung carcinoma (NSCLC), esophageal carcinoma, glioblastoma, pancreatic ductal adenocarcinoma, breast cancer, and hepatoma (FIGS. 30-35). IKK, but not mTOR, activation was enhanced in NSCLC (FIG. 30) These data suggest that GLK contributes to tumorigenesis through an mTOR-independent pathway. Furthermore, GLK overexpression in the tumor-part was highly correlated with early recurrence (i.e., distal metastasis) in NSCLC patients (P=0.009: FIG. 36). Our data showed that GLK overexpression induced tumorigenesis and tumor metastasis (FIG. 37). Thus, GLK is a novel biomarker and therapeutic target for multiple cancers such as lung cancer, esophageal cancer, glioblastoma, pancreatic cancer, breast cancer, and hepatoma.

Taken together, our data indicate that GLK is a novel biomarker and therapeutic target for autoimmune inflammatory diseases and cancers. Future development of GLK inhibitors could be used as therapeutics for the autoimmune inflammatory disease/cancer patients whose cells overexpress GLK.

Results

1. GLK is a Novel Biomarker of Multiple Autoimmune Diseases

Besides GLK overexpression in T cells of SLE, rheumatoid arthritis, and adult onset Still's disease patients, GLK overexpression was also found in T cells of Sjogren's syndrome, neuromyelitis optlica, ankylosing spondylitis, and alopecia (FIG. 24). We also found that GLK was overexpressed in T cells from drug-naive Grave's disease (GD) patients and patients who received partial anti-thyroid treatments but still in thyrotoxic status, determined by flow cytometry, immunoblotting, and quantitative polymerase chain reaction (qPCR) (FIGS. 25 and 26). GLK protein levels and mRNA levels were increased in T cell from GD patients (FIG. 25). Our results suggest that GLK overexpression contributes to pathogenesis and severity of autoimmune diseases and is a novel biomarker of autoimmune diseases. Table 6 shows GLK-mediated autoimmune diseases and cancers.

2. GLK Induces IL-17 Production in T Cells

To study the regulatory role of GLK in the pathogenesis of autoimmunity, we further generated T-cell-specific GLK transgenic (Tg) mice using the T-cell-specific promoter Lck. Lck-GLK Tg mice spontaneously developed multiple autoimmune diseases with a specific increase of serum autoantibodies and serum IL-17 (FIG. 27-29). These findings suggest that the activation of the GLK-PKCθ-IKK-IL-17 axis contributes to autoimmune diseases. The Lck-GLK Tg mice (8-week-old) expressing high level of GLK transgene showed a drastic induction of serum IL-17A levels. IL-17A mRNA levels were increased by transgenic GLK (FIG. 29). These results further confirm our data of SLE patients that GLK positively regulates IL-17A production in T cells.

TABLE 6

| Autoimmune Disease | Cancer |
| --- | --- |
| Rheumatoid arthritis (RA) | Esophageal carcinoma |
| Adult onset Still's disease (AOSD) | Glioblastoma |
| Graves' disease (GD) | Pancreatic ductal adenocarcinoma (PDA) |
| Sjogren's syndrome (SS) | Breast cancer |
| Ankylosing spondylitis (AS) | Hepatoma |
| Neuromyelitis optlica (NMO) | |
| Alopecia | |
| Autoimmune encephalomyelitis | |

3. GLK Overexpression in Multiple Types of Cancers.

GLK protein levels were increased (85.7%) in tumor part compared with normal part from lung-cancer patients. GLK protein levels were increased (58%) in tumor parts compared with normal parts from esophageal-cancer patients. GLK was also overexpressed in glioblastoma, pancreatic cancer, breast cancer, and hepatoma.

The foregoing description of the exemplary embodiments of the invention has been presented only for the purposes of illustration and description and is not intended to be exhaustive or to limit the invention to the precise forms disclosed. Many modifications and variations are possible in light of the above leaching.

What is claimed is:

1. A method for identifying an agent as a potential inhibitor of GLK-mediated NF-κB activity for treating a Germinal Center Kinase (GCK)-Like Kinase (GLK)-mediated disease, comprising:
   a) culturing GLK-expressing cells in the presence of the test agent;
   b) measuring the activity of NF-κB or the amount of IL-17A produced;
   c) comparing the activity of the NF-κB or the amount of the IL-17A produced in the presence of the test agent with a control; and
   d) identifying the agent as the potential inhibitor of the GLK-mediated NF-κB activity for treating the GLK-mediated disease when there is a reduction of the activity of NF-κB or the amount of IL-17A in the presence of the test agent.

2. The method of claim 1, wherein the GLK-mediated disease is selected from the group consisting of an autoimmune disease, an inflammatory disease, cancer and cancer metastasis.

3. The method of claim 1, wherein the test agent is selected from the group consisting of a small organic, molecule, an RNAi molecule, microRNA, and an antisense molecule.

4. The method of claim 1, wherein the GLK-expressing cells are GLK-expressing T cells, or GLK-expressing cancer cells.

5. The method of claim 2, wherein said cancer is a type of GLK protein-mediated cancer and independent of mammalian target of rapamycin (mTOR) protein.

6. The method of claim 2, wherein the autoimmune disease is selected from the group consisting of systemic lupus erythematosus, rheumatoid arthritis, ankylosing spondylitis, Sjogren's syndrome, Graves' disease, autoimmune encephalomyelitis, adult-onset Stills disease, alopecia, and neuromyelitis oplitica.

7. The method of claim 2, wherein the cancer is selected from the group consisting of lung carcinoma, esophageal carcinoma, glioblastoma, pancreatic cancer, breast cancer, and hepatoma.

8. The method of claim 1, wherein the GLK-expressing cells are GLK-overexpressing cells, or GLK-overexpressing cancer cells.

9. The method of claim 1, comprising the step of:
   measuring the expression level of GLK transcripts or protein.

10. The method of claim 1, further comprising the step of:
    (a) allowing a GLK protein to react at the presence of ATP with a substrate thereof in the presence of the test agent;
    (b) measuring the amount of ADP produced, the amount of ATP consumed and/or the amount of the substrate being phosphorylated; and
    (c) comparing the amount of ADP produced, the amount of ATP consumed and/or the amount of the substance being phosphorulated in the presence of the test compound with a control;
    (d) further identifying the agent as the potential inhibitor of the GLK-mediated NF-κB activity for treating a GLK-mediated disease when there is a reduction of the amount of ADP produced, the amount of ATP consumed and/or the amount of the substance being phosphorylated in the presence of the test agent.

11. The method of claim 1, further comprising the step of:
    (i) interacting a GLK protein with a substrate protein thereof in the presence of the test agent;
    (ii) measuring the interaction between the GLK protein and the substrate protein;
    (iii) comparing said interaction in the presence of the test agent with a control;
    (iv) further identifying the agent as the potential inhibitor of the GLK-mediated NF-κB activity for treating the GLK-mediated disease when there is a reduction of the interaction of the GLK protein and the substrate protein in the presence of the test agent.

12. The method of claim 1, further comprising:
    measuring the expression level of GLK transcripts or protein;

further identifying the agent as the potential inhibitor of the GLK-mediated NF-κB activity for treating the GLK-mediated disease when there is a reduction level of the GLK transcripts or protein.

* * * * *